(12) United States Patent
Alihodzic et al.

(10) Patent No.: US 7,569,550 B2
(45) Date of Patent: Aug. 4, 2009

(54) 14 AND 15 MEMBERED RING COMPOUNDS

(75) Inventors: Sulejman Alihodzic, Zagreb (HR);
Andrew Keith Forrest, Harlow (GB);
Richard Lewis Jarvest, Stevenage
(GB); Gorjana Lazarevski, Zagreb
(HR); Drazen Pavlovic, Zagreb (HR)

(73) Assignees: Glaxo Group Limited, Greenford,
Middlesex (GB); **Pliva-Istrazivacki
Institut**, Zagreb (HR)

( * ) Notice: Subject to any disclaimer, the term of this
patent is extended or adjusted under 35
U.S.C. 154(b) by 125 days.

(21) Appl. No.: 10/556,645

(22) PCT Filed: May 11, 2004

(86) PCT No.: PCT/EP2004/005082

§ 371 (c)(1),
(2), (4) Date: Mar. 15, 2007

(87) PCT Pub. No.: WO2004/101586

PCT Pub. Date: Nov. 25, 2004

(65) Prior Publication Data

US 2007/0185117 A1     Aug. 9, 2007

(30) Foreign Application Priority Data

May 13, 2003    (GB) .................................. 0310986.5

(51) Int. Cl.
*A61K 31/70* (2006.01)
*C07H 17/08* (2006.01)
(52) U.S. Cl. ............................ 514/29; 536/7.2; 536/7.4
(58) Field of Classification Search ..................... None
See application file for complete search history.

(56) References Cited

U.S. PATENT DOCUMENTS 5,288,709 A    2/1994    Freiberg et al. ............... 514/29

FOREIGN PATENT DOCUMENTS

WO      WO 03/042228       5/2003

*Primary Examiner*—Elli Peselev
(74) *Attorney, Agent, or Firm*—Reid Willis; Charles Kinzig

(57) ABSTRACT

The present invention relates to 14- or 15-membered macrolides substituted at the 4" position of formula (I)

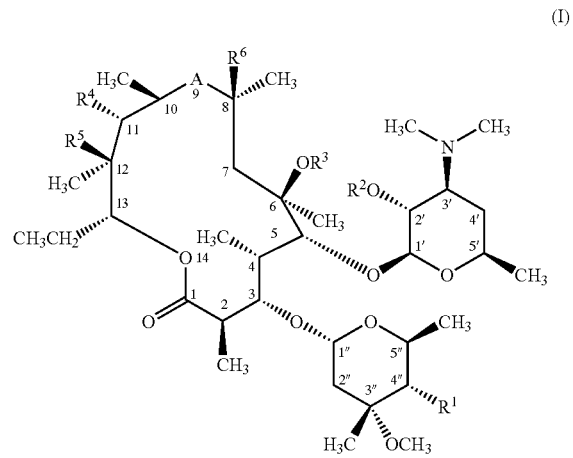

and pharmaceutically acceptable derivatives thereof, to processes for their preparation and their use in therapy or prophylaxis of systemic or topical microbial infections in a human or animal body.

10 Claims, No Drawings

14 AND 15 MEMBERED RING COMPOUNDS

This application is a 371 of International Application No. PCT/EP2004/005082, filed 11 May 2004.

The present invention relates to novel semi-synthetic macrolides having antimicrobial activity, in particular antibacterial activity. More particularly, the invention relates to 14- and 15-membered macrolides substituted at the 4" position, to processes for their preparation, to compositions containing them and to their use in medicine.

Macrolide antibacterial agents are known to be useful in the treatment or prevention of bacterial infections. However, the emergence of macrolide-resistant bacterial strains has resulted in the need to develop new macrolide compounds. For example, EP 0 895 999 describes derivatives modified at the 4" position of the macrolide ring having antibacterial activity.

According to the present invention, we have now found novel 14- and 15-membered macrolides substituted at the 4" position which also have antimicrobial activity.

Thus, the present invention provides compounds of general formula (I)

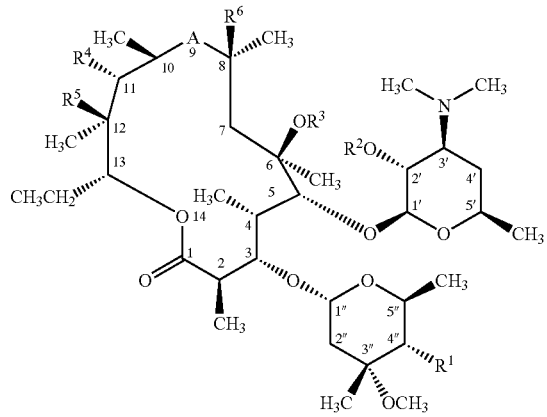

(I)

wherein
A is a bivalent radical selected from —C(O)—, —C(O)NH—, —NHC(O)—, —N($R^7$)—$CH_2$—, —$CH_2$—N($R^7$)—, —CH($NR^8R^9$)— and —C(=$NR^{10}$)—;

$R^1$ is —O($CH_2$)$_d$X$R^{11}$;

$R^2$ is hydrogen or a hydroxyl protecting group;

$R^3$ is hydrogen, $C_{1-4}$alkyl, or $C_{3-6}$alkenyl optionally substituted by 9 to 10 membered fused bicyclic heteroaryl;

$R^4$ is hydroxy, $C_{3-6}$alkenyloxy optionally substituted by 9 to 10 membered fused bicyclic heteroaryl, or $C_{1-6}$alkoxy optionally substituted by $C_{1-6}$alkoxy or —O($CH_2$)$_e$N$R^7R^{12}$, $R^5$ is hydroxy, or $R^4$ and $R^5$ taken together with the intervening atoms form a cyclic group having the following structure:

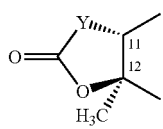

wherein
Y is a bivalent radical selected from —$CH_2$—, —CH(CN)—, —O—, —N($R^{13}$)— and —CH(S$R^{13}$)—;

$R^6$ is hydrogen or fluorine;

$R^7$ is hydrogen or $C_{1-6}$alkyl;

$R^8$ and $R^9$ are each independently hydrogen, $C_{1-6}$alkyl, —C(=$NR^{10}$)N$R^{14}R^{15}$ or —C(O)$R^{14}$, or $R^8$ and $R^9$ together form =CH($CR^{14}R^{15}$)$_f$aryl, =CH($CR^{14}R^{15}$)$_f$heterocyclyl, =$CR^{14}R^{15}$ or =C($R^{14}$)C(O)O$R^{14}$, wherein the alkyl, aryl and heterocyclyl groups are optionally substituted by up to three groups independently selected from $R^{16}$;

$R^{10}$ is —O$R^{17}$, $C_{1-6}$alkyl, —($CH_2$)$_g$aryl, —($CH_2$)$_g$heterocyclyl or —($CH_2$)$_h$O($CH_2$)$_i$O$R^7$, wherein each $R^{10}$ group is optionally substituted by up to three groups independently selected from $R^{16}$;

$R^{11}$ is a heterocyclic group having the following structure:

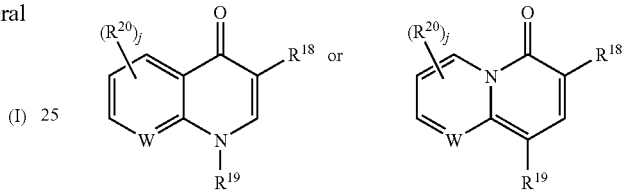

$R^{12}$ is hydrogen or $C_{1-6}$alkyl;

$R^{13}$ is hydrogen or $C_{1-4}$alkyl optionally substituted by a group selected from optionally substituted phenyl, optionally substituted 5 or 6 membered heteroaryl and optionally substituted 9 to 10 membered fused bicyclic heteroaryl;

$R^{14}$ and $R^{15}$ are each independently hydrogen or $C_{1-6}$alkyl;

$R^{16}$ is halogen, cyano, nitro, trifluoromethyl, azido, —C(O)$R^{21}$, —C(O)O$R^{21}$, —OC(O)$R^{21}$, —OC(O)O$R^{21}$, —N$R^{22}$C(O)$R^{23}$, —C(O)N$R^{22}R^{23}$, —N$R^{22}R^{23}$, hydroxy, $C_{1-6}$alkyl, —S(O)$_k C_{1-6}$alkyl, $C_{1-6}$alkoxy, —($CH_2$)$_m$aryl or —($CH_2$)$_m$heteroaryl, wherein the alkoxy group is optionally substituted by up to three groups independently selected from —N$R^{14}R^{15}$, halogen and —O$R^{14}$, and the aryl and heteroaryl groups are optionally substituted by up to five groups independently selected from halogen, cyano, nitro, trifluoromethyl, azido, —C(O)$R^{24}$, —C(O)O$R^{24}$, —OC(O)O$R^{24}$, —N$R^{25}$C(O)$R^{26}$, —C(O)N$R^{25}R^{26}$, —N$R^{25}R^{26}$, hydroxy, $C_{1-6}$alkyl and $C_{1-6}$alkoxy;

$R^{17}$ is hydrogen, $C_{1-6}$alkyl, $C_{3-7}$cycloalkyl, $C_{3-6}$alkenyl or a 5 or 6 membered heterocyclic group, wherein the alkyl, cycloalkyl, alkenyl and heterocyclic groups are optionally substituted by up to three substituents independently selected from optionally substituted 5 or 6 membered heterocyclic group, optionally substituted 5 or 6 membered heteroaryl, —O$R^{27}$, —S(O)$_n R^{27}$, —N$R^{27}R^{28}$, —CON$R^{27}R^{28}$, halogen and cyano;

$R^{18}$ is hydrogen, —C(O)O$R^{29}$, —C(O)NH$R^{29}$, —C(O)$CH_2NO_2$ or —C(O)$CH_2SO_2R^7$;

$R^{19}$ is hydrogen, $C_{1-4}$alkyl optionally substituted by hydroxy or $C_{1-4}$alkoxy, $C_{3-7}$cycloalkyl, or optionally substituted phenyl or benzyl;

$R^{20}$ is halogen, $C_{1-4}$alkyl, $C_{1-4}$thioalkyl, $C_{1-4}$alkoxy, —$NH_2$, —NH($C_{1-4}$alkyl) or —N($C_{1-4}$alkyl)$_2$;

$R^{21}$ is hydrogen, $C_{1-10}$alkyl, —($CH_2$)$_p$aryl or —($CH_2$)$_p$heteroaryl;

$R^{22}$ and $R^{23}$ are each independently hydrogen, —O$R^{14}$, $C_{1-6}$alkyl, —($CH_2$)$_q$aryl or —($CH_2$)$_q$heterocyclyl;

$R^{24}$ is hydrogen, $C_{1-10}$alkyl, —$(CH_2)_r$aryl or —$(CH_2)_r$heteroaryl;

$R^{25}$ and $R^{26}$ are each independently hydrogen, —$OR^{14}$, $C_{1-6}$alkyl, —$(CH_2)_s$aryl or —$(CH_2)_s$heterocyclyl;

$R^{27}$ and $R^{28}$ are each independently hydrogen, $C_{1-4}$alkyl or $C_{1-4}$alkoxy$C_{1-4}$alkyl;

$R^{29}$ is hydrogen,
  $C_{1-6}$alkyl optionally substituted by up to three groups independently selected from halogen, cyano, $C_{1-4}$alkoxy optionally substituted by phenyl or $C_{1-4}$alkoxy, —C(O)$C_{1-6}$alkyl, —C(O)O$C_{1-6}$alkyl, —OC(O)$C_{1-6}$alkyl, —OC(O)$C_{1-6}$alkyl, —C(O)$NR^{32}R^{33}$, —$NR^{32}R^{33}$ and phenyl optionally substituted by nitro or —C(O)O$C_{1-6}$alkyl,
  —$(CH_2)_w C_{3-7}$cycloalkyl,
  —$(CH_2)_w$heterocyclyl,
  —$(CH_2)_w$heteroaryl,
  —$(CH_2)_w$aryl,
  $C_{3-6}$alkenyl, or
  $C_{3-6}$alkynyl;

$R^{30}$ is hydrogen, $C_{1-4}$alkyl, $C_{3-7}$cycloalkyl, optionally substituted phenyl or benzyl, acetyl or benzoyl;

$R^{31}$ is hydrogen or $R^{20}$, or $R^{31}$ and $R^{19}$ are linked to form the bivalent radical —$O(CH_2)_2$— or —$(CH_2)_t$—;

$R^{32}$ and $R^{33}$ are each independently hydrogen or $C_{1-6}$alkyl optionally substituted by phenyl or —C(O)O$C_{1-6}$alkyl, or $R^{32}$ and $R^{33}$, together with the nitrogen atom to which they are bound, form a 5 or 6 membered heterocyclic group optionally containing one additional heteroatom selected from oxygen, nitrogen and sulfur;

X is —$U(CH_2)_v B$—, —$U(CH_2)_v$— or a group selected from:

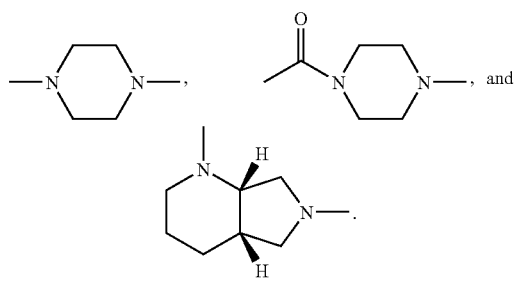

U and B are independently a divalent radical selected from —$N(R^{30})$—, —O—, —$S(O)_z$—, —$N(R^{30})C(O)$—, —$C(O)N(R^{30})$— and —$N[C(O)R^{30}]$—;

W is —$C(R^{31})$— or a nitrogen atom;

d is an integer from 2 to 6;

e is an integer from 2 to 4;

f, g, h, m, p, q, r, s and w are each independently integers from 0 to 4;

i is an integer from 1 to 6;

j, k, n and z are each independently integers from 0 to 2;

t is 2 or 3;

v is an integer from 1 to 8;

and pharmaceutically acceptable derivatives thereof.

According to another embodiment the present invention provides compounds of general formula (IA):

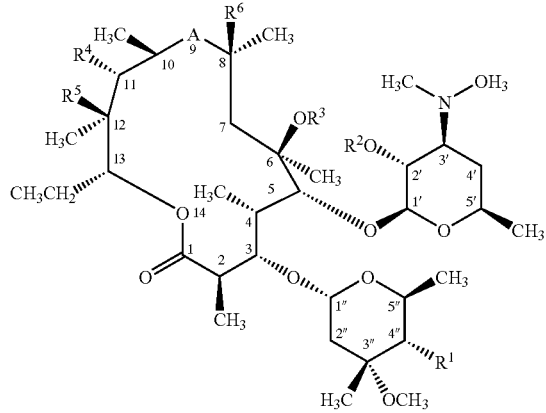

(IA)

wherein

A is a bivalent radical selected from —C(O)—, —C(O)NH—, —NHC(O)—, —$N(R^7)$—$CH_2$—, —$CH_2$—$N(R^7)$—, —$CH(NR^8R^9)$— and —$C(=NR^{10})$—;

$R^1$ is —$O(CH_2)_d XR^{11}$;

$R^2$ is hydrogen or a hydroxyl protecting group;

$R^3$ is hydrogen, $C_{1-4}$alkyl, or $C_{3-6}$alkenyl optionally substituted by 9 to 10 membered fused bicyclic heteroaryl;

$R^4$ is hydroxy, $C_{3-6}$alkenyloxy optionally substituted by 9 to 10 membered fused bicyclic heteroaryl, or $C_{1-6}$alkoxy optionally substituted by $C_{1-6}$alkoxy or —$O(CH_2)_e NR^7 R^{12}$, $R^5$ is hydroxy, or $R^4$ and $R^5$ taken together with the intervening atoms form a cyclic group having the following structure:

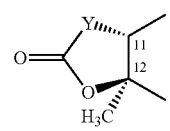

wherein

Y is a bivalent radical selected from —$CH_2$—, —CH(CN)—, —O—, —$N(R^{13})$— and —$CH(SR^{13})$—;

$R^6$ is hydrogen or fluorine;

$R^7$ is hydrogen or $C_{1-6}$alkyl;

$R^8$ and $R^9$ are each independently hydrogen, $C_{1-6}$alkyl, —$C(=NR^{10})NR^{14}R^{15}$ or —$C(O)R^{14}$, or $R^8$ and $R^9$ together form =$CH(CR^{14}R^{15})_f$aryl, =$CH(CR^{14}R^{15})_f$heterocyclyl, =$CR^{14}R^{15}$ or =$C(R^{14})C(O)OR^{14}$, wherein the alkyl, aryl and heterocyclyl groups are optionally substituted by up to three groups independently selected from $R^{16}$;

$R^{10}$ is —$OR^{17}$, $C_{1-6}$alkyl, —$(CH_2)_g$aryl, —$(CH_2)_g$heterocyclyl or —$(CH_2)_h O(CH_2)_i OR^7$, wherein each $R^{10}$ group is optionally substituted by up to three groups independently selected from $R^{16}$;

$R^{11}$ is a heterocyclic group having the following structure:

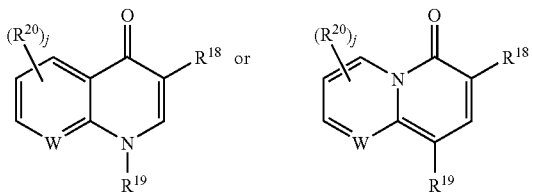

$R^{12}$ is hydrogen or $C_{1-6}$alkyl;

$R^{13}$ is hydrogen or $C_{1-4}$alkyl substituted by a group selected from optionally substituted phenyl, optionally substituted 5 or 6 membered heteroaryl and optionally substituted 9 to 10 membered fused bicyclic heteroaryl;

$R^{14}$ and $R^{15}$ are each independently hydrogen or $C_{1-6}$alkyl;

$R^{16}$ is halogen, cyano, nitro, trifluoromethyl, azido, —C(O)$R^{21}$, —C(O)O$R^{21}$, —OC(O)$R^{21}$, —OC(O)O$R^{21}$, —N$R^{22}$C(O)$R^{23}$, —C(O)N$R^{22}R^{23}$, —N$R^{22}R^{23}$, hydroxy, $C_{1-6}$alkyl, —S(O)$_k C_{1-6}$alkyl, $C_{1-6}$alkoxy, —(CH$_2$)$_m$aryl or —(CH$_2$)$_m$heteroaryl, wherein the alkoxy group is optionally substituted by up to three groups independently selected from —NR$^{14}$R$^{15}$, halogen and —OR$^{14}$, and the aryl and heteroaryl groups are optionally substituted by up to five groups independently selected from halogen, cyano, nitro, trifluoromethyl, azido, —C(O)R$^{24}$, —C(O)OR$^{24}$, —OC(O)OR$^{24}$, —NR$^{25}$C(O)R$^{26}$, —C(O)NR$^{25}$R$^{26}$, —NR$^{25}$R$^{26}$, hydroxy, $C_{1-6}$alkyl and $C_{1-6}$alkoxy;

$R^{17}$ is hydrogen, $C_{1-6}$alkyl, $C_{3-7}$cycloalkyl, $C_{3-6}$alkenyl or a 5 or 6 membered heterocyclic group, wherein the alkyl, cycloalkyl, alkenyl and heterocyclic groups are optionally substituted by up to three substituents independently selected from optionally substituted 5 or 6 membered heterocyclic group, optionally substituted 5 or 6 membered heteroaryl, —OR$^{27}$, —S(O)$_n$R$^{27}$, —NR$^{27}$R$^{28}$, —CONR$^{27}$R$^{28}$, halogen and cyano;

$R^{18}$ is hydrogen, —C(O)OR$^{29}$, —C(O)NHR$^{29}$ or —C(O)CH$_2$NO$_2$;

$R^{19}$ is hydrogen, $C_{1-4}$alkyl optionally substituted by hydroxy or $C_{1-4}$alkoxy, $C_{3-7}$cycloalkyl, or optionally substituted phenyl or benzyl;

$R^{20}$ is halogen, $C_{1-4}$alkyl, $C_{1-4}$thioalkyl, $C_{1-4}$alkoxy, —NH$_2$, —NH(C$_{1-4}$alkyl) or —N(C$_{1-4}$alkyl)$_2$;

$R^{21}$ is hydrogen, $C_{1-10}$alkyl, —(CH$_2$)$_p$aryl or —(CH$_2$)$_p$heteroaryl;

$R^{22}$ and $R^{23}$ are each independently hydrogen, —OR$^{14}$, $C_{1-6}$alkyl, —(CH$_2$)$_q$aryl or —(CH$_2$)$_q$heterocyclyl;

$R^{24}$ is hydrogen, $C_{1-10}$alkyl, —(CH$_2$)$_r$aryl or —(CH$_2$)$_r$heteroaryl;

$R^{25}$ and $R^{26}$ are each independently hydrogen, —OR$^{14}$, $C_{1-6}$alkyl, —(CH$_2$)$_s$aryl or —(CH$_2$)$_s$heterocyclyl;

$R^{27}$ and $R^{28}$ are each independently hydrogen, $C_{1-4}$alkyl or $C_{1-4}$alkoxyC$_{1-4}$alkyl;

$R^{29}$ is hydrogen or $C_{1-6}$alkyl optionally substituted by up to three groups independently selected from halogen, $C_{1-4}$alkoxy, —OC(O)C$_{1-6}$alkyl and —OC(O)OC$_{1-6}$alkyl;

$R^{30}$ is hydrogen, $C_{1-4}$alkyl, $C_{3-7}$cycloalkyl, optionally substituted phenyl or benzyl, acetyl or benzoyl;

$R^{31}$ is hydrogen or $R^{20}$, or $R^{31}$ and $R^{19}$ are linked to form the bivalent radical —O(CH$_2$)$_2$— or —(CH$_2$)$_t$—;

X is —U(CH$_2$)$_v$B—, —U(CH$_2$)$_v$— or a group selected from:

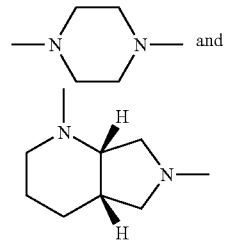

U and B are independently a divalent radical selected from —N(R$^{30}$)—, —O—, —S(O)$_z$—, —N(R$^{30}$)C(O)—, —C(O)N(R$^{30}$)— and —N[C(O)R$^{30}$]—;

W is —C(R$^{31}$)— or a nitrogen atom;

d is an integer from 2 to 6;

e is an integer from 2 to 4;

f, g, h, m, p, q, r and s are each independently integers from 0 to 4;

i is an integer from 1 to 6;

j, k, n and z are each independently integers from 0 to 2;

t is 2 or 3;

v is an integer from 2 to 8;

and pharmaceutically acceptable derivatives thereof.

The term "pharmaceutically acceptable" as used herein means a compound which is suitable for pharmaceutical use. Salts and solvates of compounds of the invention which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

The term "pharmaceutically acceptable derivative" as used herein means any pharmaceutically acceptable salt, solvate or prodrug, e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives. Preferred pharmaceutically acceptable derivatives are salts, solvates, esters, carbamates and phosphate esters. Particularly preferred pharmaceutically acceptable derivatives are salts, solvates and esters. Most preferred pharmaceutically acceptable derivatives are salts and esters, in particular salts.

The compounds of the present invention may be in the form of and/or may be administered as a pharmaceutically acceptable salt. For a review on suitable salts see Berge et al., J. Pharm. Sci., 1977, 66, 1-19.

Typically, a pharmaceutical acceptable salt may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of formula (I) and the resulting mixture evaporated to dryness (lyophilized) to obtain the acid addition salt as a solid. Alternatively, a compound of formula (I) may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Suitable addition salts are formed from inorganic or organic acids which form non-toxic salts and examples are hydrochloride, hydrobromide, hydroiodide, sulphate, bisulphate, nitrate, phosphate, hydrogen phosphate, acetate, trifluoroacetate, maleate, malate, fumarate, lactate, tartrate, citrate, formate, gluconate, succinate, pyruvate, oxalate, oxaloacetate, trifluoroacetate, saccharate, benzoate, alkyl or aryl sulphonates (eg methanesulphonate, ethanesulphonate, benzenesulphonate or p-toluenesulphonate) and isethionate. Representative examples include trifluoroacetate and formate salts, for example the bis or tris trifluoroacetate salts and the mono or diformate salts.

Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Compounds of the invention may have both a basic and an acidic centre may therefore be in the form of zwitterions.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The salts of the compound of formula (I) may form solvates (e.g. hydrates) and the invention also includes all such solvates.

The term "prodrug" as used herein means a compound which is converted within the body, e.g. by hydrolysis in the blood, into its active form that has medical effects. Pharmaceutically acceptable prodrugs are described in T. Higuchi and V. Stella, "Prodrugs as Novel Delivery Systems", Vol. 14 of the A.C.S. Symposium Series, Edward B. Roche, ed., "Bioreversible Carriers in Drug Design", American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolyzable under in vivo conditions in the human body. Suitable pharmaceutically acceptable in vivo hydrolysable ester groups include those which break down readily in the human body to leave the parent acid or its salt.

References hereinafter to a compound according to the invention include both compounds of formula (I) and their pharmaceutically acceptable derivatives.

With regard to stereoisomers, the compounds of structure (I) have more than one asymmetric carbon atom. In the general formula (I) as drawn, the solid wedge shaped bond indicates that the bond is above the plane of the paper. The broken bond indicates that the bond is below the plane of the paper.

It will be appreciated that the substituents on the macrolide may also have one or more asymmetric carbon atoms. Thus, the compounds of structure (I) may occur as individual enantiomers or diastereomers. All such isomeric forms are included within the present invention, including mixtures thereof.

Where a compound of the invention contains an alkenyl group, cis (Z) and trans (E) isomerism may also occur. The present invention includes the individual stereoisomers of the compound of the invention and, where appropriate, the individual tautomeric forms thereof, together with mixtures thereof.

Separation of diastereoisomers or cis and trans isomers may be achieved by conventional techniques, e.g. by fractional crystallization, chromatography or H.P.L.C. A stereoisomeric mixture of the agent may also be prepared from a corresponding optically pure intermediate or by resolution, such as H.P.L.C., of the corresponding mixture using a suitable chiral support or by fractional crystallization of the diastereoisomeric salts formed by reaction of the corresponding mixture with a suitable optically active acid or base, as appropriate.

The compounds of structure (I) may be in crystalline or amorphous form. Furthermore, some of the crystalline forms of the compounds of structure (I) may exist as polymorphs, which are included in the present invention.

Compounds wherein $R^2$ represents a hydroxyl protecting group are in general intermediates for the preparation of other compounds of formula (I).

When the group $OR^2$ is a protected hydroxyl group this is conveniently an ether or an acyloxy group. Examples of particularly suitable ether groups include those in which $R^2$ is a trialkylsilyl (i.e. trimethylsilyl). When the group $OR^2$ represents an acyloxy group, then examples of suitable groups $R^2$ include acetyl or benzoyl.

$R^6$ is hydrogen or fluorine. However, it will be appreciated that when A is —C(O)NH— or —CH$_2$—N(R$^7$)—, $R^6$ is hydrogen.

When $R^{11}$ is a heterocyclic group having the following structure:

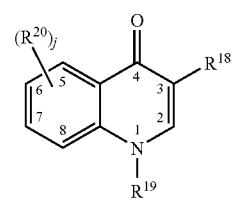

said heterocyclic is linked in the 5, 6, 7 or 8 position to the X group as above defined. In one embodiment, the heterocyclic is linked in the 6 or 7 position. In another embodiment, the heterocyclic is linked in the 5 or 8 position. When present, the $R^{20}$ group or groups may be attached at any position on the ring. In one embodiment, an $R^{20}$ group is attached at the 6 or 7 position.

When $R^{11}$ is a heterocyclic group having the following structure:

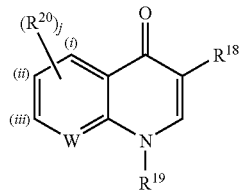

wherein W is —C($R^{31}$)— where $R^{31}$ is $R^{20}$ or $R^{31}$ and $R^{19}$ are linked to form the bivalent radical —O(CH$_2$)$_2$— or —(CH$_2$)$_t$—, said heterocyclic is linked in the (i), (ii) or (iii) position to the X group as above defined. In one embodiment, the heterocyclic is linked in the (i) position. In another embodiment, the heterocyclic is linked in the (ii) or (iii) position.

When $R^{11}$ is a heterocyclic group having the following structure:

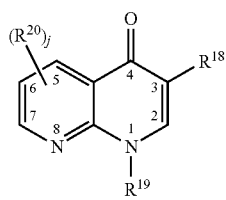

said heterocyclic is linked in the 5, 6 or 7 position to the X group as defined above. In one embodiment, the heterocyclic is linked in the 6 or 7 position. In another embodiment, the heterocyclic is linked in the 5 position. The $R^{20}$ group or groups may be attached at any position on the ring. In one embodiment, an $R^{20}$ group is attached at the 6 position.

When $R^{11}$ is a heterocyclic group having the following structure:

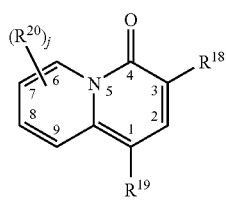

said heterocyclic is linked in the 6, 7, 8 or 9 position to the X group as above defined. In one embodiment, the heterocyclic is linked in the 7 or 8 position. In another embodiment, the heterocyclic is linked in the 6 or 9 position.

When $R^{11}$ is a heterocyclic group having the following structure:

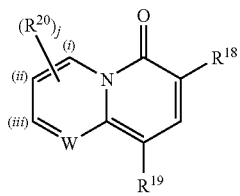

wherein W is —C($R^{31}$)— where $R^{31}$ is $R^{20}$ or $R^{31}$ and $R^{19}$ are linked to form the bivalent radical —O(CH$_2$)$_2$— or —(CH$_2$)$_t$—, said heterocyclic is linked in the (i), (ii) or (iii) position to the X group as above defined. In one embodiment, the heterocyclic is linked in the (i) position. In another embodiment, the heterocyclic is linked in the (ii) or (iii) position.

When $R^{11}$ is a heterocyclic group having the following structure:

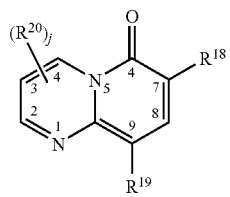

said heterocyclic is linked in the 2, 3 or 4 position to the X group as above defined. In one embodiment, the heterocyclic is linked in the 2 or 3 position. In another embodiment, the heterocyclic is linked in the 4 position.

The term "alkyl" as used herein as a group or a part of a group refers to a straight or branched hydrocarbon chain containing the specified number of carbon atoms. For example, $C_{1-10}$alkyl means a straight or branched alkyl containing at least 1, and at most 10, carbon atoms. Examples of "alkyl" as used herein include, but are not limited to, methyl, ethyl, n-propyl, n-butyl, n-pentyl, isobutyl, isopropyl, t-butyl, hexyl, heptyl, octyl, nonyl and decyl. A $C_{1-4}$alkyl group is preferred, for example methyl, ethyl, n-propyl, isopropyl, n-butyl, isobutyl or t-butyl.

The term "$C_{3-7}$cycloalkyl" group as used herein refers to a non-aromatic monocyclic hydrocarbon ring of 3 to 7 carbon atoms such as, for example, cyclopropyl, cyclobutyl, cyclopentyl, cyclohexyl or cycloheptyl.

The term "alkoxy" as used herein refers to a straight or branched chain alkoxy group containing the specified number of carbon atoms. For example, $C_{1-6}$alkoxy means a straight or branched alkoxy containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy. A $C_{1-4}$alkoxy group is preferred, for example methoxy, ethoxy, propoxy, prop-2-oxy, butoxy, but-2-oxy or 2-methylprop-2-oxy.

The term "alkenyl" as used herein as a group or a part of a group refers to a straight or branched hydrocarbon chain containing the specified number of carbon atoms and containing at least one double bond. For example, the term "$C_{2-6}$alkenyl" means a straight or branched alkenyl containing at least 2, and at most 6, carbon atoms and containing at least one double bond. Similarly, the term "$C_{3-6}$alkenyl" means a straight or branched alkenyl containing at least 3, and at most 6, carbon atoms and containing at least one double bond. Examples of "alkenyl" as used herein include, but are not limited to, ethenyl, 2-propenyl, 3-butenyl, 2-butenyl, 2-pentenyl, 3-pentenyl, 3-methyl-2-butenyl, 3-methylbut-2-enyl, 3-hexenyl and 1,1-dimethylbut-2-enyl. It will be appreciated that in groups of the form —O—$C_{2-6}$alkenyl, the double bond is preferably not adjacent to the oxygen.

The term "alkynyl" as used herein as a group or a part of a group refers to a straight or branched hydrocarbon chain containing the specified number of carbon atoms and containing at least one triple bond. For example, the term "$C_{3-6}$alkenyl" means a straight or branched alkynyl containing at least 3, and at most 6, carbon atoms containing at least one triple bond. Examples of "alkynyl" as used herein include, but are not limited to, propynyl, 1-butynyl, 2-butynyl, 1-pentynyl and 3-methyl-1-butynyl.

The term "aryl" as used herein refers to an aromatic carbocyclic moiety such as phenyl, biphenyl or naphthyl.

The term "heteroaryl" as used herein, unless otherwise defined, refers to an aromatic heterocycle of 5 to 10 members, having at least one heteroatom selected from nitrogen, oxygen and sulfur, and containing at least 1 carbon atom, including both mono and bicyclic ring systems. Examples of heteroaryl rings include, but are not limited to, furanyl, thiophenyl, pyrrolyl, pyrazolyl, imidazolyl, oxazolyl, isoxazolyl, thiazolyl, isothiazolyl, triazolyl, oxadiazolyl, tetrazolyl, thiadiazolyl, pyridyl, pyridazinyl, pyrazinyl, pyrimidinyl, triazinyl, quinolinyl, isoquinolinyl, 1,2,3,4-tetrahydroisoquinolinyl, benzofuranyl, benzimidazolyl, benzothienyl, benzoxazolyl, 1,3-benzodioxazolyl, indolyl, benzothiazolyl, furylpyridine, oxazolopyridyl and benzothiophenyl.

The term "5 or 6 membered heteroaryl" as used herein as a group or a part of a group refers to a monocyclic 5 or 6 membered aromatic heterocycle containing at least one heteroatom independently selected from oxygen, nitrogen and sulfur. Examples include, but are not limited to, furanyl, thiophenyl, pyrrolyl, pyrazolyl, imidazolyl, oxazolyl, isoxazolyl, thiazolyl, isothiazolyl, triazolyl, oxadiazolyl, tetrazolyl, pyridyl, pyridazinyl, pyrazinyl, pyrimidinyl and triazinyl.

The term "9 to 10 membered fused bicyclic heteroaryl" as used herein as a group or a part of a group refers to quinolinyl, isoquinolinyl, 1,2,3,4-tetrahydroisoquinolinyl, benzofuranyl, benzimidazolyl, benzothienyl, benzoxazolyl, 1,3-benzodioxazolyl, indolyl, benzothiazolyl, furylpyridine, oxazolopyridyl or benzothiophenyl.

The term "heterocyclyl" as used herein, unless otherwise defined, refers to a monocyclic or bicyclic three- to ten-membered saturated or non-aromatic, unsaturated hydrocarbon ring containing at least one heteroatom selected from oxygen, nitrogen and sulfur. Preferably, the heterocyclyl ring has five or six ring atoms. Examples of heterocyclyl groups include, but are not limited to, pyrrolidinyl, tetrahydrofuranyl, tetrahydrothiophenyl, imidazolidinyl, pyrazolidinyl, piperidyl, piperazinyl, morpholino, tetrahydropyranyl and thiomorpholino.

The term "5 or 6 membered heterocyclic group" as used herein as a group or part of a group refers to a monocyclic 5 or 6 membered saturated hydrocarbon ring containing at least one heteroatom independently selected from oxygen, nitrogen and sulfur. Examples of such heterocyclyl groups include, but are not limited to, pyrrolidinyl, tetrahydrofuranyl, tetrahydrothiophenyl, imidazolidinyl, pyrazolidinyl, piperidyl, piperazinyl, morpholino, tetrahydropyranyl and thiomorpholino.

The term "halogen" refers to a fluorine, chlorine, bromine or iodine atom.

The terms "optionally substituted phenyl", "optionally substituted phenyl or benzyl", "optionally substituted 5 or 6 membered heteroaryl", "optionally substituted 9 to 10 membered fused bicyclic heteroaryl" or "optionally substituted 5 or 6 membered heterocyclic group" as used herein refer to a group which is substituted by 1 to 3 groups selected from halogen, $C_{1-4}$alkyl, $C_{1-4}$alkoxy, hydroxy, nitro, cyano, amino, $C_{1-4}$alkylamino or di$C_{1-4}$alkylamino, phenyl and 5 or 6 membered heteroaryl.

In one embodiment, A is —C(O)—, —C(O)NH—, —NHC(O)—, —N($R^7$)—$CH_2$—, —$CH_2$—N($R^7$)— or —CH(N$R^8R^9$)—. In another embodiment, A is —C(O)—, —C(O)NH—, —NHC(O)—, —$CH_2$—N($R^7$)—, —CH(N$R^8R^9$)— or —C(=N$R^{10}$)—. In a further embodiment, A is —C(O)—, —C(O)NH—, —NHC(O)—, —$CH_2$—N$R^7$— or —CH(N$R^8R^9$)—. Representative examples of A include —C(O)— and —N($R^7$)—$CH_2$—. In particular, A is —C(O)—.

A representative example of $R^2$ is hydrogen.

Representative examples of $R^3$ include hydrogen and $C_{1-4}$alkyl, for example hydrogen and methyl. In particular, $R^3$ is methyl.

In one embodiment, $R^4$ and $R^5$ are hydroxy. Alternatively, $R^4$ and $R^5$ taken together with the intervening atoms form a cyclic group having the following structure:

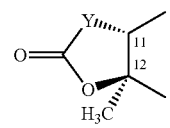

wherein Y is a bivalent radical selected from —O— and —N($R^{13}$)—.

A representative example of $R^6$ is hydrogen.

A representative example of $R^7$ is $C_{1-6}$alkyl, for example $C_{1-4}$alkyl, in particular methyl.

In one embodiment, $R^{11}$ includes heterocyclic groups having the following structures:

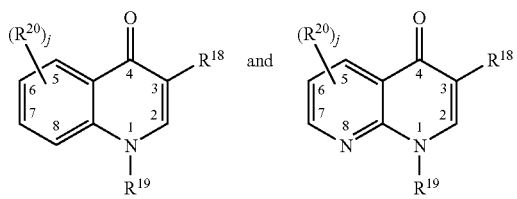

wherein the heterocyclic is linked in the 6 or 7 position to the X group as above defined; heterocyclic groups having the following structure:

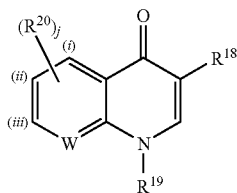

wherein W is —C(R³¹)— and R³¹ and R¹⁹ are linked to form the bivalent radical —(CH₂)ₜ—, and the heterocylic is linked in the (ii) or (iii), position to the X group as above defined; and heterocyclic groups having the following structure:

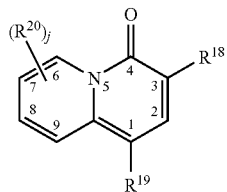

the heterocyclic is linked in the 7 or 8 position to the X group as above defined.

Representative examples of R¹¹ include heterocyclic groups having the following structures:

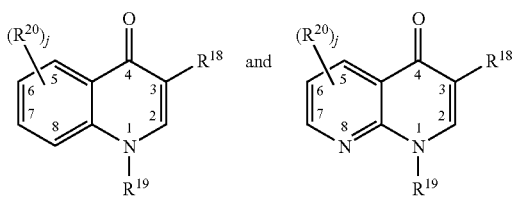

wherein the heterocyclic is linked in the 6 or 7 position to the X group as above defined, and heterocyclic groups having the following structure:

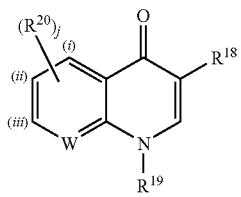

wherein W is —C(R³¹)— and R³¹ and R¹⁹ are linked to form the bivalent radical —(CH₂)ₜ—, and the heterocylic is linked in the (ii) or (iii), position to the X group as above defined.

A further representative example of R¹¹ is a heterocyclic group having the following structure:

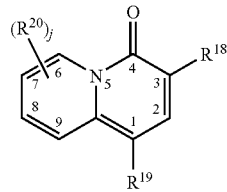

said heterocyclic is linked in the 7 or 8 position to the X group as above defined.

In one embodiment, R¹³ is hydrogen or C₁₋₄alkyl substituted by a group selected from optionally substituted phenyl, optionally substituted 5 or 6 membered heteroaryl and optionally substituted 9 to 10 membered fused bicyclic heteroaryl. Representative examples of R¹³ include hydrogen and C₁₋₄alkyl, for example hydrogen and methyl.

In one embodiment, R¹⁸ is hydrogen, —C(O)OR²⁹, —C(O)NHR²⁹ or —C(O)CH₂NO₂. In a further embodiment, R¹⁸ is —C(O)OR²⁹, —C(O)NHR²⁹ or —C(O)CH₂NO₂. A representative example of R¹⁸ is —C(O)OR²⁹, wherein R²⁹ is hydrogen.

Representative examples of R¹⁹ include C₁₋₄alkyl, in particular ethyl, and C₃₋₇cycloalkyl, in particular cyclopropyl.

In one embodiment, R²⁰ is halogen or C₁₋₄alkyl. Representative examples of R²⁰ include halogen, in particular chlorine or fluorine. Further representative examples of R²⁰ include C₁₋₄alkyl, in particular methyl.

In one embodiment, R²⁹ is hydrogen or C₁₋₆alkyl optionally substituted by up to three groups independently selected from halogen, C₁₋₄alkoxy, —OC(O)C₁₋₆alkyl and —OC(O)OC₁₋₆alkyl. A representative example of R₂₉ is hydrogen.

Representative examples of R³⁰ include hydrogen and C₁₋₄alkyl, in particular hydrogen and methyl.

A representative example of R³¹ is hydrogen, or R³¹ and R¹⁹ are linked to form the divalent radical —(CH₂)ₜ—.

In one embodiment, X is —U(CH₂)ᵥB—, —U(CH₂)ᵥ— or a group selected from:

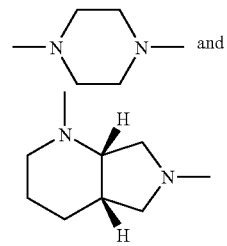

In another embodiment, X is —U(CH₂)ᵥB—, —U(CH₂)ᵥ— or a group selected from:

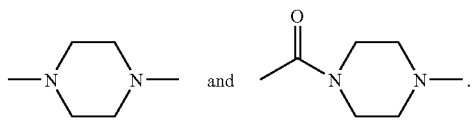

Representative examples of X are —U(CH₂)ᵥB— and —U(CH₂)ᵥ—.

Further representative examples of X are

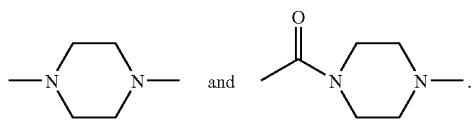

In one embodiment, U and B are independently a divalent radical selected from —N($R^{30}$)—, —O—, —S(O)$_z$— and —C(O)N($R^{30}$)—. Representative examples of U and B include the divalent radicals —N($R^{30}$)—, —O— and —S(O)$_z$—. A further representative example of U and B is —C(O)N($R^{30}$)—.

In one embodiment, when X is —U(CH$_2$)$_v$B—, U is selected from the divalent radicals —N($R^{30}$)—, and —C(O)N($R^{30}$)— and B is selected from the divalent radicals —N($R^{30}$)—, —O— and —S(O)$_z$—. In particular, U is —N($R^{30}$)— and B is selected from the divalent radicals —N($R^{30}$)—, —O— and —S(O)$_z$—. For example, U is —N($R^{30}$)— and B is selected from the divalent radicals —N($R^{30}$)— and —S(O)$_z$—.

In one embodiment, when X is —U(CH$_2$)$_v$—, U is selected from the divalent radicals —N($R^{30}$)— and —O—. For example, U is —N($R^{30}$)—.

Representative examples of Y include the bivalent radicals —O— and —N($R^{13}$)—.

Representative examples of d include 2 and 3.

A representative example of t is 3.

In one embodiment, v is an integer of from 2 to 8. A representative example of v is 2 to 4, in particular 2 or 3.

A representative example of z is 0.

Representative examples of j include 0 and 1.

It is to be understood that the present invention covers all combinations of particular and preferred groups described hereinabove. It is also to be understood that the present invention encompasses compounds of formula (I) in which a particular group or parameter, for example $R^7$, $R^{14}$, $R^{15}$, $R^{16}$, $R^{20}$, $R^{21}$, $R^{22}$, $R^{23}$, $R^{24}$, $R^{25}$, $R^{26}$, $R^{27}$, $R^{28}$, $R^{30}$, $R^{32}$, $R^{33}$, k, m, n, p, q, r, s and z may occur more than once. In such compounds it will be appreciated that each group or parameter is independently selected from the values listed.

Particularly preferred compounds of the invention are:
4"-O-(2-{[2-(3-carboxy-1-cyclopropyl-6-fluoro-4-oxo-1,4-dihydro-quinolin-7-ylamino)-ethyl]-methylamino}-ethyl)-6-O-methyl-erythromycin A 11,12-carbonate;
4"-O-(3-{[2-(3-carboxy-1-cyclopropyl-6-fluoro-4-oxo-1,4-dihydro-quinolin-7-ylamino)ethyl]-methylamino}propyl)-6-O-methyl-erythromycin A 11,12-carbonate;
4'-O-{3-[2-(2-carboxy-1-oxo-6,7-dihydro-1H,5H-pyrido[3,2,1-ij]quinoline-9-yloxy)-ethylamino]-propyl}-6-O-methyl-erythromycin A 11,12-carbonate;
4"-O-(3-{[3-(3-carboxy-1-ethyl-4-oxo-1,4-dihydro-quinolin-6-yl)propyl]-methylamino}-propyl)-6-O-methyl-erythromycin A 11,12-carbonate;
4"-O-(3-{[2-(3-carboxy-1-ethyl-6-fluoro-4-oxo-1,4-dihydro-[1,8]naphthyridin-7-ylamino)ethyl]-methylamino}propyl)-6-O-methyl-erythromycin A 11,12-carbonate;

and pharmaceutically acceptable derivatives thereof.

Further particularly preferred compounds of the invention are:
4"-O-{2-[2-(3-carboxy-1-ethyl-6-fluoro-4-oxo-1,4-dihydro-[1,8]naphthyridin-7-ylamino)ethyl]-methylamino}-ethyl}-6-O-methyl-erythromycin A;
4"-O-{3-[[3-(3-carboxy-1-ethyl-4-oxo-1,4-dihydro-quinolin-6-yl)-propyl]-methylamino]-propyl}-6-O-methyl-11-desoxy-11-(R)-amino-erythromycin A 11,12-carbamate;
4"-O-{3-[[2-(3-carboxy-1-ethyl-4-oxo-1,4-dihydro-quinolin-6-ylsulfanyl)-ethyl]-methylamino]-propyl}-6-O-methyl-11-desoxy-11-(R)-amino-erythromycin A 11,12-carbamate;
4"-O-{3-[2-(3-carboxy-7-chloro-1-cyclopropyl-4-oxo-1,4-dihydro-quinolin-6-ylamino)-ethylcarbamoyl]-propyl}-azithromycin;
4"-O-{2-[2-(3-carboxy-6-fluoro-1-cyclopropyl-4-oxo-1,4-dihydro-quinolin-7-ylamino)-ethylamino]-ethyl}-azithromycin 11,12-cyclic carbonate;
4"-O-{2-[2-(3-carboxy-7-chloro-1-cyclopropyl-4-oxo-1,4-dihydro-quinolin-6-ylamino)-ethylamino]-ethyl}-azithromycin;
4-O-{2-[2-(3-carboxy-6-fluoro-1-cyclopropyl-4-oxo-1,4-dihydro-quinolin-7-ylamino)-ethylamino]-ethyl}-azithromycin;

and pharmaceutically acceptable derivatives thereof.

Compounds according to the invention also exhibit a broad spectrum of antimicrobial activity, in particular antibacterial activity, against a wide range of clinical pathogenic microorganisms. Using a standard microtiter broth serial dilution test, compounds of the invention have been found to exhibit useful levels of activity against a wide range of pathogenic microorganisms. In particular, the compounds of the invention may be active against strains of *Staphylococcus aureus, Streptopococcus pneumoniae, Moraxella catarrhalis, Streptococcus pyogenes, Haemophilus influenzae, Enterococcus faecalis, Chlamydia pneumoniae, Mycoplasma pneumoniae* and *Legionella pneumophila*. The compounds of the invention may also be active against resistant strains, for example erythromycin resistant strains. In particular, the compounds of the invention may be active against erythromycin resistant strains of *Streptococcus pneumoniae, Streptococcus pyogenes* and *Staphylococcus aureus*.

The compounds of the invention may therefore be used for treating a variety of diseases caused by pathogenic microorganisms, in particular bacteria, in human beings and animals. It will be appreciated that reference to treatment includes acute treatment or prophylaxis as well as the alleviation of established symptoms.

Thus, according to another aspect of the present invention we provide a compound of formula (I) or a pharmaceutically acceptable derivative thereof for use in therapy.

According to a further aspect of the invention we provide a compound of formula (I) or a pharmaceutically acceptable derivative thereof for use in the therapy or prophylaxis of systemic or topical microbial infections in a human or animal subject.

According to a further aspect of the invention we provide the use of a compound of formula (I) or a pharmaceutically acceptable derivative thereof in the manufacture of a medicament for use in the treatment or prophylaxis of systemic or topical microbial infections in a human or animal body.

According to a yet further aspect of the invention we provide a method of treatment of the human or non-human animal body to combat microbial infections comprising administration to a body in need of such treatment of an effective amount of a compound of formula (I) or a pharmaceutically acceptable derivative thereof.

While it is possible that, for use in therapy, a compound of the invention may be administered as the raw chemical it is preferable to present the active ingredient as a pharmaceutical formulation eg when the agent is in admixture with a suitable pharmaceutical excipient, diluent or carrier selected with regard to the intended route of administration and standard pharmaceutical practice.

Accordingly, in one aspect, the present invention provides a pharmaceutical composition or formulation comprising at least one compound of the invention or a pharmaceutically acceptable derivative thereof in association with a pharmaceutically acceptable excipient, diluent and/or carrier. The excipient, diluent and/or carrier must be "acceptable" in the sense of being compatible with the other ingredients of the formulation and not deleterious to the recipient thereof.

In another aspect, the invention provides a pharmaceutical composition comprising, as active ingredient, at least one compound of the invention or a pharmaceutically acceptable derivative thereof in association with a pharmaceutically acceptable excipient, diluent and/or carrier for use in therapy, and in particular, in the treatment of human or animal subjects suffering from a condition susceptible to amelioration by an antimicrobial compound.

In another aspect, the invention provides a pharmaceutical composition comprising a therapeutically effective amount of the compounds of the present invention and a pharmaceutically acceptable excipient, diluent and/or carrier (including combinations thereof).

There is further provided by the present invention a process of preparing a pharmaceutical composition, which process comprises mixing at least one compound of the invention or a pharmaceutically acceptable derivative thereof, together with a pharmaceutically acceptable excipient, diluent and/or carrier.

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in a conventional manner with the aid of one or more suitable excipients, diluents and/or carriers. Acceptable excipients, diluents and carriers for therapeutic use are well known in the pharmaceutical art, and are described, for example, in Remington's Pharmaceutical Sciences, Mack Publishing Co. (A. R. Gennaro edit. 1985). The choice of pharmaceutical excipient, diluent and/or carrier can be selected with regard to the intended route of administration and standard pharmaceutical practice. The pharmaceutical compositions may comprise as—or in addition to—the excipient, diluent and/or carrier any suitable binder(s), lubricant(s), suspending agent(s), coating agent(s), solubilizing agent(s).

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

For some embodiments, the agents of the present invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule.

Drug-cyclodextrin complexes are generally useful for most dosage forms and administration routes. As an alternative to direct complexation with the drug the cyclodextrin may be used as an auxiliary additive, e. g. as a carrier, diluent or solubilizer. Alpha-, beta- and gamma-cyclodextrins are most commonly used and suitable examples are described in WO 91/11172, WO 94/02518 and WO 98/55148.

The compounds of the invention may be milled using known milling procedures such as wet milling to obtain a particle size appropriate for tablet formation and for other formulation types. Finely divided (nanoparticulate) preparations of the compounds of the invention may be prepared by processes known in the art, for example see International Patent Application No. WO 02/00196 (SmithKline Beecham).

The routes for administration (delivery) include, but are hot limited to, one or more of: oral (e. g. as a tablet, capsule, or as an ingestable solution), topical, mucosal (e. g. as a nasal spray or aerosol for inhalation), nasal, parenteral (e. g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual.

There may be different composition/formulation requirements depending on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavoring or coloring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

It is to be understood that not all of the compounds need be administered by the same route. Likewise, if the composition comprises more than one active component, then those components may be administered by different routes.

The compositions of the invention include those in a form especially formulated for parenteral, oral, buccal, rectal, topical, implant, ophthalmic, nasal or genito-urinary use. For some applications, the agents of the present invention are delivered systemically (such as orally, buccally, sublingually), more preferably orally. Hence, preferably the agent is in a form that is suitable for oral delivery.

If the compound of the present invention is administered parenterally, then examples of such administration include one or more of: intravenously, intraarterially, intraperitoneally, intrathecally, intraventricularly, intraurethrally, intrasternally, intracranially, intramuscularly or subcutaneously administering the agent; and/or by using infusion techniques.

For parenteral administration, the compound is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The compounds according to the invention may be formulated for use in human or veterinary medicine by injection (e.g. by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilizing, solubilizing and/or dispersing agents. Alternatively the active ingredient may be in sterile powder form for reconstitution with a suitable vehicle, e.g. sterile, pyrogen-free water, before use.

The compounds of the invention can be administered (e. g. orally or topically) in the form of tablets, capsules, ovules, elixirs, solutions or suspensions, which may contain flavoring or coloring agents, for immediate-, delayed-, modified-, sustained-, pulsed- or controlled-release applications.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavoring and coloring agents. Solid compositions such as tablets, capsules, lozenges, pastilles, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

The compounds of the invention may also be administered orally in veterinary medicine in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in human or veterinary medicine or as pessaries e.g. containing conventional pessary bases.

The compounds according to the invention may be formulated for topical administration, for use in human and veterinary medicine, in the form of ointments, creams, gels, hydrogels, lotions, solutions, shampoos, powders (including spray or dusting powders), pessaries, tampons, sprays, dips, aerosols, drops (e.g. eye ear or nose drops) or pour-ons.

For application topically to the skin, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water.

Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds may also be dermally or transdermally administered, for example, by use of a skin patch.

For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

As indicated, the compound of the present invention can be administered intranasally or by inhalation and is conveniently delivered in the form of a dry powder inhaler or an aerosol spray presentation from a pressurized container, pump, spray or nebuliser with the use of a suitable propellant, e. g. dichlorodifluoromethane, trichlorofluoromethane, dichlorotetrafluoroethane, a hydrofluoroalkane such as 1,1,1,2-tetrafluoroethane (HFA 134AT"") or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebuliser may contain a solution or suspension of the active compound, e. g. using a mixture of ethanol and the propellant as the solvent, which may additionally contain a lubricant, e. g. sorbitan trioleate.

Capsules and cartridges (made, for example, from gelatin) for use in an inhaler or insufflator may be formulated to contain a powder mix of the compound and a suitable powder base such as lactose or starch.

For topical administration by inhalation the compounds according to the invention may be delivered for use in human or veterinary medicine via a nebuliser.

The compounds of the invention may also be used in combination with other therapeutic agents. The invention thus provides, in a further aspect, a combination comprising a compound of the invention or a pharmaceutically acceptable derivative thereof together with a further therapeutic agent.

When a compound of the invention or a pharmaceutically acceptable derivative thereof is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. The compounds of the present invention may for example be used for topical administration with other active ingredients such as corticosteroids or antifungals as appropriate.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

The compositions may contain from 0.01-99% of the active material. For topical administration, for example, the composition will generally contain from 0.01-10%, more preferably 0.01-1% of the active material.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

For oral and parenteral administration to humans, the daily dosage level of the agent may be in single or divided doses.

For systemic administration the daily dose as employed for adult human treatment it will range from 2-100 mg/kg body weight, preferably 5-60 mg/kg body weight, which may be administered in 1 to 4 daily doses, for example, depending on the route of administration and the condition of the patient. When the composition comprises dosage units, each unit will preferably contain 200 mg to 1 g of active ingredient. The duration of treatment will be dictated by the rate of response rather than by arbitrary numbers of days.

Compounds of general formula (I) and salts thereof may be prepared by the general methods outlined hereinafter, said methods constituting a further aspect of the invention. In the following description, the groups $R^1$ to $R^{33}$, A, B, X, Y, U, W, d, e, f, g, h, i, j, k, m, n, p, q, r, s, t, v, w and z have the meaning defined for the compounds of formula (I) unless otherwise stated.

The groups $R^{11a}$, $B^a R^{11a}$ and $X^a R^{11a}$ are $R^{11}$, $BR^{11}$ and $XR^{11}$ as defined for formula (I) or groups convertible to $R^{11}$, $BR^{11}$ and $XR^{11}$. Conversion of such groups typically arises if a protecting group is needed during the reactions described below. A comprehensive discussion of the ways in which such groups may be protected and methods for cleaving the resulting protected derivatives is given by for example T. W. Greene and P. G. M Wuts in Protective Groups in Organic Synthesis $2^{nd}$ ed., John Wiley & Son, Inc 1991 and by P. J. Kocienski in Protecting Groups, Georg Thieme Verlag 1994 which are incorporated herein by reference. Examples of suitable amino protecting groups include acyl type protecting groups (e.g. formyl, trifluoroacetyl and acetyl), aromatic urethane type protecting groups (e.g. benzyloxycarbonyl (Cbz) and substituted Cbz, and 9-fluorenylmethoxycarbonyl (Fmoc)), aliphatic urethane protecting groups (e.g. t-butyloxycarbonyl (Boc), isopropyloxycarbonyl and cyclohexyloxycarbonyl) and alkyl type protecting groups (e.g. benzyl, trityl and chlorotrityl). Examples of suitable oxygen protecting groups may include for example alkyl silyl groups, such as trimethylsilyl or tert-butyldimethylsilyl; alkyl ethers such as tetrahydropyranyl or tert-butyl; or esters such as acetate. Hydroxy groups may be protected by reaction of for example acetic anhydride, benzoic anhydride or a trialkylsilyl chloride in an aprotic solvent. Examples of aprotic solvents are dichloromethane, N,N-dimethylformamide, dimethylsulfoxide, tetrahydrofuran and the like.

Compounds of formula (I) wherein U is —N($R^{30}$)— may be prepared by reaction of a 4″ aldehyde compound of formula (II) wherein A, $R^2$, $R^3$, $R^4$ and $R^5$ may be suitably protected, for example by cyclic protection between the 9 and 12 positions when A is —C(O)— and d' is an integer from 1 to 5, with a suitable protected derivative of the amine (IIIa) or (IIIb), followed where necessary by subsequent removal of the hydroxyl protecting group $R^2$ and conversion of the $B^a R^{11a}$ or $R^{11a}$ group to $BR^{11}$ or $R^{11}$.

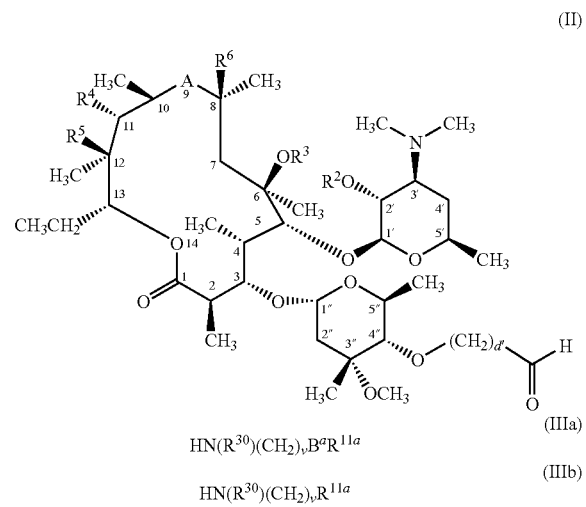

The reductive amination reaction is preferably carried out in a solvent such as methanol and DMF. A suitable reducing agent is, for example, sodium cyanoborohydride.

Compounds of formula (II) where d' is 1 or 2 may be prepared from suitably protected compounds of formula (IV) by hydroboration with 9-BBN, or other suitable boranes, followed by treatment with peroxide and then oxidation (d'=2), or by osmium tetroxide/peridoate cleavage (d'=1).

Compounds of formula (IV) can be formed by palladium-catalyzed allylation of suitably protected 4" hydroxy compounds.

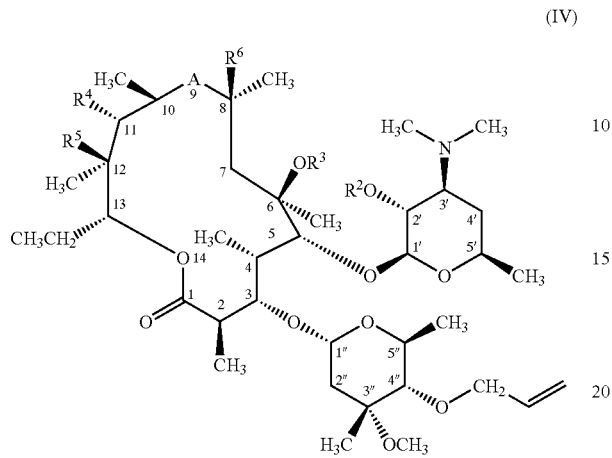

(IV)

In another embodiment of the invention, compounds of formula (I) wherein U is a group selected from —N(R$^{30}$)— and —S—, may be prepared by reaction of compounds of formula (V)

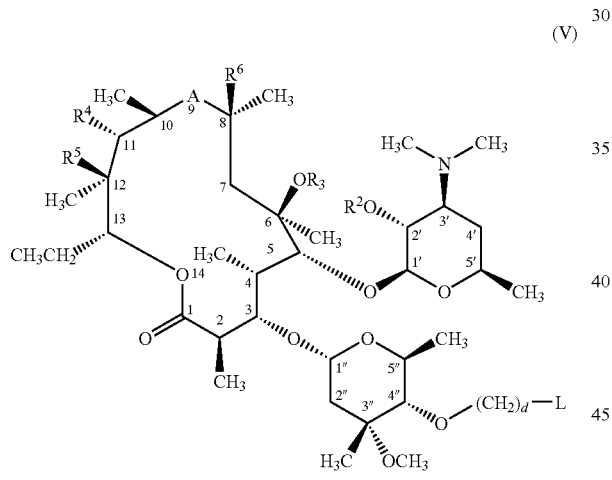

(V)

wherein d is an integer from 2 to 6 and L is a suitable leaving-group, with X$^a$R$^{11a}$ (VI) in which U is a group selected from —N(R$^{30}$)— and —S—. The reaction is preferably carried out in a solvent such as a halohydrocarbon (e.g. dichloromethane), an ether (e.g. tetrahydrofuran or dimethoxyethane), acetonitrile or ethyl acetate and the like, dimethylsulfoxide, N,N-dimethylformamide or 1-methyl-pyrrolidone and in the presence of a base, followed, if desired, by removal of the hydroxyl protecting group R$^2$ and conversion of the X$^a$R$^{11a}$ group to XR$^{11}$. Examples of the bases which may be used include organic bases such as diisopropylethylamine, triethylamine and 1,8-diazabicyclo[5.4.0]undec-7-ene (DBU), and inorganic bases such as potassium hydroxide, cesium hydroxide, tetraalkylammonium hydroxide, sodium hydride, potassium hydride and the like. Suitable leaving groups for this reaction include halide (e.g. chloride, bromide or iodide) or a sulfonyloxy group (e.g. tosyloxy or methanesulfonyloxy).

Compounds of formula (I) may be converted into other compounds of formula (I). Thus compounds of formula (I) wherein U or B is —S(O)$_z$— and z is 1 or 2 may be prepared by oxidation of the corresponding compound of formula (I) wherein z is 0. The oxidation is preferably carried out using a peracid, e.g. peroxybenzoic acid, followed by treatment with a phosphine, such as triphenylphosphine. The reaction is suitably carried out in an organic solvent such as methylene chloride. Compounds of formula (I) wherein U or B is —N(R$^{30}$)— and R$^{30}$ is C$_{1-4}$alkyl can be prepared from compounds wherein R$^{30}$ is hydrogen by reductive alkylation.

In another embodiment of the invention, compounds of formula (I) wherein U is —O—, may be prepared by reaction of compounds of formula (VII)

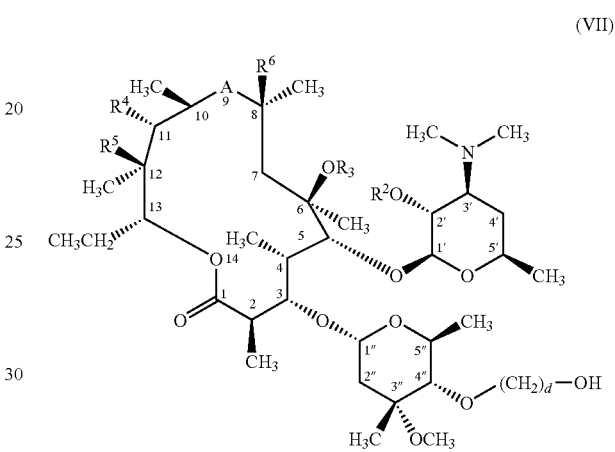

(VII)

with a suitable compound of formula X$^a$R$^{11a}$, in the presence of a catalyst such as tetrakis(triphenylphosphine)palladium.

In a further embodiment of the invention, compounds of formula (I) wherein U is —C(O)N(R$^{30}$)—, may be prepared by reaction of compounds of formula (VIII)

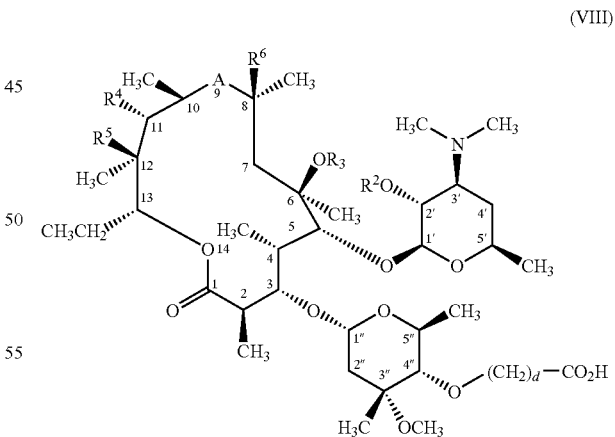

(VIII)

with a suitable amine compound.

Compounds of formula (II) wherein A is —C(O)NH— or —NHC(O)—, R$^4$ or R$^5$ are hydroxy, R$^3$ is hydrogen and R$^6$ is hydrogen are known compounds or they may be prepared by analogous methods to those known in the art. Thus they can be prepared according to the procedures described in EP 507595 and EP 503932.

Compounds of formula (II), wherein A is —C(O)NH— or —NHC(O)—, $R^4$ or $R^5$ are hydroxy and $R^3$ is $C_{1-4}$alkyl or $C_{3-6}$alkenyl optionally substituted by 9 to 10 membered fused bicyclic heteroaryl and $R^6$ is hydrogen are known compounds or they may be prepared by analogous methods to those known in the art. Thus they can be prepared according to the procedures described in WO 9951616 and WO 0063223.

Compounds of formula (II), wherein A is —C(O)NH—, $R^4$ and $R^5$ taken together with the intervening atoms form a cyclic group having the following structure:

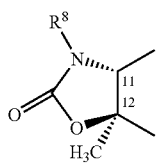

$R^3$ is $C_{1-4}$alkyl, or $C_{3-6}$alkenyl optionally substituted by 9 to 10 membered fused bicyclic heteroaryl and $R^6$ is hydrogen are known compounds or they may be prepared by analogous methods to those known in the art. Thus they can be prepared according to the procedures described in U.S. Pat. No. 6,262,030.

Compounds of formula (II), wherein A is —C(O)—, —C(O)NH—, —NHC(O)—, —N($R^7$)—$CH_2$—, —$CH_2$—N($R^7$)— or —CH($NR^8R^9$)—, $R^4$ or $R^5$ are hydroxy or $R^4$ and $R^5$ taken together with the intervening atoms form a cyclic group having the following structure:

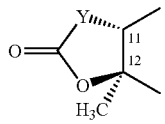

wherein Y is a bivalent radical selected from —O— and —N($R^{13}$)—, and $R^3$ is $C_{1-4}$alkyl, or $C_{3-6}$alkenyl optionally substituted by 9 to 10 membered fused bicyclic heteroaryl are known compounds or they may be prepared by analogous methods to those known in the art. Thus they can be prepared according to the procedures described in EP 307177, EP 248279, WO 0078773, WO 9742204.

Compounds of formula (II), wherein A is —C(O)NH—, —NHC(O)—, —N($CH_3$)—$CH_2$— or —$CH_2$—N($CH_3$)—, $R^4$ or $R^5$ are hydroxy or $R^4$ and $R^5$ taken together with the intervening atoms form a cyclic group having the following structure:

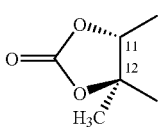

and $R^6$ is hydrogen are known compounds or they may be prepared by analogous methods to those known in the art. Thus they can be prepared according to the procedures described in EP 508699 and J. Chem. Res. Synop (1988 pages 152-153), U.S. Pat. No. 6,262,030.

Compounds of formula (II), wherein A is —C(=$NR^{10}$)—, $R^4$ or $R^5$ are hydroxy or $R^4$ and $R^5$ taken together with the intervening atoms form a cyclic group having the following structure:

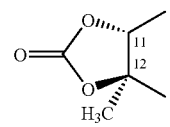

and $R^6$ is hydrogen, are known compounds or they may be prepared by analogous methods to those known in the art. Thus they can be prepared according to the procedures described in EP 284203.

Compounds of formula (II), wherein A is —C(O)—, $R^4$ and $R^5$ taken together with the intervening atoms form a cyclic group having the following structure:

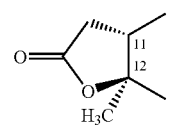

$R^6$ is hydrogen and $R^3$ is $C_{1-4}$ alkyl may be prepared by decarboxylation of a compound of formula (IX), wherein $R^{34}$ is amino protecting group followed, if required, by removal of the protecting group $R^2$ or $R^{34}$.

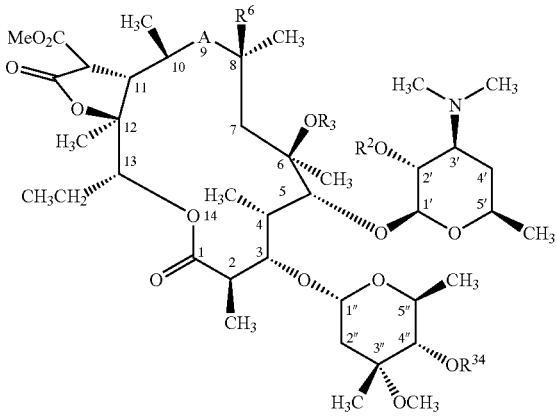

The decarboxylation may be carried out in the presence of a lithium salt such as lithium chloride, preferably in an organic solvent such as dimethylsulfoxide.

Compounds of formula (II), wherein A is —C(O)—, $R^4$ and $R^5$ taken together with the intervening atoms form a cyclic group having the following structure:

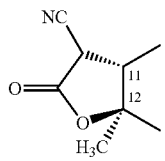

and $R_3$ is $C_{1-4}$ alkyl may be prepared according to the procedures described in WO 02/50091 and WO 02/50092.

In order that the invention may be more fully understood the following examples are given by way of illustration only.

The following abbreviations are used in the text: Ac for acetyl, $Ac_2O$ for acetic anhydride, 9-BBN for 9-borabicyclo[3.3.1]nonane, BINAP for 2,2'-bis(diphenylphosphino)-1,1'-binaphthyl, BOC for t-butoxycarbonyl, DBU for 1,8-diazabicyclo[5.4.0]undec-7-ene, DCM for dichloromethane, DIPEA for N,N-diisopropylethylamine, DMF for N,N-dimethylformamide, DMSO for dimethyl sulfoxide, $Et_2O$ for diethyl ether, EtOAc for ethyl acetate, EtOH for ethanol, HBTU for 2-(1H-benzotriazole-1-yl)-1,1,3,3-tetramethyluronium hexafluorophosphate, HOAc for acetic acid, LDA for lithium diisopropylamide, MeCN for acetonitrile, MeOH for methanol and THF for tetrahydrofuran.

EXAMPLES

2'-O-Acetyl-azithromycin-11,12-carbonate may be prepared by the procedure described by S. Djokic et al. In *J. Chem. Res. (S)* 1988, 152.

Nomenclature

In the Examples, compounds of formula (I) in which $R^{11}$ is a tricyclic heterocyclic group are referred to using the numbering system below:

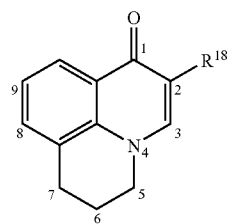

1-oxo-6,7-dihydro-1H,5H-pyrido[3,2,1-ij]quinoline

Intermediate 1: 6-[(2-Aminoethyl)amino]-7-chloro-1-cyclopropyl-4-oxo-1,4-dihydro-quinoline-3-carboxylic acid 7-Chloro-1-cyclopropyl-1,4-dihydro-6-fluoro-4-oxo-quinoline-3-carboxylic acid (56.3 g) and ethylenediamine (36 g) were dissolved in N,N-dimethylacetamide (650 mL) at 100° C. and stirred for 8.5 h at 115° C. Water (700 mL) was added to the reaction mixture cooled at room temperature. The reaction mixture was stirred at room temperature for 2 h, cooled at 0-5° C. and stirred for 1 h. The precipitate obtained was filtered, washed with cold water, cold EtOH, and dried at 110° C. under reduced pressure for 1 h. The crude product was treated with HCl (6% aqueous solution) heating for 1 h in the presence of charcoal. After filtration, the solution was cooled to 35-40° C. and a first precipitation happened. The precipitate was filtered, washed with water and dried at 110° C. for 1 h. The title compound (6.4 g) was obtained as the hydrochloride salt. The hydrochloride salt was then converted to the free base using standard conditions; ESMS m/z 320 $[M-H]^-$.

Intermediate 2: 6-(2-Amino-ethoxy)-1-ethyl-4-oxo-1,4-dihydro-quinoline-3-carboxylic acid hydrochloride a) 6-(2-Dibenzylamino-ethoxy)-1-ethyl-4-oxo-1,4-dihydro-quinoline-3-carboxylic acid 2-dibenzylamino-ethyl ester 1-Ethyl-6-hydroxy-4-oxo-1,4-dihydro-quinoline-3-carboxylic acid (GB 1433774) (1.4 g, 6 mmol) was dissolved in dry DMF (80 mL). To this was added potassium carbonate (5 g, 36 mmol) and dibenzyl-(2-chloroethyl)amine hydrochloride (4.37 g, 14.8 mmol). The mixture was heated at 65° C. with stirring for 72 h, then allowed to cool overnight. The mixture was evaporated to a small volume, diluted with water and extracted with ethyl acetate (×2). The combined organic extracts were washed with brine, dried and evaporated under reduced pressure to give a dark viscous oil (4.9 g). This residue was purified by chromatography on silica gel (100 g), eluting with 0.2-3.8% methanol in dichloromethane, to give the title compound as a brown solid (2.46 g, 60%); ESMS m/z 680 $[M+H]^+$ (100%).

b) 6-(2-Dibenzylamino-ethoxy)-1-ethyl-4-oxo-1,4-dihydro-quinoline-3-carboxylic acid sodium salt Intermediate 2a (2.44 g, 3.59 mmol) was dissolved in methanol (25 mL) and 1,4-dioxane (25 mL), then aqueous sodium hydroxide (0.4N, 8.75 mL, 3.5 mmol) was added. Stirred for 40 h then a little more sodium hydroxide was added and stirring continued for a further 72 h. Excess solid carbon dioxide was then added and the mixture evaporated to dryness under reduced pressure. Trituration with diethyl ether gave the title compound as a pale brown powder (1.382 g, 84%); ESMS m/z 457 $[M+H]^+$ for the free acid (100%).

c) 6-(2-Amino-ethoxy)-1-ethyl-4-oxo-1,4-dihydro-quinoline-3-carboxylic acid

Intermediate 2b (1.38 g, 2.89 mmol) was dissolved in 1,4-dioxane (80 mL), water (40 mL) and hydrochloric acid (2N, 2.9 mL, 5.8 mmol). This solution was hydrogenated over 20% palladium(II) hydroxide on carbon (0.6 g) at 50 psi for 18 h. The mixture was filtered through kieselguhr, washing well with water. The filtrate was then evaporated to dryness under reduced pressure to give the title compound as a pale yellow solid (1 g, 94%) (containing one equivalent of sodium chloride); ESMS m/z 277 $[M+H]^+$ for free acid (100%).

Intermediate 3: 6-(2-Aminoethylsulfanyl)-1-ethyl-4-oxo-1,4-dihydro-quinoline-3-carboxylic acid trifluoroacetate salt a) 6-Bromo-1-ethyl-4-oxo-1,4-dihydro-quinoline-3-carboxylic acid ethyl ester A mixture of potassium carbonate (2.95 g, 21.2 mmol) and 6-bromoquinolone-3-carboxylic acid (2.84 g, 10.6 mmol) in dimethylformamide (25 mL) was heated to 40° C. under argon for 10 minutes and iodoethane (3.4 mL, 42.4 mmol) was added. After 14 h the mixture was cooled and the DMF evaporated. The residue was treated with water (40 mL), cooled to 5° C. and filtered under vacuum. The resultant cream-colored solid was dried under vacuum to yield the title compound; $^1$H NMR δ [(CD$_3$)$_2$SO] 1.41 (3H, t, J=7.1 Hz), 1.54 (3H, J=7.2 Hz), 4.24 (2H, q, J=7.2 Hz), 4.40 (2H, q, J=7.1 Hz), 7.34 (1H, d, J=9 Hz), 7.76 (1H, dd, J=2.4 & 9 Hz), 8.65 (1H, d, J=2.4 Hz), 8.49 (1H, s).

b) 6-(2-t-Butoxycarbonylaminoethylsulfanyl)-1-ethyl-4-oxo-1,4-dihydro-quinoline-3-carboxylic acid ethyl ester A mixture of N-Boc-cysteinamine (0.35 g, 2 mmol), Intermediate 3a (0.32 g, 1 mmol) and potassium carbonate (0.28 g, 2 mmol) was heated in DMSO (10 mL) for 16 h at 90° C. After chromatography over silica gel eluting with dichloromethane containing an increasing concentration of methanol/ammonium hydroxide the title compound was obtained as a white solid; ESMS m/z 421 [M+H]$^+$ (100%).

c) 6-(2-t-Butoxycarbonylaminoethylsulfanyl)-1-ethyl-4-oxo-1,4-dihydro-quinoline-3-carboxylic acid sodium salt To a solution of Intermediate 3b (0.11 g, 0.27 mmol) in THF (2 mL) was added 2M sodium hydroxide (0.13 mL, 0.27 mmol). After stirring for 16 h at room temperature the mixture was saturated with carbon dioxide and the solvent evaporated. The residue was treated with methanol (10 mL), filtered and the solvent evaporated to yield the title compound as a pale yellow solid; ESMS m/z 393 [M+H]$^+$ (25%).

d) 6-(2-Aminoethylsulfanyl)-1-ethyl-4-oxo-1,4-dihydro-quinoline-3-carboxylic acid trifluoroacetate salt To Intermediate 3c (0.068 g, 0.17 mmol) was added trifluoroacetic acid (1 mL). After 1 h the solvent was evaporated to yield a green gum; $^1$H NMR δ [(CD$_3$)$_2$SO] 1.54 (3H, t, J=7.2 Hz), 3.20 (2H, q, J=6.8 Hz), 3.38 (2H, t, J=6.8 Hz), 4.56 (2H, q, J=7.2 Hz), 7.98-7.90 (2H, m), 8.40 (1H, d, J=2.0 Hz), 8.94 (1H, s).

Intermediate 4: 6-(3-Aminopropyl)-1-ethyl-4-oxo-1,4-dihydro-quinoline-3-carboxylic acid trifluoroacetate salt a) 1-Ethyl-6-iodo-4-oxo-1,4-dihydro-quinoline-3-carboxylic acid ethyl ester A mixture of 1,4-dihydro-6-iodo-4-oxo-quinoline-3-carboxylic acid (J. Ellis et al, *Aust. J. Chem.,* 1973, 26, 907) (3.15 g, 10 mmol), potassium carbonate (6.9 g, 50 mmol) and iodoethane (15.6 g, 100 mmol) in dry DMF was heated at 70° C. with vigorous stirring. After 16 h the mixture was cooled and diluted with ethyl acetate. The resultant mixture was washed with water and the organic phase separated, dried and evaporated to yield the title compound as pale yellow solid, $^1$H NMR δ (CDCl$_3$) 1.41 (3H, t, J=7.1 Hz), 1.54 (3H, t, J=7.3 Hz), 4.23 (2H, q, J=7.2 Hz), 4.40 (2H, q, J=7.1 Hz), 7.20 (1H, d, J=8.9 Hz), 7.95 (1H, dd, J=2.1 & 8.9 Hz), 8.48 (1H, s), 8.86 (1H, d, J=2.1 Hz).

b) 6-(3-t-Butoxycarbonylamino-prop-1-ynyl)-1-ethyl-4-oxo-1,4-dihydro-quinoline-3-carboxylic acid ethyl ester Intermediate 4a (0.371 g, 1 mmol), copper (I) iodide (26 mg, 0.13 mmol) and triethylamine (6.16 mL, 44 mmol) were suspended in dry acetonitrile (22 mL). The light green suspension was heated to 50° C. whilst argon was bubbled through. After 20 min, dichlorobis(triphenylphosphine)palladium (II) (0.026 g, 0.0379 mmol) and t-butoxycarbonylpropargylamine (0.264 g, 1.7 mmol) were added and the brown suspension was heated under reflux. After 2 h the reaction mixture was cooled, filtered and concentrated. The residue was taken up in dichloromethane and washed with water. The organic phase was dried and concentrated to provide a brown oil which was purified by chromatography on silica gel eluting with 0-2.5% (9:1 MeOH/20 M ammonia) in dichloromethane to yield the title compound as a yellow solid; ESMS m/z 399 (M+H$^+$).

c) 6-(3-t-Butoxycarbonylaminopropyl)-1-ethyl-4-oxo-1,4-dihydro-quinoline-3-carboxylic acid ethyl ester Intermediate 4b (0.366 mg, 0.77 mmol) in dichloromethane (10 mL) was hydrogenated over 10% palladium on charcoal (50 mg) for 16 h. The resultant mixture was filtered and the solvent evaporated to give the title compound as a yellow oil; ESMS m/z 403 [M+H]$^+$.

d) 6-(3-Aminopropyl)-1-ethyl-4-oxo-1,4-dihydro-quinoline-3-carboxylic acid ethyl ester Using a similar procedure to that described in Intermediate 3d, Intermediate 4c (355 mg, 0.88 mmol) gave the title compound as a yellow oil; ESMS m/z 303 [M+H]$^+$.

e) 6-(3-Aminopropyl)-1-ethyl-4-oxo-1,4-dihydro-quinoline-3-carboxylic acid sodium salt Using a similar procedure to that described in Intermediate 3c, Intermediate 4d (250 mg, 0.83 mmol) gave the title compound as a yellow solid; ESMS m/z 275 [M+H]$^+$.

f) 6-(3-Aminopropyl)-1-ethyl-4-oxo-1,4-dihydro-quinoline-3-carboxylic acid trifluoroacetate salt Intermediate 4e (0.06 g, 0.2 mmol) was subjected to reverse phase HPLC purification to give the title compound as white solid; $^1$H NMR δ [(CD$_3$)$_2$SO] 1.54 (3H, t, J=7.2 Hz), 2.0-2.1 (2H, m), 2.9-3.0 (4H, m), 4.58 (2H, q, J=7.2 Hz), 7.85,(1H, dd, J=2.2 & 8.8 Hz), 7.96 (1H, d, J=8.8 Hz), 8.36 (1H, d, J=1.8 Hz), 8.97 (1H, s).

Intermediate 5: 9-(2-Amino-ethoxy)-1-oxo-6,7-dihydro-1H,5H-pyrido[3,2,1-ij]quinoline-2-carboxylic acid hydrochloride a) 9-(2-Dibenzylamino-ethoxy)-1-oxo-6,7-dihydro-1H,5H-pyrido[3,2,1-ij]quinoline-2-carboxylic acid 2-dibenzylamino-ethyl ester 9-Hydroxy-1-oxo-6,7-dihydro-1H,5H-pyrido[3,2,1-ij]quinoline-2-carboxylic acid (GB1417129) (0.905 g, 3.69 mmol) was suspended in dry DMF (50 mL). To this was added potassium carbonate (3.06 g, 22 mmol) and dibenzyl-(2-chloroethyl)amine hydrochloride (2.37 g, 8 mmol). The mixture was heated at 60° C. for 16 h, then more potassium carbonate (0.55 g) and dibenzyl-(2-chloroethyl)amine hydrochloride (1.18 g, 4 mmol) were added. After a further 25 h at 75° C. the mixture was evaporated. The residue was diluted with water and extracted with ethyl acetate (×3). The combined organic extracts were washed with brine, dried and evaporated under reduced pressure. The crude product (4.0 g) was purified by chromatography on silica gel (100 g), eluting with 0-4% methanol in dichloromethane, to give the title compound (2.25 g, 89%); ESMS m/z 692 [M+H]$^+$ (100%).

b) 9-(2-Dibenzylamino-ethoxy)-1-oxo-6,7-dihydro-1H,5H-pyrido[3,2,1-ij]quinoline-2-carboxylic acid sodium salt Intermediate 5a (2.22 g, 3.21 mmol) was dissolved in methanol (30 mL) and 1,4-dioxane (20 mL), and treated with aqueous sodium hydroxide (0.4N, 8.03 mL, 3.21 mmol). The mixture was stirred for 88 h at 20° C. Solid carbon dioxide was then added and the mixture evaporated to dryness under reduced pressure. The residue was triturated with diethyl ether to give the title compound as a white powder (1.6 g, 100%); ESMS m/z 469 [M+H]$^+$ for free acid (100%).

c) 9-(2-Amino-ethoxy)-1-oxo-6,7-dihydro-1H,5H-pyrido[3,2,1-ij]quinoline-2-carboxylic acid hydrochloride Intermediate 5b (0.8 g, 1.63 mmol) was dissolved in 1,4-dioxane (100 mL), water (15 mL) and hydrochloric acid (2N, 1.6 mL, 3.2 mmol). This solution was hydrogenated over 20% palladium (II) hydroxide on carbon (0.4 g) at 50 psi for 42 h. The mixture was diluted with water and filtered through kieselguhr, washing well with water. The filtrate was then evaporated to dryness under reduced pressure to give the title compound as an off-white solid (0.54 g, 87%) (containing one equivalent of sodium chloride); ESMS m/z 289 [M+H]$^+$ for free acid (100%).

Intermediate 6: 7-(2-Amino-ethylamino)-1-ethyl-6-fluoro-4-oxo-1,4-dihydro-[1.8]naphthyridine-3-carboxylic acid trifluoroacetate a) 7-(2-tert-Butoxycarbonylamino-ethylamino)-1-ethyl-6-fluoro-4-oxo-1,4-dihydro-[1,8]naphthyridine-3-carboxylic acid ethyl ester 7-Chloro-1-ethyl-6-fluoro-4-oxo-1,4-dihydro-[1,8]naphthyridine-3-carboxylic acid ethyl ester (2.20 g, 7.37 mmol) in THF (20 mL) and MeCN (20 mL) was treated with triethylamine (3.07 mL, 22.0 mmol), followed by (2-amino-ethyl)-carbamic acid tert-butyl ester (1.41 g, 8.80 mmol) and the mixture heated to 70° C. After 26 h (2-amino-ethyl)-carbamic acid tert-butyl ester (300 mg, 1.87 mmol) was added. After a further 15 h the heating was stopped and the solvent removed in vacuo. The residue was taken up in ethyl acetate, washed with water, dried filtered, and concentrated in vacuo to give a residue which was purified by chromatography (silica gel, 30-100% ethyl acetate in petroleum ether (b.p. 40-60° C.)) to give the title compound (2.89 g); ESMS m/z 423 [M+H]$^+$.

b) 7-(2-tert-Butoxycarbonylamino-ethylamino)-1-ethyl-6-fluoro-4-oxo-1,4-dihydro-[1,8]naphthyridine-3-carboxylic acid To Intermediate 6a (2.89 g, 6.84 mmol) in THF (30 mL) was added 2 N aqueous sodium hydroxide (3.4 mL, 6.8 mmol), and the mixture stirred at room temperature. After 24 h 2 N aqueous sodium hydroxide (0.6 mL, 1.2 mmol) was added and stirring continued for a further 24 h. The solvent was then removed in vacuo, and the residue taken up in water (10 mL). Solid carbon dioxide was added, and the resulting precipitate filtered off and dried in vacuo to give the title compound (2.65 g); ESMS m/z 395 [M+H]$^+$.

c) 7-(2-Amino-ethylamino)-1-ethyl-6-fluoro-4-oxo-1,4-dihydro-[1,8]naphthyridine-3-carboxylic acid trifluoroacetate Intermediate 6b (2.65 g, 6.72 mmol) was suspended in dichloromethane (30 mL), trifluoroacetic acid (15 mL) added, and the solution stirred for 35 min. The mixture was concentrated in vacuo, and again from toluene, and again from hexane to give the title compound as a tan powder (2.92 g); ESMS m/z 295 [M+H]$^+$.

Intermediate 7: 2'-O-Acetyl-6-O-methyl-11-desoxy-11-(R)-methylamino-erythromycin A 11,12-carbamate 6-O-Methyl-11-desoxy-11-(R)-methylamino-erythromycin A 11,12-carbamate (W. R. Baker et al., *J. Org. Chem.*, 1988, 53(10), 2340-5) (0.87 g) was dissolved in DCM (20 mL) and acetone (3 mL). Solid NaHCO$_3$ (0.6 g) and Ac$_2$O (0.6 mL) were added and the reaction mixture was stirred for 1 h, then DCM (50 mL) and water (50 mL) were added. The organic phase was separated, washed with brine (20 mL), dried over K$_2$CO$_3$, filtered and concentrated under reduced pressure, affording the title compound (0.875 g); ESMS m/z 829 [MH]$^+$.

Intermediate 8: 6-((Z)-3-tert-Butoxycarbonyloxyprop-1-enyl)-1,4-dihydro-1-ethyl-4-oxo-quinoline-3-carboxylic acid ethyl ester a) 1,4-Dihydro-1-ethyl-6-iodo-4-oxo-quinoline-3-carboxylic acid ethyl ester A mixture of 1,4-dihydro-6-iodo-4-oxo-quinoline-3-carboxylic acid (J. Ellis, E. Gellert, J. Robson, *Aust. J. Chem.*, 1973, 26, 907) (3.15 g, 10 mmol), potassium carbonate (6.9 g, 50 mmol) and iodoethane (15.6 g, 100 mmol) in dry DMF was heated at 70° C. with vigorous stirring. After 16 h the mixture was cooled and diluted with ethyl acetate. The resultant mixture was washed with water and the organic phase separated, dried and evaporated to yield the title compound as pale yellow solid, $^1$H NMR δ (CDCl$_3$) 1.41 (3H, t, J=7.1 Hz), 1.54 (3H, t, J=7.3 Hz), 4.23 (2H, q, J=7.2 Hz), 4.40 (2H, q, J=7.1 Hz), 7.20 (1H, d, J=8.9 Hz), 7.95 (1H, dd, J=2.1 & 8.9 Hz), 8.48 (1H, s), 8.86 (1H, d, J=2.1 Hz).

b) 6-(3-Hydroxyprop-1-ynyl)-1,4-dihydro-1-ethyl-4-oxo-quinoline-3-carboxylic acid ethyl ester Intermediate 8a (3.71 g, 10 mmol), copper (I) iodide (0.209 g, 1.1 mmol) were suspended in dry acetonitrile (100 mL) and triethylamine (49 mL). The light green suspension was heated to 50° C. whilst argon was bubbled through. After 20 min, dichlorobis(triphenylphosphine)palladium (II) (0.21 g, 0.3 mmol) and propargyl alcohol (0.92 mL, 17 mmol) were added and the brown suspension was heated under argon at 50° C. for 3.5 h. The crude product was purified by chromatography on silica gel eluting with a gradient of dichloromethane in hexane followed by a gradient of methanol in dichloromethane. Product containing fractions were evaporated to dryness and the residue dissolved in chloroform and filtered. The filtrate was evaporated to dryness to yield the title compound as a beige solid, (1.62 g, 54%); ESMS m/z 300 [M+H]+.

c) 6-((Z)-3-Hydroxyprop-1-enyl)-1,4-dihydro-1-ethyl-4-oxo-quinoline-3-carboxylic acid ethyl ester Intermediate 8a (0.39 g, 1.3 mmol) in ethanol (10 mL) and 1,4-dioxan (5 mL) was hydrogenated at 20° C. and 1 atm over Lindlar catalyst (0.05 g). After 5 h, dichloromethane (10 mL) was added, and the hydrogenation continued for 18 h. The catalyst was filtered off and washed well with ethanol/dichloromethane. The combined filtrates were evaporated to dryness and the residue taken up in ethanol (4 mL) and dichloromethane (12 mL), and rehydrogenated at 20° C. and 1 atm over Lindlar catalyst (0.2 g) for 3 h. The catalyst was filtered off and washed well with ethanol/dichloromethane. The combined filtrates were evaporated to dryness to give the title product as a white solid, (0.394 g) ESMS m/z 302 [M+H]+.

d) 6-((Z)-3-tert-Butoxycarbonyloxyprop-1-enyl)-1,4-dihydro-1-ethyl-4-oxo-quinoline-3-carboxylic acid ethyl ester Intermediate 8a (0.393 g, 1.3 mmol) in dichloromethane (10 mL) was treated with di-tert-butyl dicarbonate (0.327 g, 1.5 mmol) and N-methylimidazole (0.01 g). After 4 d at 20° C. the crude product was purified by chromatography on silica gel eluting with a gradient of ethyl acetate in hexane to give the title product, (0.40 g, 77%). $^1$H NMR δ (CDCl$_3$) 1.42 (3H, t, J=7.1 Hz), 1.49 (9H, s), 1.51 (3H, t, J=7.2 Hz), 4.26 (2H, q, J=7.2 Hz), 4.41 (2H, q, J=7.1 Hz), 4.89 (2H, dd, J=6.4, 2.0 Hz), 5.93 (1H, dt, J=11.8, 6.4 Hz), 6.73 (1H, bd, J=11.8 Hz), 7.44 (1H, d, J=8.8 Hz), 7.58 (1H, dd, J=8.8, 2.2 Hz), 8.35 (1H, d, J=2.2 Hz), 8.49 (1H, s).

Intermediate 9: 6-(3-Aminopropyl)-1-ethyl-5-methyl-4-oxo-1,4-dihydro-3-quinolinecarboxylic acid trifluoroacetate a) Diethyl {[(4-iodo-3-methylphenyl)amino]methylidene}propanedioate 4-iodo-3-methylaniline (5.75 g) was suspended in diethyl ethoxymethylenemalonate (5.5 mL). The mixture was heated at 130° C. for 2.5 h. After cooling to ~90° C., hexane was added and the mixture stirred while cooling to room temperature. The product crystallized out, and was filtered off, washing well with more hexane. The solid was dried in vacuo to yield the title compound as a pale grey powder (7.947 g); $^1$H NMR δ (CDCl$_3$) 1.33 (3H, t), 1.38 (3H, t), 2.43 (3H, s), 4.25 (2H, q), 4.3 (2H, q), 6.69 (1H, dd), 7.01 (1H, d), 7.75 (1H, d), 8.46 (1H, d), and 10.95 (1H, br d).

b) Ethyl 6-iodo-5-methyl-4-oxo-1,4-dihydro-3-quinolinecarboxylate

Intermediate 9a (8.73 g) was suspended in Dowtherm (30 mL) then heated at 250° C. for 1 h. The mixture cooled, petroleum ether added, and the solid filtered off, washing well with more petroleum ether. The solid was dried in vacuo to give the title compound and the 7-methyl isomer as a pale grey powder (7.8 g).

c) Ethyl 1-ethyl-6-iodo-5-methyl-4-oxo-1,4-dihydro-3-quinolinecarboxylate

Intermediate 9b (3.57 g) was suspended in DMF (25 mL), potassium carbonate (1.66 g) and iodoethane (3.2 mL) added, and the mixture heated at 55° C.-60° C. for 89 h. More iodoethane (2×2 mL) being added after 64 and 69 h. The mixture was evaporated, diluted with water and extracted with ethyl acetate (×7). The combined organic extracts were washed with aqueous sodium thiosulphate solution then brine, dried and evaporated. The residue was purified by chromatography on silica gel (100 g), eluting with 40-100% ethyl acetate in petroleum ether followed by 5% methanol in dichloromethane, to give the title compound as a pale brown solid (0.492 g); ESMS m/z 386 [M+H]+.

d) Ethyl 6-[3-({[(1,1-dimethylethyl)oxy]carbonyl}amino)-1-propyn-1-yl]-1-ethyl-5-methyl-4-oxo-1,4-dihydro-3-quinolinecarboxylate Using a similar procedure to that described in Intermediate 4b, Intermediate 9c (0.485 g) and t-butoxycarbonylpropargylamine (0.332 g) gave the title compound as a yellow solid (0.62 g); ESMS m/z 413 [M+H]+.

e) Ethyl 6-[3-({[(1,1-dimethylethyl)oxy]carbonyl}amino)propyl]-1-ethyl-5-methyl-4-oxo-1,4-dihydro-3-quinolinecarboxylate Intermediate 9d (0.52 g) in DCM (30 mL) was treated with 10% Pd/C (0.4 g). The mixture filtered then hydrogenated over 10% Pd/C (0.4 g) for 1 h. The resultant mixture was filtered and the solvent evaporated to give the title compound as a yellow foam (0.58 g); ESMS m/z 417 [M+H]+.

f) 6-[3-({[(1,1-Dimethylethyl)oxy]carbonyl}amino)propyl]-1-ethyl-5-methyl-4-oxo-1,4-dihydro-3-quinolinecarboxylic acid Using a similar procedure to that described in Intermediate 6b, Intermediate 9e (0.524 g) was reacted to give the title compound as, a cream powder (0.457 g); ESMS m/z 389 [M+H]+.

g) 6-(3-Aminopropyl)-1-ethyl-5-methyl-4-oxo-1,4-dihydro-3-quinolinecarboxylic acid trifluoroacetate Using a similar procedure to that described in Intermediate 6c, Intermediate 9f (0.453 g) was reacted to give the title compound as a pale brown powder (0.505 g); ESMS m/z 289 [M+H]+.

Intermediate 10: 7-(2-Amino-ethylamino)-1-ethyl-4-oxo-4-H-quinolizine-3-carboxylic acid a) 4-Chloro-2-propylpyridine

To a solution of LDA (0.13 moles) in THF/hexanes (40 mL/40 mL) at −60° C. under argon was added a solution of 4-chloro-2-picoline (15 g) in THF (250 mL) over 20 min. After a further 30 min at −60° C. iodoethane (10.4 mL) in THF (60 mL) was added over 20 min, the reaction stirred at −60° C. for 1.5 h and then allowed to warm to −30° C. The mixture was poured into brine and extracted with dichloromethane. After drying (MgSO$_4$) and purification by chromatography eluting with dichloromethane in petroleum ether (70-100%) followed by dichloromethane containing methanol (0 to 5%) the title compound was obtained as a brown oil (12.35 g). $^1$H NMR δ (CDCl$_3$) 0.97 (3H, t), 1.75 (2H, m), 2.75 (2H, t), 7.12 (1H, m), 7.16 (1H, d), 8.42 (1H, d).

b) [2-(4-Chloro-pyridin-2-yl)-1-ethoxy-butyl]-malonic acid diethyl ester

To a solution of LDA (87.5 mmoles) in THF/hexanes (40 mL/40 mL) at −60° C. under argon was added a solution of Example 10a (12.31 g) in dry THF (150 mL) over 20 min. After a further 30 min at −60° C. diethyl ethoxymethylene malonate (18.81 g) in THF (40 mL)) was added over 20 min, the reaction stirred at −60° C. for 1.5 h and then allowed to warm to −30° C. The mixture was poured into brine and extracted with ethyl acetate. After drying (MgSO$_4$) and purification by chromatography eluting with dichloromethane in petroleum ether (70-100%) followed by dichloromethane containing methanol (0 to 5%) gave the title compound as an oil (27.38 g). ESMS m/z 372 [M+H].

c) 7-Chloro-1-ethyl-4-oxo-4-H-quinolizine-3-carboxylic acid ethyl ester

A solution of Intermediate 10b (27.38 g) and DBU (10 drops) in xylene was heated at reflux. After 16 h the mixture was cooled and purified by chromatography eluting with dichloromethane containing methanol (0 to 10%). The resultant yellow/brown solid was triturated with diethyl ether and filtered to yield the title compound as a yellow solid. ESMS m/z 280 (M+H).

d) 7-(2-t-Butoxycarbonylaminoethylamino)-1-ethyl-4-oxo-4-H-quinolizine-3-carboxylic acid ethyl ester A solution of Intermediate 10c (0.63 g), mono Boc ethylene diamine (0.45 g) and triethylamine (0.9 mL) in pyridine (15 mL) was heated at 60° C. for 16 h. After evaporation the crude product was purified by chromatography eluting with dichloromethane containing methanol (0 to 5%) to give the title product as a yellow solid (0.37 g. ESMS m/z 404 (M+H).

e) 7-(2-t-Butoxycarbonylaminoethylamino)-1-ethyl-4-oxo-4-H-quinolizine-3-carboxylic acid Using a similar procedure to that described for the preparation of Intermediate 6b, Intermediate 10d (0.334 g) gave the title compound as yellow solid ESMS m/z 376(M+H).

f) 7-(2-Aminoethylamino)-1-ethyl-4-oxo-4-H-quinolizine-3-carboxylic acid

Using a similar procedure to that described for the preparation of Intermediate 6c Intermediate 10e (0.172 g) gave the title compound as yellow solid. ESMS m/z 276 (M+H).

Intermediate 11: 6-(3-Aminopropyl)-1-ethyl-4-oxo-1,4-dihydro-1,8-naphthyridine-3-carboxylic acid trifluoroacetate salt a) Ethyl 2-[(2-chloro-5-iodo-3-pyridinyl)carbonyl]-3-(ethylamino)-2-propenoate 5-iodo-2-hydroxypyridine-3-carboxylic acid (T. R. Elworthy et al., *J. Med. Chem.*, 40, 17, 1997, 2674-2687) (7.95 g) was suspended in thionyl chloride (40 mL). DMF (4 drops) was added and the mixture refluxed for 4 h. The resultant solution was evaporated to dryness. This acid chloride was then dissolved in 1,4-dioxane (40 mL) and added dropwise to a solution of ethyl 3-(ethylamino)-2-propenoate (5.15 g) and triethylamine (10.5 mL) in 1,4-dioxane at 0° C. After 1 h the cooling bath was removed, and the reaction stirred at room temperature for 16 h. The mixture was then evaporated, saturated sodium hydrogen carbonate solution added, and extracted with ethyl acetate. The combined organic extracts were washed with brine, dried and evaporated to give a dark oil. This was purified by chromatography on silica gel, eluting with 33-45% diethyl ether in petroleum ether, to give the title compound (5.35 g); ESMS m/z 409 [M+H]$^+$.

b) Ethyl 1-ethyl-6-iodo-4-oxo-1,4-dihydro-1,8-naphthyridine-3-carboxylate

Intermediate 11a (4.92 g) was dissolved in DMF (50 mL), potassium carbonate (1.662 g) added, and the mixture heated at 50° C. for 16 h and 60° C. for 2 h. After evaporation the mixture was diluted with water and extracted with DCM. The combined organic extracts were dried and evaporated to give an oil. This was purified by chromatography on silica gel, eluting with 0-20% diethyl ether in DCM, to give the title compound as a pale yellow solid (4.33 g); ESMS m/z 373 [M+H]$^+$.

c) Ethyl 6-[3-(t-butoxycarbonylamino)-1-propyn-1-yl]-1-ethyl-4-oxo-1,4-dihydro-1,8-naphthyridine-3-carboxylate A mixture of Intermediate 11b (2.176 g), copper (I) iodide (115 mg, 0.6 mmol) and triethylamine (27.9 mL, 200 mmol) were suspended in dry acetonitrile (40 mL). The light green suspension was heated to 43° C. whilst argon was bubbled through. After 30 min, dichlorobis(triphenylphosphine)palladium (II) (0.127 g, 0.018 mmol) and N-t-butoxycarbonylpropargylamine (1.542 g) were added and the mixture was heated at 43° C. for 25 min. The reaction mixture was cooled, filtered and concentrated. The residue was taken up in dichloromethane and washed with water. The organic phase was dried and concentrated to provide a dark solid which was purified by chromatography on silica gel eluting with 0-25% (methanol/diethyl ether [1:24]) in dichloromethane to yield the title compound as a pale yellow solid (1.8 g); ESMS m/z 400 [M+H]$^+$.

d) Ethyl 6-[3-(t-butoxycarbonylamino)-1-propyl]-1-ethyl-4-oxo-1,4-dihydro-1,8-naphthyridine-3-carboxylate Intermediate 11c (0.91 g)) in dichloromethane (50 mL) was treated with 10% palladium on carbon (60 mg) and hydrogenated at room temperature and atmospheric pressure for 75 min. The reaction mixture was filtered and concentrated, and the residue purified by chromatography on silica gel eluting with 0-4% methanol in dichloromethane to give the title compound as an off-white solid (0.83 g); ESMS m/z 404 [M+H]$^+$.

e) 6-[3-(t-Butoxycarbonylamino)-1-propyl]-1-ethyl-4-oxo-1,4-dihydro-1,8-naphthyridine-3-carboxylic acid Intermediate 11d (0.825 g) was dissolved in THF (15 mL), 0.2 N sodium hydroxide (15 mL) added, and the reaction stirred for 16 h at room temperature. The mixture was evaporated to a small volume then solid carbon dioxide added. The precipitate which formed was filtered off, washed well with water, and dried in vacuo over phosphorus pentoxide to give the title compound as an off-white powder (0.709 g); ESMS m/z 376 [M+H]+.

f) 6-(3-Aminopropyl)-1-ethyl-4-oxo-1,4-dihydro-1,8-naphthyridine-3-carboxylic acid trifluoroacetate salt Intermediate 11e (0.72 g) was dissolved in DCM (12 mL), trifluoroacetic acid (4 mL) was added and the reaction stirred under argon at room temperature for 0.75 h. The solution was evaporated to dryness, and the residue triturated with diethyl ether to give, after drying, the title compound as an off-white powder (0.859 g). NMR data: $^1$H NMR (DMSO-d6) 1.43 (3H, t), 1.95 (2H, m), 2.84 (2H, m), 2.92 (2H, t), 4.68 (2H, q), 7.78 (3H, br s), 8.63 (1H, d), 8.95 (1H, d), 9.24 (1H, s) and 14.8 (1H, br s).

Intermediate 12: 9-(3-Amino-propyl)-1-oxo-6,7-dihydro-1H,5H-pyrido[3,2,1-ij]quinoline-2-carboxylic acid trifluoroacetate salt a) Diethyl 2-((3,4-dihydro-2H-quinolin-1-yl)methylene)malonate A mixture of tetrahydroquinoline (13.32 g, 100 mmol) and diethyl ethoxymethylenemalonate (21.62 g, 100 mmol) is heated to 130° C. using a Dean-Stark apparatus. After 1 hour the reaction mixture was concentrated to give the title compound as a brown oil. ESMS m/z 304 (MH+).

b) Ethyl 1-oxo-6,7-dihydro-1H,5H-pyrido[3,2,1-ij]quinoline-2-carboxylate

Diethyl 2-((3,4-dihydro-2H-quinolin-1-yl)methylene)malonate (2.5 g, 8.24 mmol) was dissolved in polyphosphoric acid and the viscous mixture stirred for 4 hours at 110° C. The reaction mixture was cooled down before adding ice. The resulting precipitate was filtered off, washed with water then dried in a dessicator in the presence of phosphorus pentoxide to give the title compound as a beige solid. ESMS m/z 258 (MH+). $^1$H NMR (DMSO-d$_6$) δ 8.55(s, 1H), 8.05 (dd, 1H), 7.54 (dd, 1H), 7.36 (dd, 1H), 4.27 (q, 2H), 4.22 (q, 2H), 3.00 (t, 2H), 2.10 (tt, 2H), 1.28 (t, 3H).

c) Ethyl 9-bromo-1-oxo-6,7-dihydro-1H,5H-pyrido[3,2,1-ij]quinoline-2-carboxylate Ethyl 1-oxo-6,7-dihydro-1H,5H-pyrido[3,2,1-ij]quinoline-2-carboxylate (290 mg, 1.13 mmol) was dissolved in acetic acid (3 mL) and bromine (197 mg, 1.23 mmol) was added dropwise. The reaction was followed by LC/MS, additional bromine (2×197 mg) was added. After 24 hours water was added and the precipitate was filtered off, washed with diethyl ether then dried in a dessicator in the presence of phosphorus pentoxide to provide an orange solid which was purified by chromatography on silica gel eluting with 0-1.5% (9:1 MeOH/20 M NH$_3$) in dichloromethane to yield the title compound as a white solid. ESMS m/z 336/338 (MH+). $^1$H NMR (CDCl$_3$) δ 8.34(d, 1H), 8.31 (s, 1H), 7.48 (d, 1H), 4.37 (q, 2H), 4.17 (t, 2H), 3.03 (t, 2H), 2.23 (tt, 2H), 1.40 (t, 3H).

d) Ethyl 9-(3-tert-butoxycarbonylamino-prop-1-ynyl)-1-oxo-6,7-dihydro-1H,5H-pyrido[3,2,1-ij]quinoline-2-carboxylate A yellow suspension of palladium acetate (73 mg, 0.32 mmol) and triphenylphosphine (191 mg, 0.72 mmol) in dry tetrahydrofuran (6 mL) under argon was cooled to 0° C. A solution of n-butyllithium (2.5M in hexanes, 284 uL) was added dropwise and after 15 minutes the dark green suspension is warmed to room temperature for 15 minutes. This suspension is then cannulated under argon into a white suspension of ethyl 9-bromo-1-oxo-6,7-dihydro-1H,5H-pyrido[3,2,1-ij]quinoline-2-carboxylate (337 mg, 1 mmol), copper iodide (84 mg, 0.44 mmol) and t-butoxycarbonylpropargylamine (198 mg, 1.28 mmol) in diethylamine (6 mL). The brown suspension is warmed to 45° C. for 2 hours then filtered off and preabsorbed on silica gel. Chromatography on silica gel eluting with 0-5% (9:1 MeOH/20 M NH$_3$) in dichloromethane provided the title compound as a brown oil. ESMS m/z 411 (MH+). $^1$H NMR (CDCl$_3$) δ 8.23(s, 1H), 8.12 (d, 1H), 7.29 (d, 1H), 5.1 (m, 1H), 4.35 (q, 2H), 4.15 (m, 2×2H), 2.97 (t, 2H), 2.19 (tt, 2H), 1.49 (s, 9H), 1.38 (t, 3H).

e) Ethyl 9-(3-tert-butoxycarbonylamino-propyl)-1-oxo-6,7-dihydro-1H,5H-pyrido[3,2,1-ij]quinoline-2-carboxylate Ethyl 9-(3-tert-butoxycarbonylamino-prop-1-ynyl)-1-oxo-6,7-dihydro-1H,5H-pyrido[3,2,1-ij]quinoline-2-carboxylate (318 mg, 0.77 mmol) was dissolved in dichloromethane (50 mL), treated with 10% palladiun on carbon (200 mg) and hydrogenated at room temperature and atmospheric pressure overnight. The reaction mixture was filtered and concentrated to provide a brown oil which was purified by chromatography on silica gel eluting with 0-1% (9:1 MeOH/20 M NH$_3$) in dichloromethane to yield the title compound as a brown oil. ESMS m/z 415 (MH+). $^1$H NMR (CDCl$_3$) δ 8.34 (s, 1H), 8.11 (bs, 1H), 7.25 (bs, 1H), 4.60 (m, 1H), 4.37 (q, 2H), 4.17 (t, 2H), 3.13 (q, 2H), 3.02 (t, 2H), 2.71 (t,2H), 2.20 (tt, 2H), 1.85 (tt, 2H), 1.44 (s, 9H), 1.40 (t, 3H).

f) 9-(3-tert-butoxycarbonylamino-propyl)-1-oxo-6,7-dihydro-1H,5H-pyrido[3,2,1-ij]quinoline-2-carboxylic acid sodium salt Ethyl 9-(3-tert-butoxycarbonylamino-propyl)-1-oxo-6,7-dihydro-1H,5H-pyrido[3,2,1-ij]quinoline-2-carboxylate (240 mg, 0.59 mmol) was dissolved in tetrahydrofuran (3 mL) and treated with 2N aqueous sodium hydroxide (0.32 mL). The solution was heated to 50° C. overnight then treated with excess solid carbon dioxide. Evaporation of the solvent gave the title compound as a beige solid. ESMS m/z 387 (MH+). NMR (DMSO-d$_6$) δ 8.83 (s, 1H), 8.11 (bs, 1H), 7.99 (s, 1H), 7.57 (s, 1H), 6.89 (bt, 1H), 4.41 (bt, 2H), 3.04 (t, 2H), 2.94 (q, 2H), 2.71 (t,2H), 2.13 (m, 2H), 1.74 (m, 2H), 1.37 (s, 9H).

g) 9-(3-Amino-propyl)-1-oxo-6,7-dihydro-1H,5H-pyrido[3,2,1-ij]quinoline-2-carboxylic acid trifluoroacetate salt 9-(3-tert-Butoxycarbonylamino-propyl)-1-oxo-6,7-dihydro-1H,5H-pyrido[3,2,1-ij]quinoline-2-carboxylic acid sodium salt (224 mg, 0.58 mmol) was dissolved in trifluoroacetic acid (3 mL). After 0.5 h at room temperature the reaction mixture was concentrated to provide the title compound as a beige solid. ESMS m/z 287 (MH+). NMR (MeOD-d$_4$) δ

8.83 (s, 1H), 8.15 (d, 1H), 7.62 (d, 1H), 4.43 (t, 2H), 3.14 (t, 2H), 2.98 (t, 2H), 2.89 (t, 2H), 2.66 (tt, 2H), 2.05 (tt, 2H).

Intermediate 13: 4"-O-{3-[2-(3-Carboxy-1-ethyl-4-oxo-1,4-dihydro-quinolin-6-ylsulfanyl)-ethylamino]-propyl}-6-O-methyl-11-desoxy-11-(R)-amino-erythromycin A 11,12-carbamate formate The title compound was prepared from Intermediate 3 by the procedure described below (see Table following Example 26).

Intermediate 14: 4"-O-Allyl-2'-O-acetylazithromycin-11,12-cyclic carbonate

To a solution of 2'-O-acetyl azithromycin-11,12-carbonate (0.408 g, 0.5 mmoL) in dry THF (4 mL) under an atmosphere of nitrogen, was added tetrakistriphenylphosphine palladium (0.057 g, 0.05 mmol) and allyl t-butyl carbonate (0.30 g, 1.9 mmoL). The resulting mixture was stirred under reflux. After 18 h of reflux TLC indicated 50% conversion of the desired product. The solvent was evaporated and the crude product dissolved in 4 mL of methanol. The mixture was stirred overnight at room temperature and then concentrated under reduced pressure. The crude product was purified by flash chromatography over silica gel eluting with 90:9:0.5; dichloromethane/MeOH/aq. $NH_3$ to yield 0.24 g (56%) of a pale yellow crystals. MS (m/z) 815 (MH$^+$).

Intermediate 15: 4"-(2-Oxo-ethoxy)-azithromycin 11,12-cyclic carbonate

To a solution of Intermediate 14 (0.20 g, 0.23 mmoL) in THF (1 mL) and water 1 mL), was added osmium tetraoxide (2.0 mL of a 2.5% solution in THF). After stirring for 5 minutes, sodium periodate (0.213 g, 1 mmoL) was added in one portion. The mixture was vigorously stirred for 12 h at 25° C. before being quenched with saturated aqueous $Na_2SO_3$ (10 mL). The resulting solution was stirred at 25° C. for 2 h and then partitioned between EtOAc (22 mL) and water (5.0 mL). The organic phase was separated and the aqueous phase was extracted with EtOAc (2×10 mL). The combined organic extracts were dried ($K_2CO_3$) and the solvents were removed under reduced pressure. Flash column chromatography (silica gel, 90:9:0.5; dichloromethane/MeOH/aq. $NH_3$) provided the corresponding aldehyde as a bright yellow solid (ca. 160 mg; 81% yield). MS (m/z) 817 (MH$^+$).

Intermediate 16: 4"-(3-Carboxy-propoxy)-azithromycin a) 4"-(3-Methoxycarbonyl-allyloxy)-azithromycin 11,12-cyclic carbonate A mixture of Intermediate 15 (587.6 mg, 0.719 mmoL) and methoxycarbonylmethylene triphenyl phosphorane (360 mg, 1.08 mmoL, 1.5 mol equiv.) in benzene (7.2 mL) was heated at reflux for 18 h. After cooling to 25° C. the solvent was removed under reduced pressure. Flash column chromatography (silica gel, 90:9:0.5 $CH_2Cl_2$:MeOH:aq. $NH_3$) furnished unsaturated methyl ester 313.8 mg, 50%) as a mixture of Z and E isomers in 1:1 ratio according LC/MS analysis. MS (m/z) 873 (MH$^+$).

b) 4"-(3-Methoxycarbonyl-propoxy)-azithromycin 11,12-cyclic carbonate

The mixture of Intermediate 16a from above (200 mg, 0.23 mmoL) was dissolved in MeOH (5 mL), treated with Pd/C (50 mg, 10 wt % Pd) and catalytically hydrogenated in Parr apparatus for 5 h. After filtration through a Celite pad, the filtrate was concentrated in vacuo and the residue purified by column chromatography (eluting with 90:9:0.5; dichloromethane/MeOH/aq. $NH_3$) to give 125 mg (62%) of pure ester as a colourless crystalline solid. MS (m/z) 875 (MH$^+$).

c) 4"-(3-Carboxy-propoxy)-azithromycin

To a solution of Intermediate 16b (875 mg, 1.0 mmoL) in 1:1 THF-water (10.0 mL) at room temperature, was added LiOH (192 mg, 4.57 mmoL), and the resulting reaction mixture was stirred at the same temperature for 12 h. The solvent was removed under reduced pressure, and the solid was azeotroped with benzene (5 mL×5) and finally dried under vacuum. The acid salt was dissolved in water and the resulting solution was made acidic by dropwise addition of 2M aqueous HCl. The precipitate was filtered of to give 787 mg (90%) of pure title compound. MS (m/z) 835 (MH$^+$).

Intermediate 17: 1-Ethyl-4-oxo-6-piperazin-1-yl-1,4-dihydro-quinoline-3-carboxylic acid a) 6-(4-tert-Butoxycarbonyl-piperezin-1-yl)-1-ethyl-4-oxo-1,4-dihydro-quinoline-3-carboxylic acid ethyl ester An oven-dried Pyrex flask was charged with sodium tert-butoxide (134.5 mg, 1.4 mmoL), $Pd_2(dba)_3$ (2.3-9.2 mg, 0.0025-0.01 mmoL) and BINAP (4.7-18.7 mg, 0.0075-0.03 mmoL). The Pyrex tube was fitted with a septum, and the air atmosphere was replaced with argon, dry THF (2-9 mL), 6-iodo-1-ethyl-4-oxo-1,4-dihydro-quinoline-3-carboxylic acid ethyl ester (371.2 mg, 1.0 mmoL), and N-Boc-piperazine (223.5 mg, 1.2 mmoL) were added by syringe. The reaction was heated to 80° C. with stirring until the starting material was consumed as judged by LC-MS analysis. The reaction mixture was cooled to room temperature, diluted with ether (15 mL), filtered, and concentrated. The crude reaction mixture was then purified further by flash chromatography on silica gel to give 356.5 mg (83%) of the title compound as a pale yelow solid. MS (m/z) 430 (MH$^+$).

b) 1-Ethyl-4-oxo-6-piperazin-1-yl-1,4-dihydro-quinoline-3-carboxylic acid ethyl ester A solution of Intermediate 17a (429.5 mg, 1.0 mmoL) in 10 mL of $CH_2Cl_2$ and trifluoroacetic acid (1:1) was stirred at 0° C. for 5 hours. The volatile materials were evaporated under reduced pressure, and the residue was triturated with diethylether and filtered. The resulting product (354.7 mg, 80%) was used without further purification in the next step. MS (m/z) 330 (MH$^+$).

c) 1-Ethyl-4-oxo-6-piperazin-1-yl-1,4-dihydro-quinoline-3-carboxylic acid

Intermediate 17b was dissolved in a mixture of THF, water and 5 eq of NaOH and stirred at 80° C. until TLC showed a complete conversion to the title compound. MS (m/z) 302 (MH$^+$).

Example 1

4"-O-(2-{[2-(3-Carboxy-1-cyclopropyl-6-fluoro-4-oxo-1,4-dihydro-quinolin-7-ylamino)-ethyl]-methylamino}-ethyl)-6-O-methyl-erythromycin A 11,12-carbonate bis trifluoroacetate

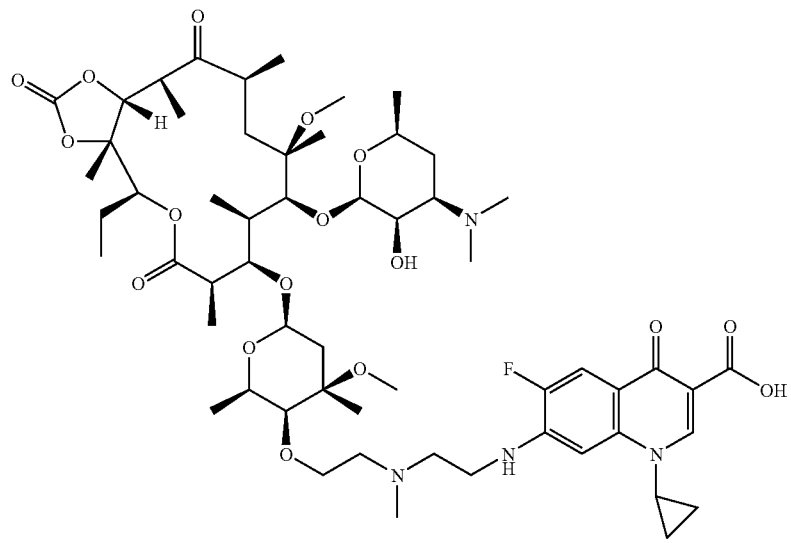

a) 2'-O,3'-N-bis(Benzyloxycarbonyl)-3'-N-desmethyl-6-O-methyl-erythromycin A To a stirred mixture of 6-O-methyl-erythromycin A (20 g, 26.8 mmol) and sodium hydrogen carbonate (30 g) cooled in an ice bath was added portionwise benzyl chloroformate (60 mL). After 10 min the ice bath was removed and the mixture was stirred for 15 min. The reaction was then heated at 60-70° C. for 1 h. After cooling, the reaction mixture was loaded onto a silica gel column (150 g) and eluted with a gradient of 10-50% ethyl acetate in hexane. Evaporation of the product containing fractions gave the title product as a white solid foam (20.22 g); ESMS m/z 1024 [M+Na]$^+$, 1060 [M+NH4+acetonitrile]$^+$.

b) 4"-O-Allyloxycarbonyl-2'-O,3'-N-bis(benzyloxycarbonyl)-3'-N-desmethyl-6-O-methyl-erythromycin A 11,12-carbonate Example 1a (13 g, 12.97 mmol) in dichloromethane (50 mL) at 0° C. under argon was added pyridine (11.5 mL) and a solution of phosgene in toluene (20%, 30 mL). After 30 min the mixture was allowed to warm to 20° C. After 2.5 h the reaction was recooled to 0° C. and allyl alcohol (5 mL) was added dropwise. After stirring at 0° C. for 15 min and 20° C. for 30 min the mixture was poured onto ice. Extraction with diethyl ether and washing with water, 5% aq citric acid, and saturated aq sodium hydrogen carbonate gave a crude product solution which was dried, evaporated and purified by chromatography (silica gel, 20-50% ethyl acetate in hexane) to give the title product as a white solid foam (12.5 g); ESMS m/z 1129 [M+NH4]$^+$, 1134 [M+Na]$^+$, 1170 [M+NH4+acetonitrile]$^+$.

c) 4"-O-Allyl-2'-O,3'-N-bis(benzyloxycarbonyl)-3'-N-desmethyl-6-O-methyl-erythromycin A 11,12-carbonate Example 1b (7.9 g, 7.1 mmol) in tetrahydrofuran (50 mL) was treated with tetrakis(triphenylphosphine)palladium (0.16 g). The reaction was heated to reflux for 30 min after which time methyl allyl carbonate (1.7 mL) was added. After a further 1.75 h reflux, the reaction was cooled and evaporated to dryness. The residue was purified by chromatography (silica gel, 0-30% ethyl acetate in dichloromethane) to give the title product as a white solid foam (3.93 g); ESMS m/z 1085 [M+NH4]$^+$, 1090 [M+Na]$^+$, 1126 [M+NH4+acetonitrile]$^+$.

d) 2'-O,3'-N-bis(Benzyloxycarbonyl)-4"-O-{2-[2-(3-Carboxy-1-cyclopropyl-6-fluoro-4-oxo-1,4-dihydro-quinolin-7-ylamino)-ethylamino]-ethyl}-6-O-methyl-3'-N-desmethyl-erythromycin A 11,12-carbonate To Example 1c (0.256 g, 0.25 mmol) in tetrahydrofuran (1 mL) and water (1 mL) under argon was added osmium tetroxide (4% in water, 0.015 mL). After 5 min sodium periodate (0.213 g, 1 mmol) was added. After 2.5 h the mixture was diluted with diethyl ether and water. The organic phase was washed with saturated aq. sodium thiosulphate, dried, and evaporated to dryness to give the crude aldehyde as a white solid foam (0.255 g). This material (0.094 g) in methanol (1.5 mL) and dimethylformamide (1.5 mL) was treated with acetic acid (0.15 mL), 7-(2-aminoethylamino)-1-cyclopropyl-6-fluoro-4-oxo-1,4-dihydro-quinoline-3-carboxylic acid (Yoshida et al, *J. Pharm. Soc.* Japan, 1990, 110, 258) (0.031 g, 0.1 mmol) and sodium cyanoborohydride (0.013 g, 0.2 mmol). After 3 h the reaction was evaporated to dryness, and the residue purified by chromatography (silica gel, 0-10% 2 M methanolic ammonia in dichloromethane) to give the title product as a white solid foam (0.066 g); ESMS m/z 1359 [M+H]+.

e) 4"-O-(2-{[2-(3-Carboxy-1-cyclopropyl-6-fluoro-4-oxo-1,4-dihydro-quinolin-7-ylamino)-ethyl]-methylamino}-ethyl)-6-O-methyl-erythromycin A 11,12-carbonate bistrifluoroacetate Example 1d (0.066 g) in ethanol (20 mL) and dioxan (10 mL) was hydrogenated at 50 psi over palladium hydroxide (20% on carbon, 0.080 g) for 72 h. The catalyst was removed by filtration, washed well with dioxan and ethanol, and the combined filtrates evaporated to dryness. The residue was taken up in ethanol (20 mL) and dioxan (10 mL), and 28% aq formaldehyde (2 mL), 0.7 min pH 4.5 acetate buffer (2 mL) and palladium hydroxide (20% on carbon, 0.080 g) added. The mixture was hydrogenated at 50 psi for a further 5 days, then the catalyst was removed by filtration, washed well with dioxan and ethanol, and the combined filtrates evaporated to dryness. The residue was purified by chromatography (silica gel, 5-10% methanol in dichloromethane then 10-20% 2 M methanolic ammonia in dichloromethane). Later fractions contained impure title product. Early eluted fractions contained 3'-N-benzyloxycarbonyl-4"-O-(2-{[2-(3-carboxy-1-cyclopropyl-6-fluoro-4-oxo-1,4-dihydro-quinolin-7-ylamino)-ethyl]-methylamino}-ethyl)-6-O-methyl-3'-N-desmethyl-erythromycin A 11,12-carbonate, (0.01 g) which was dissolved in ethanol (10 mL) and dioxan (5 mL) and hydrogenated at 50 psi over palladium (10% on carbon, 0.1 g). After 3 h 28% aq. formaldehyde (1.5 mL), 0.7M pH 4.5 acetate buffer (2.5 mL) was added and the hydrogenation continued for 24 h. After filtration and evaporation, the residue was purified by chromatography (silica gel, 2-15% 2M methanolic ammonia in dichloromethane) giving impure product. Both batches of impure title product were purified by preparative HPLC (acetonitrile/water/0.1% trifluoroacetic acid eluent) to give the title compound as a gum (0.004 g); ESMS m/z 1119 [M+H]+.

Example 2

4"-O-(3-{[2-(3-Carboxy-1-cyclopropyl-6-fluoro-4-oxo-1,4-dihydro-quinolin-7-ylamino)ethyl]-methylamino}-propyl)-6-O-methyl-erythromycin A 11,12-carbonate

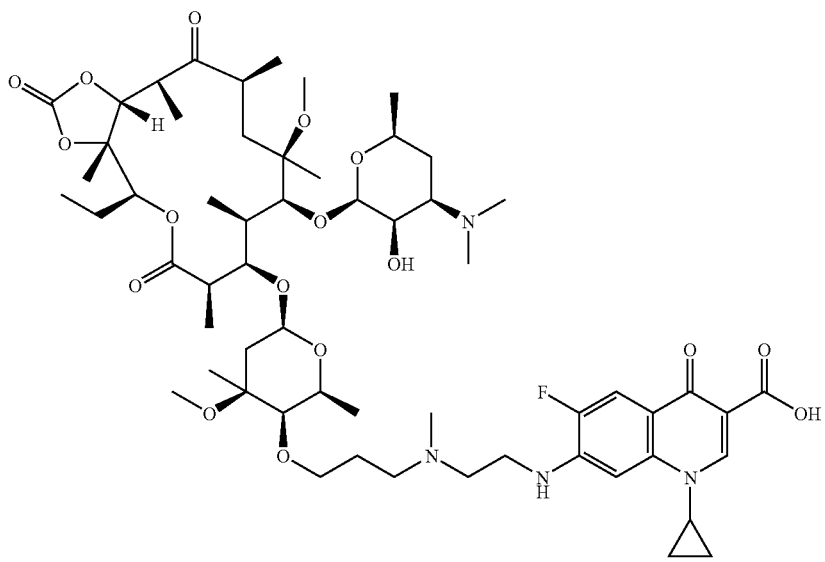

a) 2'-O,3'-N-bis(Benzyloxycarbonyl)-4"-O-(3-hydroxypropyl)-3'-N-desmethyl-6-O-methyl-erythromycin A 11,12-carbonate Example 1c (0.97 g, 0.908 mmol) in tetrahydrofuran (6 mL) was treated with 9-BBN (0.5M in tetrahydrofuran, 3.6 mL). After 1.5 h the reaction was cooled to 0° C. and sodium hydroxide (2 M, 1.5 mL) and hydrogen peroxide (27% in water, 2.1 mL) were added. After 5 min the cooling bath was removed and the reaction stirred for 15 m, then diluted with diethyl ether and water. The organic phase was washed with water and brine, dried (MgSO4), and evaporated to dryness. The residue was purified by chromatography (silica gel, 0-50% ethyl acetate in dichloromethane) to give the title product as a white solid foam (0.80 g, 76%); ESMS m/z 1103 [M+NH4]+, 1108 [M+Na]+.

b) 2'-O,3'-N-bis(Benzyloxycarbonyl)-4"-O-{3-[2-(3-carboxy-1-cyclopropyl-6-fluoro-4-oxo-1,4-dihydro-quinolin-7-ylamino)-ethylamino]-propyl}]-6-O-methyl-3'-N-desmethyl-erythromycin A 11,12-carbonate trifluoroacetate To Example 2a (0.411 g, 0.378 mmol) in dichloromethane (6 mL) at 0° C. under argon was added Dess-Martin periodinane (0.176 g, 0.41 mmol). After 1.5 h, the cooling bath was removed and the reaction stirred for a further 30 min then diluted with dichloromethane, washed with saturated aq sodium hydrogen carbonate, dried (MgSO₄), and evaporated to dryness to give the title product as a white solid foam (0.42 g). This material (0.169 g) in methanol (2 mL) and dimeth- Example 3

4"-O-{3-[2-(3-Carboxy-1-ethyl-4-oxo-1,4-dihydro-quinolin-6-yloxy)-ethylamino]-propyl}-6-O-methyl-erythromycin A 11,12-carbonate bis trifluoroacetate

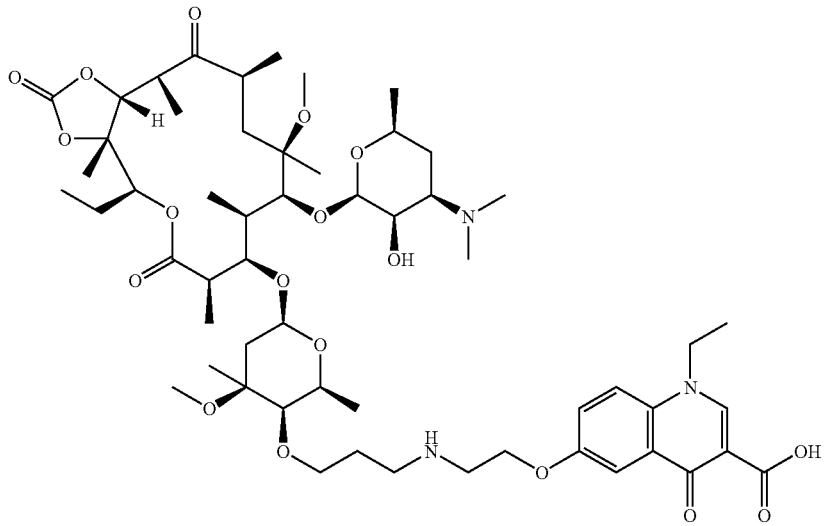

ylformamide (2 mL) was treated with acetic acid (0.2 mL), 7-(2-aminoethylamino)-1-cyclopropyl-6-fluoro-4-oxo-1,4-dihydro-quinoline-3-carboxylic acid (0.048 g, 0.16 mmol) and sodium cyanoborohydride (0.02 g, 0.32 mmol). After 1.5 h the reaction was evaporated to dryness, and the residue purified by preparative HPLC (acetonitrile/water/0.1% trifluoroacetic acid eluent) to give the title product (0.10 g); ESMS m/z 1373 [M+H]⁺.

c) 4"-O-(3-{[2-(3-Carboxy-1-cyclopropyl-6-fluoro-4-oxo-1,4-dihydro-quinolin-7-ylamino)-ethyl]-methylamino}-propyl)-6-O-methyl-erythromycin A 11,12-carbonate Example 2b (0.1 g) in ethanol (20 mL) and dioxan (10 mL) was hydrogenated at 50 psi over palladium (10% on carbon, 0.050 g) for 7 h. 28% aq. Formaldehyde (2.5 mL), 0.7 M pH 4.5 acetate buffer (5 mL) was added and the hydrogenation continued for 24 h. After filtration and evaporation, dichloromethane (10 mL) and methanol (2 mL) were added to the residue and insoluble material removed by filtration. The soluble material was passed down a silica gel column eluting with 2-15% 2 M methanolic ammonia in dichloromethane. The fractions containing the title material were dissolved in ethanol (10 mL), 28% aq. formaldehyde (1 mL) and 0.7 M pH 4.5 acetate buffer (2 mL) and the mixture hydrogenated at 50 psi over palladium (10% on carbon, 0.1 g) for 30 h. The catalyst was removed by filtration and the residue evaporated to dryness. Dichloromethane (10 mL) and methanol (2 mL) were added to the residue and insoluble material removed by filtration. The soluble material was passed down a silica gel column eluting with 2-15% 2 M methanolic ammonia in dichloromethane to give the title product, as a gum (0.012 g); ¹H NMR (CD₃OD) (inter alia) 1.8 (2H, m), 2.4 (3H, s), 2.6 (2H, m), 2.8 (2H, m), 3.5 (2H, m), 3.7 (2H, m), 4.55 (1H, d), 4.65 (1H, s), 4.85 (1H, d), 5.0 (1H, dd), 7.2 (1H, d), 7.8 (1H, d), 8.7 (1H, s); ESMS m/z 1133 [M+H]⁺.

a) 4"-O-(3-Hydroxypropyl)-6-O-methyl-erythromycin A 11,12-carbonate

Example 2a (2.57 g, 2.37 mmol) in ethanol (25 mL) and dioxan (25 mL) was hydrogenated at 50 psi over palladium (10% on carbon, 0.2 g) for 26 h. The catalyst was removed by filtration and the soluble material taken up in ethanol (50 mL), pH 4.5 buffer (4 mL) and 37% aq formaldehyde solution (4 mL) were added and the mixture hydrogenated at 50 psi over palladium (10% on carbon, 0.5 g). After 18 h, the reaction mixture was filtered, and the catalyst washed well with ethanol and dioxan. The combined filtrates were purified by chromatography on silica gel eluting with 0-10% 2 M methanolic ammonia in dichloromethane to give the title product as a white foam (1.21 g); ESMS m/z 832 [M+H]⁺.

b) 4"-O-{3-[2-(3-Carboxy-1-ethyl-4-oxo-1,4-dihydro-quinolin-6-yloxy)-ethylamino]-propyl}-6-O-methyl-erythromycin A 11,12-carbonate bis trifluoroacetate To Example 3a (0.099 g, 0.119 mmol) in dichloromethane (2 mL) at 0° C. under argon was added Dess-Martin periodinane (0.176 g, 0.41 mmol). After 15 min the reaction was allowed to warm to 20° C. After a total reaction time of 100 min the reaction mixture was diluted with dichloromethane, washed with saturated. aq sodium hydrogen carbonate, dried, and evaporated to dryness to give the crude aldehyde as a white solid foam. This material in DMF (1 mL) and methanol (1 mL) was treated with acetic acid (0.1 mL), Intermediate 2 (0.038 g, 0.12 mmol), sodium acetate (0.01 g) and sodium cyanoborohydride (0.015 g, 0.24 mmol). After 14 h the reaction was evaporated to dryness, and the residue partially purified by chromatography on silica gel eluting with 5-20% 2 M methanolic ammonia in dichloromethane followed by preparative HPLC (acetonitrile/water/0.1% trifluoroacetic acid eluent) to give the title product (0.013 g); ESMS m/z 1090 [M+H]⁺.

Example 4

4"-O-{3-[2-(3-Carboxy-1-ethyl-4-oxo-1,4-dihydro-quinolin-6-ylsulfanyl)-ethylamino]-propyl}-6-O-methyl-erythromycin A 11,12-carbonate bisformate

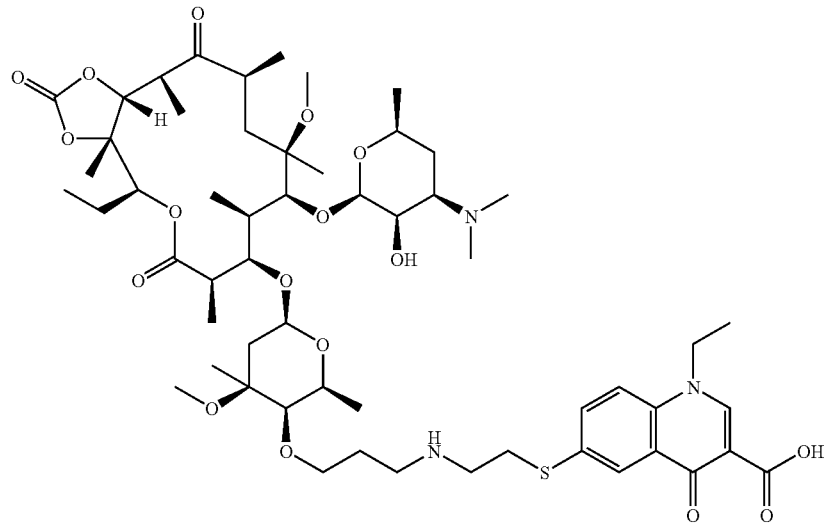

To Example 3a (0.125 g, 0.119 mmol) in dichloromethane (2.5 mL) under argon was added Dess-Martin periodinane (0.095 g, 0.22 mmol). After 3.5 h, the reaction mixture was diluted with dichloromethane, washed with saturated aq sodium hydrogen carbonate, dried, and evaporated to dryness to give the crude aldehyde as a white solid foam. This, material was dissolved in dimethylformamide (1.5 mL) and methanol (1.5 mL) and treated with acetic acid (0.3 mL), Intermediate 3 (0.081 g, 0.2 mmol) sodium acetate (0.024 g) and sodium cyanoborohydride (0.015 g). After 3 h the reaction was evaporated to dryness, and the residue purified by preparative HPLC (acetonitrile/water/0.1% formic acid eluent) to give the title product (0.024 g); $^1$H NMR δ (CDCl$_3$) (inter alia) 1.6 (3H, t), 2.0 (2H, m), 3.05 (2H, m), 3.65 (1H, m), 3.85 (1H, m), 4.4 (2H, q), 4.55(1H, d), 4.6 (1H, s), 4.85 (1H, d), 5.0 (1H, dd), 7.65 (1H, d), 7.85 (1H, d), 8.35 (2H, s), 8.4 (1H, s); ESMS m/z 1106 [M+H]$^+$.

Example 5

4"-O-{3-[3-(3-Carboxy-1-ethyl-4-oxo-1,4-dihydro-quinolin-6-yl)-propylamino]-propyl}-6-O-methyl-erythromycin A bisformate

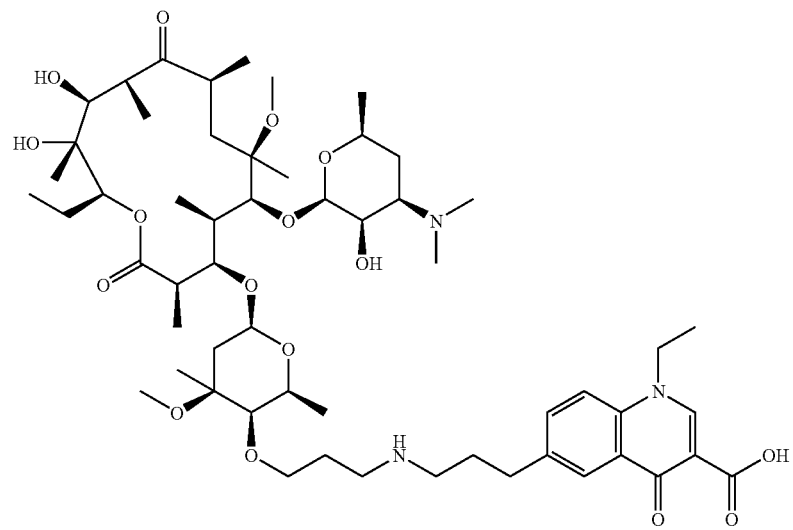

a) 4"-O-(1-imidazol-1-yl-carbonyl)-6-O-methyl-erythromycin A

6-O-Methyl-erythromycin A (30 g, 40.1 mmol) in tetrahydrofuran (100 mL) was treated portionwise with carbonyldiimidazole (16 g, 97 mmol) with ice bath cooling. After 1 h the cooling bath was removed. After a further 48 h, tetrahydrofuran (100 mL) and water (200 mL) were added slowly precipitating the title compound, which was collected by filtration and dried to give the title compound (24.7 g). Extraction of the mother liquors with diethyl ether gave further material (8.5 g) which was precipitated from tetrahydrofuran solution with water to give a further portion of the title compound (3.92 g, total of 28.64 g); ESMS m/z 842 [M+H]$^+$.

b) 4"-O-(Allyloxycarbonyl)-6-O-methyl-erythromycin A

Example 5a (28.64 g, 34 mmol) in dichloromethane (100 mL) was cooled to 0° C. and treated with allyl alcohol (13.6 mL) and DBU (5.23 mL). The reaction was stirred at 0° C. for 2.5 h and at 20° C. for 1.75 h. The reaction mixture was quenched with 3% aq citric acid (100 mL), the phases separated, and the organic phase washed with sat sodium hydrogen carbonate and brine. After drying and evaporation to dryness, the residue was triturated with petroleum ether (bp 40-60° C.) to give the title compound as a solid (25.08 g); ESMS m/z 832 [M+H]$^+$.

c) 4"-O-(Allyloxycarbonyl)-9-dihydro-9-methoxy-2', 11-bis-O-trimethylsilyl-6-O-methyl-9,12-anhydro-erythromycin A

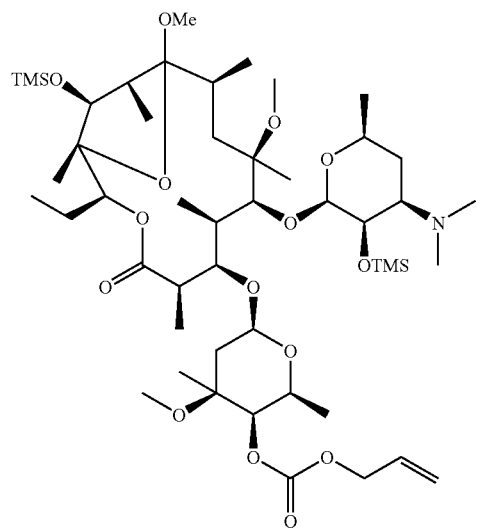

Example 5b (22.29 g, 25.6 mmol) in pyridine (100 mL) was treated with chlorotrimethylsilane (26 mL). The reaction was stirred at 20° C. for 6 h and left at 4° C. for 16 h. The reaction mixture was evaporated to dryness under reduced pressure and the residue taken up in methanol (100 mL) After 80 min at 20° C., the solvent was removed by evaporation under reduced pressure and the residue taken up in ethyl acetate and water the phases were separated, the organic layer dried, and evaporated to dryness under reduced pressure. Toluene (two 500 mL portions) were added and evaporated under reduced pressure to give the crude title compound as a white foam (26.27 g). This material (5.8 g) was purified by chromatography on silica gel eluting with 0-3% 2 M methanolic ammonia in dichloromethane to give the title compound as a white foam (3.0 g); ESMS m/z 990 [M+H]$^+$.

d) 4"-O-Allyl-9-dihydro-9-methoxy-2',11-bis-O-trimethylsilyl-6-O-methyl-9,12-anhydro-erythromycin A Example 5c (3.0 g, 3.03 mmol) in tetrahydrofuran (20 mL) was treated with tetrakis triphenylphosphine palladium (0.1 g) at reflux under argon. After 35 min, t-butyl allyl carbonate (F. Houlihan et al, *Can. J. Chem,* 1985, 63, 153; 1.2 mL) and tetrakis(triphenylphosphine)palladium (0.1 g) were added and the reflux continued for a further 1 h. The reaction was cooled and evaporated to dryness under reduced pressure, and the residue purified by chromatography on silica gel eluting with 0-5% 2 M methanolic ammonia in dichloromethane to give the title product, 1.07 g, as a white foam; ESMS m/z 946 [M+H]$^+$.

e) 9-Dihydro-4"-O-(3-hydroxypropyl)-9-methoxy2', 11-bis-O-trimethylsilyl-6-O-methyl-9,12-anhydro-erythromycin A Example 5d (0.255 g, 0.27 mmol) in tetrahydrofuran (4 mL) under argon was treated with 9-BBN (0.5 M in tetrahydrofuran, 1.6 mL). After 30 min, the reaction was cooled to 0° C. and a precooled mixture of sodium hydroxide (2 M, 0.5 mL) and hydrogen peroxide (27% in water, 0.68 mL) were added. This was stirred at 0° C. for 10 min before addition of cold diethyl ether and water. The phases were separated and the organic phase washed with water and brine. After drying and evaporation under reduced pressure the residue was purified by chromatography on silica gel eluting with 0-10% 2 M methanolic ammonia in dichloromethane to give the title product as a White foam (0.16 g); ESMS m/z 964 [M+H]$^+$.

f) 4"-O-{3-[3-(3-Carboxy-1-ethyl-4-oxo-1,4-dihydro-quinolin-6-yl)-propylamino]-propyl}-6-O-methyl-erythromycin A bisformate To Example 5e (0.16 g, 0.166 mmol) in dichloromethane (5 mL) under argon was added Dess-Martin periodinane (0.085 g, 0.2 mmol). After 1 h, the reaction mixture was diluted with dichloromethane, washed with sat. aq sodium hydrogen carbonate, dried, and evaporated to dryness to give the crude aldehyde as a gum. This material was dissolved in methanol (2.5 mL) and dichloromethane (2.5 mL) and treated with acetic acid (0.25 mL), sodium acetate (0.028 g), 3A molecular sieves (0.3 g), Intermediate 4 (0.0625 g, 0.16 mmol) and sodium cyanoborohydride (0.030 g). After 2 h the reaction was evaporated to dryness, and toluene (5 mL) added and evaporated. The residue was purified by preparative HPLC (acetonitrile/water/0/1% formic acid eluent) and the fractions allowed to stand at 20° C. for 1 h which resulted in loss of protection. A further preparative HPLC (acetonitrile/water/ 0.1% formic acid eluent) purification gave the fitle product (0.034 g); ESMS m/z 1062 [M+H]$^+$.

Example 6

4"-O-{3-[2-(2-Carboxy-1-oxo-6,7-dihydro-1H,5H-pyrido[3,2,1-ij]quinoline-9-yloxy)-ethylamino]-propyl}-6-O-methyl-erythromycin A 11,12-carbonate bisformate

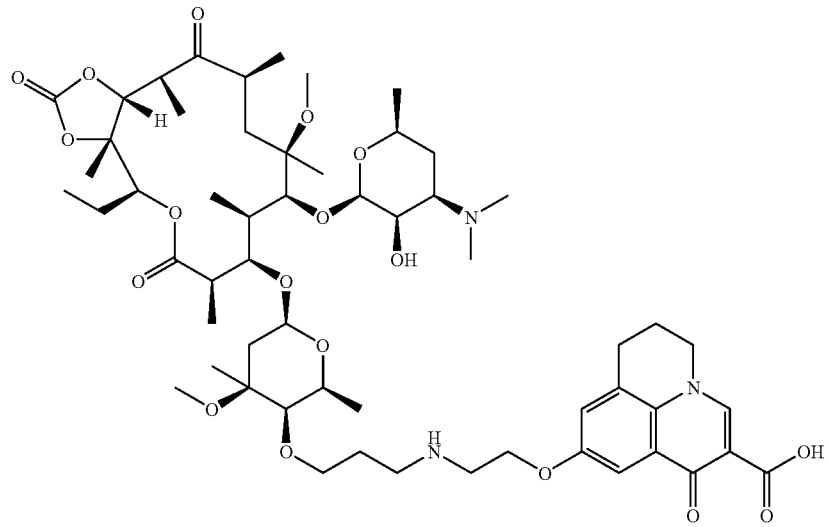

To Example 3a (0.25 g, 0.33 mmol) in dichloromethane (5 mL) under argon was added Dess-Martin periodinane (0.14 g, 0.33 mmol). After 2 h, more Dess-Martin periodinane (0.03 g) was added and the reaction stirred for a further 1.5 h. The reaction mixture was diluted with dichloromethane, washed with saturated. aq sodium hydrogen carbonate, dried, and evaporated to dryness to give the crude aldehyde as a white solid foam. This material (0.042 g, 0.05 mmol) in methanol/DCM (1:1, 2 mL) was added to sodium acetate (0.008 g, 0.1 mmol), acetic acid (0.1 mL), Intermediate 5 (0.02 g, 80% pure, 0.05 mmol), and 3A molecular sieves (0.1 g). The mixture was stirred for 15 min then a solution of sodium cyanoborohydride (0.0063 g, 0.1 mmol) in methanol (0.2 mL) was added and stirring continued for 3 h. The reaction was then filtered, washing well with methanol, and the filtrate evaporated. The residue was purified by preparative reverse phase HPLC (MeCN/H2O/0.1% HCO2H eluent) to give the title compound as a pale yellow solid (0.031 g); ESMS m/z 1102 [M+H]$^+$.

Example 7

4"-O-{3-[2-(3-Carboxy-1-ethyl-4-oxo-1,4-dihydro-quinolin-6-yl)-propylamino]-propyl}-6-O-methyl-11-desoxy-11-(R)-methylamino-erythromycin A 11,12-carbamate formate

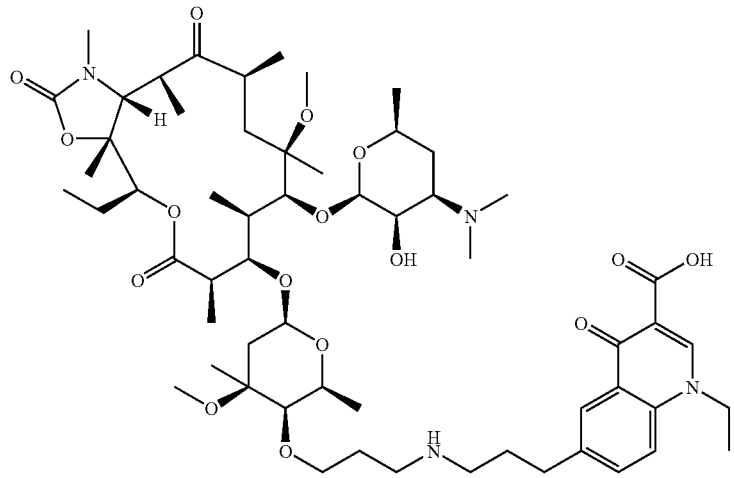

a) 2'-O-Acetyl-4"-O-allyl-6-O-methyl-11-desoxy-11-(R)-methylamino-erythromycin A 11,12-carbamate Intermediate 7 (0.315 g, 0.38 mmol), t-butyl allyl carbonate (0.079 g, 0.5 mmol) and tetrakis(triphenylphosphine)palladium (0.035 g, 0.03 mmol) in THF (10 mL) were refluxed for 4 h. More t-butyl allyl carbonate (0.079 g, 0.5 mmol) was added and refluxing continued for a further 2 h. More t-butyl allyl carbonate (0.04 g, 0.25 mmol) was added and refluxing continued for a further 1.5 h. The mixture was then evaporated to dryness and the residue purified by chromatography on silica gel (40 g). Elutton with 0-4.5% 2 M methanolic ammonia in dichloromethane, gave the title compound (0.294 g); ESMS m/z 869 $[M+H]^+$.

b) 4"-O-Allyl-6-O-methyl-11-desoxy-11-(R)-methylamino-erythromycin A 11,12-carbamate Example 7a (0.27 g, 0.31 mmol) in methanol (10 mL) was heated at 60° C. for 8.5 h, 45° C. for 15 h, and 60° C. for 3 h. The mixture was then evaporated to dryness to give the title compound as a white solid (0.244 g); ESMS m/z 827 $[M+H]^+$.

c) 2'-O,3'-N-bis(Benzyloxycarbonyl)-3'-N-desmethyl-4"-O-allyl-6-O-methyl-11-desoxy-11-(R)-methylamino-erythromycin A 11,12-carbamate Example 7b (0.24 g, 0.29 mmol) and sodium hydrogen carbonate (0.4 g) in benzyl chloroformate (2 mL) were heated at 60° C. for 3 h. After cooling the mixture was purified by chromatography on silica gel (50 g). Elution with 0-50% ethyl acetate in petroleum ether gave the title compound as a white solid (0.272 g); ESMS m/z 1098 $[M+NH_4]^+$.

d) 2'-O,3'-N-bis(Benzyloxycarbonyl)-3'-N-desmethyl-4"-O-(3-hydroxypropyl)-6-O-methyl-11-desoxy-11-(R)-methylamino-erythromycin A 11,12-carbamate Example 7c (0.27 g, 0.25 mmol) in THF (8 mL) was treated with 9-borabicyclo[3.3.1]nonane (0.5 M in THF, 1.5 mL, 0.75 mmol). After 4 h more 9-borabicyclo[3.3.1]nonane (0.5 M in THF, 0.5 mL, 0.25 mmol) was added. Further 1 h then more 9-borabicyclo[3.3.1]nonane (0.5 M in THF, 1 mL, 0.5 mmol) was added. After 1 h more the solution was cooled in an ice bath then pre-mixed hydrogen peroxide (30% aq, 1.7 mL, 15 mmol) in sodium hydroxide (2 N, 2.5 mL, 5 mmol) was added. The cooling bath was removed and the mixture stirred for 0.5 h. The reaction was diluted with water and extracted with ethyl acetate (×3). The combined organic extracts were washed with brine, dried, and evaporated to give the crude product. This was purified by chromatography on silica gel (40 g), eluting with 30-80% ethyl acetate in petroleum ether, to give the title compound as a white solid (0.139 g); ESMS m/z 1116 $[M+NH_4]^+$.

e) 4"-O-(3-Hydroxypropyl)-6-O-methyl-11-desoxy-11-(R)-methylamino-erythromycin A 11,12-carbamate Example 7d (0.137 g, 0.125 mmol) was dissolved in ethanol (4 mL) and 1,4-dioxane (6 mL), and hydrogenated over 10% palladium on charcoal (50% aq paste, 0.06 g) for 6.5 h. Formaldehyde (37% aq, 0.3 mL), pH 4.5 acetate buffer (0.3 mL) and more catalyst (0.05 g) were then added, and the mixture hydrogenated for 16 h. The mixture was then filtered, washing well with ethanol and 1,4-dioxane. The filtrate was evaporated, and the residue purified by chromatography on silica gel (5 g). Elution with 0-6% 2 M methanolic ammonia in dichloromethane, gave the title compound as a white foam (0.083 g); ESMS m/z 845 $[M+H]^+$.

f) 4"-O-(3-Oxopropyl)-6-O-methyl-11-desoxy-11-(R)-methylamino-erythromycin A 11,12-carbamate To Example 7e (0.082 g, 0.097 mmol) in DCM (3 mL) was added Dess-Martin periodinane (0.047 g, 0.11 mmol). The reaction was stirred for 1.75 h, then more oxidant (0.018 g) added. After a further 1.5 h, the reaction was diluted with DCM, washed with aq sodium hydrogen carbonate, dried and evaporated to give the crude title compound as a white foam (0.086 g), which was used without purification; ESMS m/z 843 $[M+H]^+$.

g) 4"-O-{3-[2-(3-Carboxy-1-ethyl-4-oxo-1,4-dihydro-quinolin-6-yl)-propylamino]-propyl}-6-O-methyl-11-desoxy-11-(R)-methylamino-erythromycin A 11,12-carbamate formate Example 7f (0.082 g, 0.097 mmol) in methanol/DCM (1:1, 4 mL) was added to sodium acetate (0.0164 g, 0.2 mmol), acetic acid (0.2 mL), Intermediate 4 (0.0274 g, 0.1 mmol), and 3A molecular sieves (0.2 g). The mixture was stirred for 20 min then a solution of sodium cyanoborohydride (0.0126 g, 0.2 mmol) in methanol (0.3 mL) was added and stirring continued for 16 h. The reaction was then filtered, washing well with methanol and DCM, and the filtrate evaporated. The residue was purified by preparative reverse phase HPLC (MeCN/$H_2O$/0.1% $HCO_2H$ eluent) to give the title compound as an off-white powder (0.038 g, 35%); ESMS m/z 1101 $[M+H]^+$.

Example 8

4"-O-{3-[3-(3-Carboxy-1-ethyl-4-oxo-1,4-dihydro-quinolin-6-yl)-propylamino]-propyl}-6-O-methyl-11-desoxy-11-(R)-amino-erythromycin A 11,12-carbamate formate

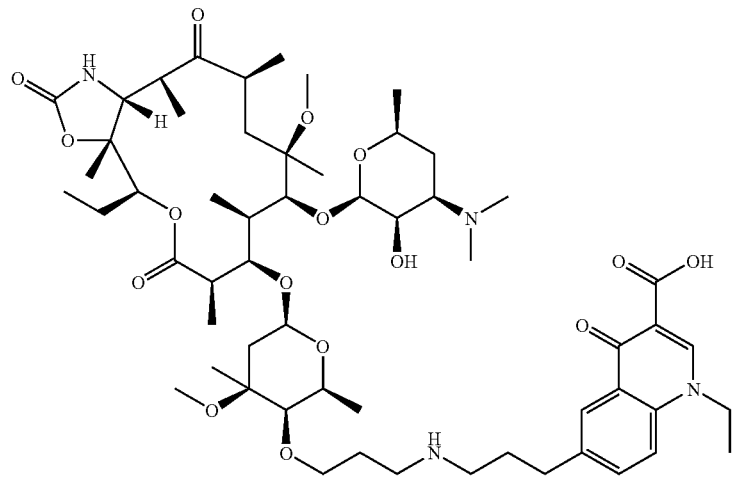

a) 2'-O,3'-N-bis(Benzyloxycarbonyl)-3'-N-desmethyl-4"-O-[3-(tert-butyldimethylsilyl-oxy)propyl]-6-O-methyl-erythromycin A 11,12-carbonate Example 2a (1.85 g, 1.71 mmol) in DMF (10 mL) was treated sequentially with imidazole (0.128 g, 1.88 mmol) and tert-butyldimethylsilyl chloride (0.283 g, 1.88 mmol). Mixture stirred for 20 h then evaporated. Water was added and the mixture extracted with diethyl ether. The combined organic extracts were washed with brine, dried, and evaporated. The residue was purified by chromatography on silica gel (100 g), eluting with 12-42% ethyl acetate in petroleum ether, to give the title compound as a white foam (1.923 g); ESMS m/z 1217 [M+NH$_4$]$^+$.

b) 2'-O,3'-N-bis(Benzyloxycarbonyl)-3'-N-desmethyl-4"-O-[3-(tert-butyldimethylsilyl-oxy)propyl]-6-O-methyl-11-desoxy-11-(R)-amino-erythromycin A 11,12-carbamate Example 8a (1.9 g, 1.58 mmol), carbonyldiimidazole (1.28 g, 7.2 mmol), imidazole (0.01 g) and DBU (0.08 g, 0.52 mmol) were dissolved in THF (10 mL), heated to 40° C. and stirred for 17 h. Further portions of carbonyldiimidazole and DBU were added, and reaction heated at 60° C. for 6 h then 50° C. for 16 h. The mixture was then cooled in an ice bath and ammonia gas bubbled in for 8 h. The reaction was then stored in the fridge for 14 h. Argon was then bubbled through the mixture before the addition of potassium tert-butoxide (1 M in THF, 1.74 mL, 1.74 mmol). After 5 h at room temperature more potassium tert-butoxide (1 M in THF, 1 mL, 1 mmol) was added. Further 2 h then more potassium tert-butoxide (1 M in THF, 0.5 mL, 0.5 mmol) added. The mixture was then stirred for 64 h. Aqueous sodium hydrogen carbonate was then added and the mixture extracted with ethyl acetate. The combined organic extracts were washed with brine, dried, and evaporated. The residue was purified by chromatography on silica gel (100 g), eluting with 20-52% ethyl acetate in petroleum ether, to give the title compound as a white foam (1.3 g); ESMS m/z 1216 [M+NH$_4$]$^+$.

c) 4"-O-[3-(tert-butyldimethylsilyl-oxy)propyl]-6-O-methyl-11-desoxy-11-(R)-amino-erythromycin A 11,12-carbamate Example 8b (1.4 g, 1.17 mmol) was dissolved in methanol (10 mL) and 1,4-dioxane (15 mL), and hydrogenated over 10% palladium on charcoal (50% aq paste, 0.4 g) for 6 h. Formaldehyde (37% aq, 4 mL), pH 4.5 acetate buffer (4 mL) and more catalyst (0.2 g) were then added, and the mixture, hydrogenated for 24 h. The mixture was then filtered, washing well with methanol and 1,4-dioxane. The filtrate was evaporated, and the residue purified by chromatography on silica gel (100 g). Elution with 0-7% 2 M methanolic ammonia in dichloromethane, gave the title compound as a white foam (0.969 g); ESMS m/z 945 [M+H]$^+$.

d) 4"-O-(3-Hydroxypropyl)-6-O-methyl-11-desoxy-11-(R)-aminoerythromycin A 11,12-carbamate Example 8c (0.17 g, 0.18 mmol) in THF (4 mL) and acetic acid (0.023 mL, 0.4 mmol) was treated with tetrabutylammonium fluoride (1 M in THF, 0.4 mL, 0.4 mmol). The mixture was stirred at 35° C. for 72 h, then evaporated to dryness, and the residue purified by chromatography on silica gel (40 g). Elution with 0-11% 2 M methanolic ammonia in dichloromethane, gave the title compound as a white foam (0.15 g); ESMS m/z 831 [M+H]$^+$.

e) 4"-O-(3-Oxopropyl)-6-O-methyl-11-desoxy-11-(R)-aminoerythromycin A 11,12-carbamate To Example 8d (0.085 g, 0.1 mmol) in DCM (2 mL) was added Dess-Martin periodinane (0.051 g, 0.12 mmol) in DCM (1 mL). Stirred for 1.3 h, then diluted with DCM, washed with aq sodium hydrogen carbonate, dried and evaporated to give the crude title compound as a white foam (0.097 g), which was used without purification; ESMS m/z 829 [M+H]$^+$.

f) 4"-O-{3-[3-(3-Carboxy-1-ethyl-4-oxo-1,4-dihydro-quinolin-6-yl)-propylamino]-propyl}-6-O-methyl-11-desoxy-11-(R)-amino-erythromycin A 11,12-carbamate formate Example 8e (0.082 g, 0.1 mmol) in methanol/DCM (1:1, 4 mL) was added to sodium acetate (0.025 g, 0.3 mmol), acetic acid (0.2 mL), Intermediate 4 (0.043 g, 0.11 mmol), and 3A molecular sieves (0.2 g). The mixture was stirred for 30 min then a solution of sodium cyanoborohydride (0.0126 g, 0.2 mmol) in methanol (0.3 mL) was added and stirring continued for 2.5 h. The reaction was then filtered, washing well with methanol and DCM, and the filtrate evaporated. The residue was purified by preparative reverse phase HPLC (MeCN/H$_2$O/0.1% HCO$_2$H eluent) to give the title compound as a pale yellow solid (0.054 g, 46%); ESMS m/z 1087 [M+H]$^+$.

Example 9

4"-O-{3-[3-(3-Carboxy-1-ethyl-4-oxo-1,4-dihydro-quinolin-6-yl)propylamino]-propyl}-6-O-methyl-erythromycin A 11,12-carbonate formate

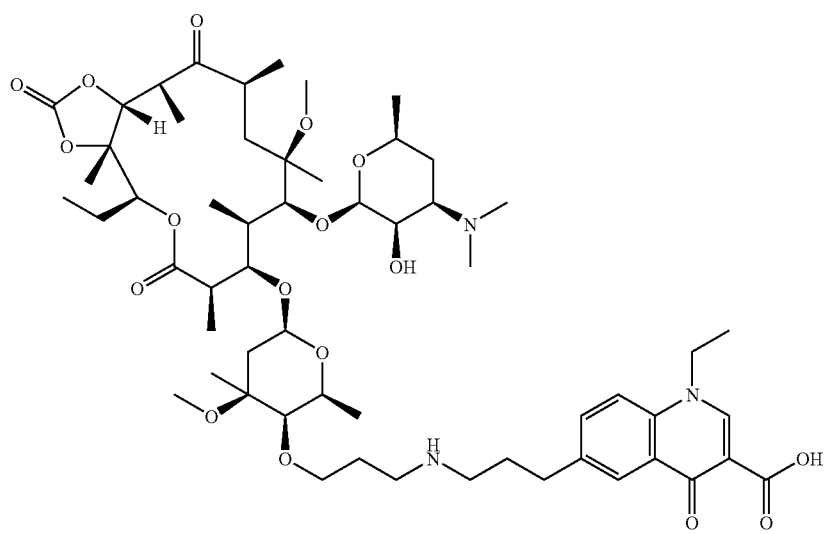

Example 10

4"-O-{3-[2-(3-Carboxy-7-chloro-1-cyclopropyl-4-oxo-1,4-dihydro-quinolin-6-ylamino)ethylamino]-propyl}-6-O-methyl-erythromycin A 11,12-carbonate formate

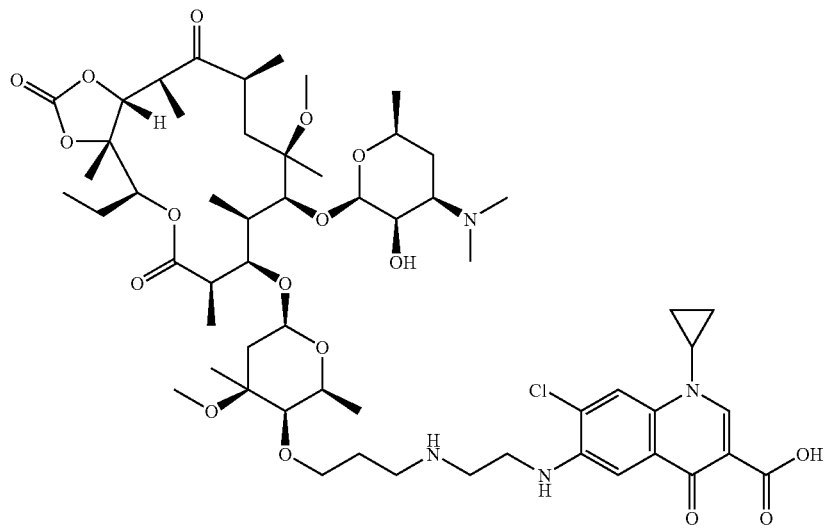

Example 11

4''-O-{3-[2-(3-Carboxy-1-cyclopropyl-6-fluoro-4-oxo-1,4-dihydro-quinolin-7-ylamino)ethylamino]-propyl}-6-O-methyl-erythromycin A 11,12-carbonate formate

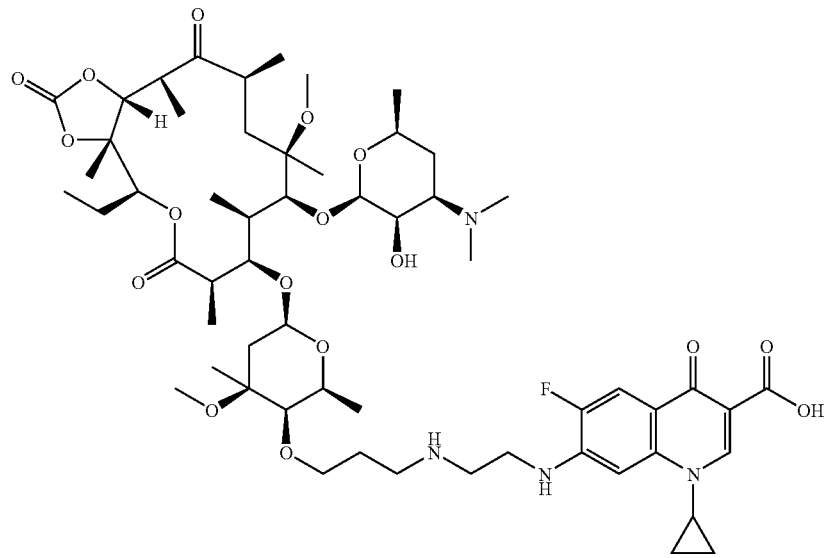

Example 12

4''-O-{3-[2-(3-Carboxy-1-ethyl-6-fluoro-4-oxo-1,4-dihydro-[1,8]naphthyridin-7-ylamino)ethylamino]-propyl}-6-O-methyl-erythromycin A 11,12-carbonate formate

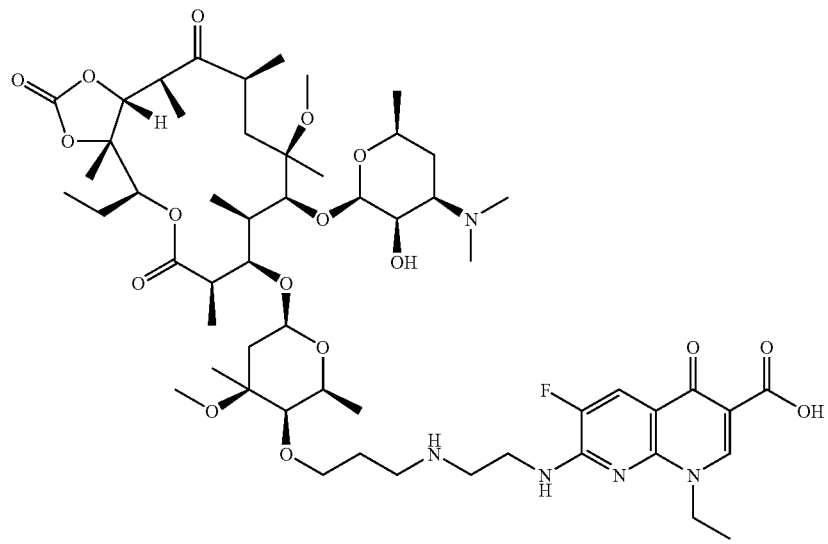

To 4''-O-(3-hydroxypropyl)-6-O-methylerythromycin A 11,12-carbonate (0.883 g, 1.06 mmol) in dichloromethane (20 mL) under argon was added Dess-Martin periodinane (0.495 g, 1.17 mmol). After 3 h, more Dess-Martin periodinane (0.1 g, 0.24 mmol) was added, and after 1.5 h more Dess-Martin periodinane (0.11 g, 0.26 mmol) was added. The mixture was stirred for a further 35 min then diluted with dichloromethane, washed with saturated aqueous sodium hydrogen carbonate, dried, filtered, and concentrated in vacuo to give the crude aldehyde as a white solid foam. This material was dissolved in methanol (20 mL) and dichloromethane (20 mL), then split into four equal portions which were used in the general procedure for reductive amination.

General Procedure for Reductive Amination

To the solution of aldehyde in methanol (5 mL) and dichloromethane (5 mL) was added sodium acetate (0.044 g, 0.54 mmol), acetic acid (0.5 mL), 3A molecular sieves (0.5 g), and the amine (0.26 mmol). The mixture was stirred for 10 min then a solution of sodium cyanoborohydride (0.033 g, 0.5 mmol) in methanol (0.5 mL) was added and stirring continued for 20 h. The reaction was then filtered through Celite, and concentrated in vacuo to give a residue which was purified by preparative reverse phase HPLC (MeCN/H$_2$O/0.1% HCO$_2$H eluent), then further purified by chromatography (silica gel, 0-20% 2 M methanolic ammonia in dichloromethane) to give the title compound.

| Amine intermediate | Example no. | Product mass (g) | ESMS m/z [M + H]$^+$ |
|---|---|---|---|
| 4 | 9 | 0.096 | 1088 |
| 1 | 10 | 0.111 | 1135 |

-continued

| Amine intermediate | Example no. | Product mass (g) | ESMS m/z [M + H]$^+$ |
|---|---|---|---|
| 7-(2-aminoethylamino)-1-cyclopropyl-6-fluoro-4-oxo-1,4-dihydro-quinoline-3-carboxylic acid | 11 | 0.103 | 1119 |
| 6 | 12 | 0.084 | 1108 |

Example 13

4"-O-(3-{[3-(3-Carboxy-1-ethyl-4-oxo-1,4-dihydro-quinolin-6-yl)propyl]-methylamino}-propyl)-6-O-methyl-erythromycin A 11,12-carbonate formate

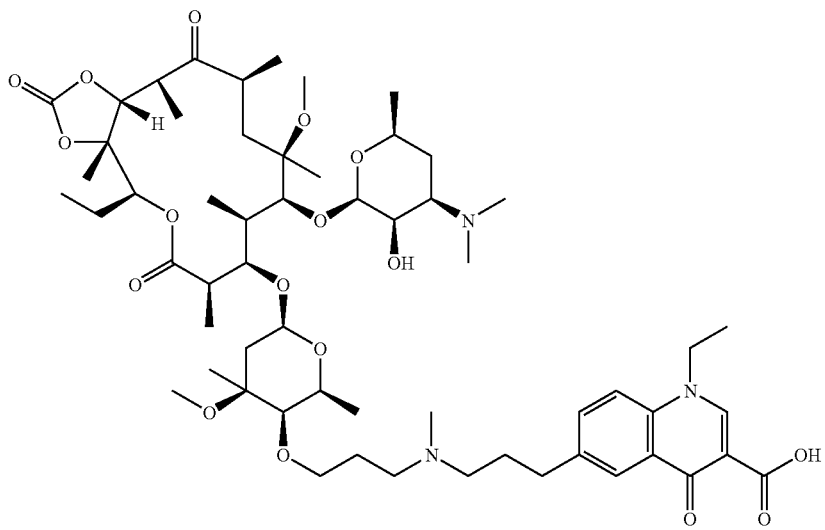

Example 14

4"-O-(3-{[2-(3-Carboxy-7-chloro-1-cyclopropyl-4-oxo-1,4-dihydro-quinolin-6-ylamino)ethyl]-methylamino}-propyl)-6-O-methyl-erythromycin A 11,12-carbonate

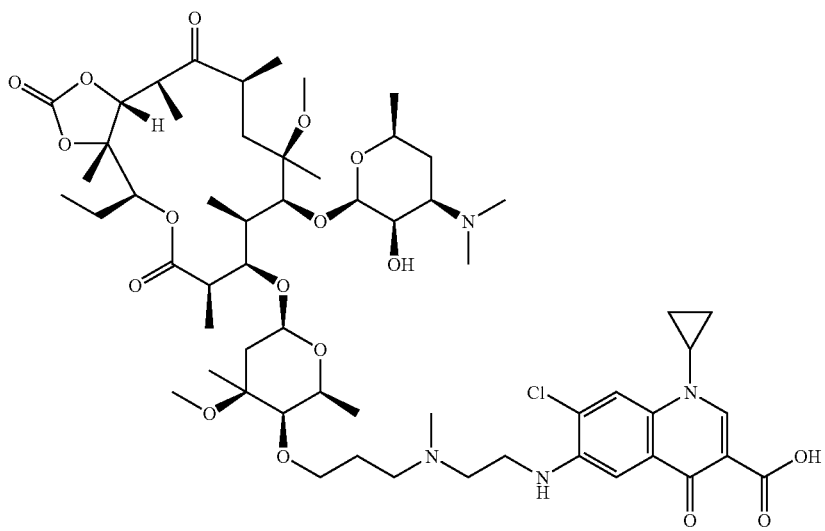

Example 15

4"-O-(3-{[2-(3-Carboxy-1-ethyl-6-fluoro-4-oxo-1,4-dihydro-[1,8naphthyridin-7-ylamino)ethyl]-methylamino}-propyl)-6-O-methyl-erythromycin A 11,12-carbonate

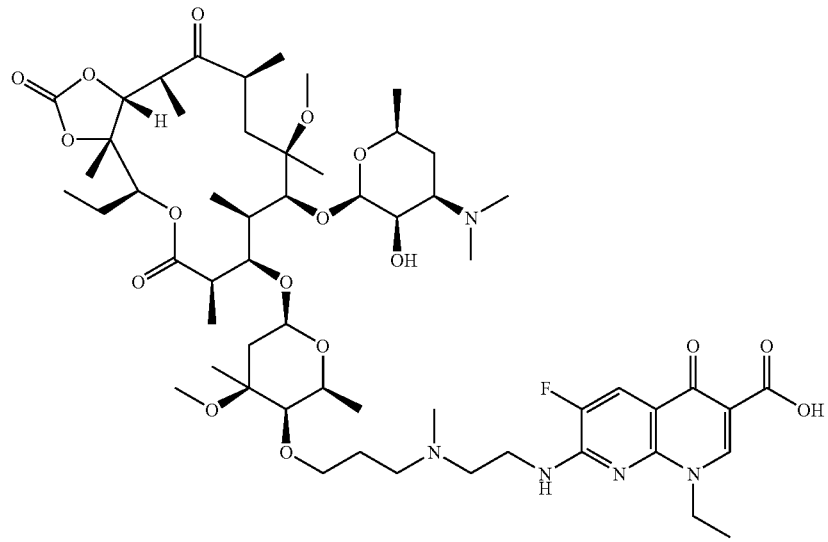

General Procedure for N-Methylation

To a solution of amine starting material (0.072 mmol) as tabulated below in chloroform (2 mL) was added formic acid (0.005 mL, 0.144 mmol), and formaldehyde (37% by weight in water) (0.011 mL, 0.144 mmol). The mixture was heated to 60° C. for 3 h then concentrated in vacuo to give a residue which was purified by chromatography (silica gel, 0-20% 2 M methanolic ammonia in dichloromethane) or by preparative reverse phase HPLC (MeCN/H$_2$O/0.1% HCO$_2$H eluent) to give the title compound.

| Starting material | Example no. | ESMS m/z [M + H]$^+$ |
|---|---|---|
| Example 9 | 13 | 1102 |
| Example 10 | 14 | 1149 |
| Example 12 | 15 | 1122 |

Example 16

4"-O-{2-[3-(3-Carboxy-1-ethyl-4-oxo-1,4-dihydroquinolin-6-yl)propylamino]ethyl}azithromycin 11,12-carbonate

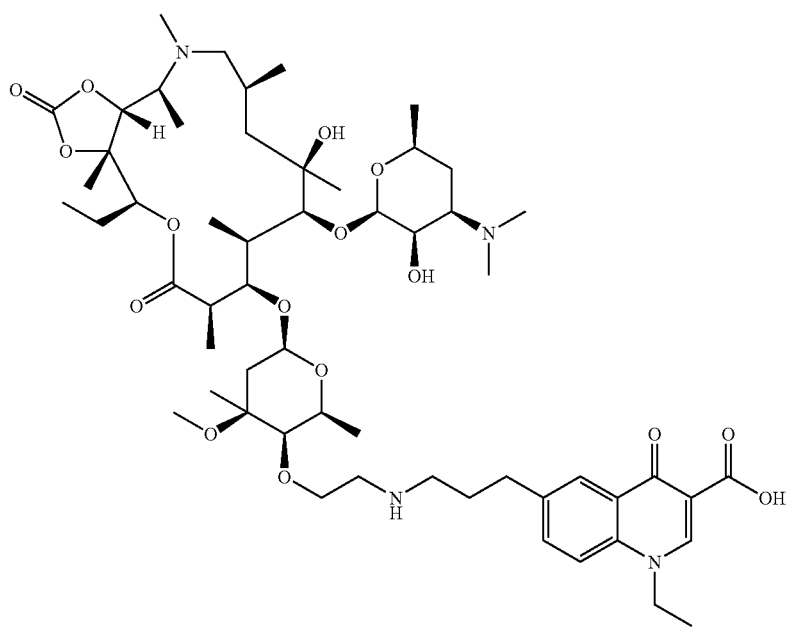

a) 2'-O-Acetyl-azithromycin 11,12-carbonate

To a suspension of azithromycin 11,12-carbonate (B. A. Jones et al., *Tet. Lett.*, 1993, 34, 4913; 100 g, 0.13 mol) and sodium hydrogen carbonate (44 g, 0.52 mol) in dichloromethane (400 mL) was added dropwise acetic anhydride (20.4 mL, 0.2 mol). After stirring overnight the mixture was diluted with water (400 mL) and the organic layer separated, dried and evaporated to yield the title compound as a white solid; ESMS m/z 818 (MH$^+$).

b) 2'-O-Acetyl-4''-O-allyl-azithromycin 11,12-carbonate

To a solution of Example 16a (0.408 g, 0.5 mmol) in dry THF (4 mL) and tetrakis(triphenyphosphine)palladium (0.057 mg, 0.05 mmol) was added allyl t-butyl carbonate (0.300 g, 1.89 mmol). After heating at reflux under argon for 8 h the mixture was cooled and the solvent evaporated. Chromatography of the residue over silica gel eluting with dichloromethane containing an increasing concentration of methanol (0-1%) gave the title compound as a pale yellow gum; ESMS m/z 857 (MH$^+$).

c) 2'-O-Acetyl-4''-O-(2-oxoethoxy)azithromycin 11,12-carbonate

To a cooled solution of Example 16b (0.20 g, 0.23 mmol) in THF (1 mL) and water (1 mL) was added osmium tetraoxide (15 μL of a 4% solution in water). After 5 mins solid sodium periodate (0.21 g, 1 mmol) was added in one portion and the resultant mixture stirred at room temperature for 4 h. Sodium hydrogen sulfite (0.19 g, 1 mmol) was added and the organic material extracted with ethyl acetate (2×15 mL). The combined organic fractions were dried and evaporated to yield the title compound as a brown gum; ESMS m/z 877 (MNH$_4^+$).

d) 4''-O-{2-[3-(3-Carboxy-1-ethyl-4-oxo-1,4-dihydro-quinolin-6-yl)propylamino]ethyl}azithromycin 11,12-carbonate A solution of Example 16c (0.054 g, 0.063 mmol), Intermediate 4 (0.05 g, 0.127 mmol) and sodium acetate (0.011 g, 0.127 mmol) in 1% acetic acid/methanol (2 mL) was stirred for 0.5 h at room temperature. Sodium cyanoborohydride (0.016 mg, 0.25 mmol) was added. After 16 h the mixture was concentrated and purified by reverse phase liquid chromatography to yield the title compound as a white solid; ESMS m/z 1076 (MH$^+$).

Example 17

4''-O-{2-[2-(3-Carboxy-1-ethyl-4-oxo-1,4-dihydro-quinolin-6-ylsulfanyl)ethylamino]ethyl}azithromycin tris trifluoroacetate

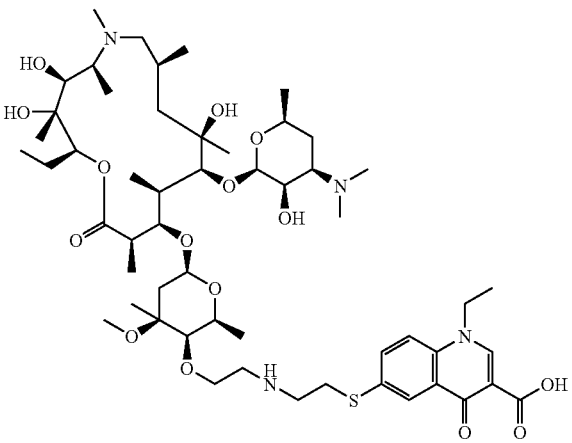

a) 2'-O-Acetyl-4''-O-{2-[2-(3-carboxy-1-ethyl-4-oxo-1,4-dihydro-quinolin-6-ylsulfanyl)ethylamino]ethyl}azithromycin 11,12-carbonate Using a similar procedure to that described in Example 16d, Example 16c (0.055 g, 0.063 mmol) and Intermediate 3 (0.030 g, 0.95 mmol) gave the title compound as a white solid; ESMS m/z 1136 (MH$^+$).

b) 4''-O-{2-[2-(3-Carboxy-1-ethyl-4-oxo-1,4-dihydro-quinolin-6-ylsulfanyl)ethylamino]ethyl}azithromycin tris trifluoroacetate A solution of Example 17a in methanol (2 mL) containing sodium hydrogen carbonate (0.010 g, 0.12 mmol) was stirred at 50° C. After 4 h the mixture was cooled, filtered and the solvent evaporated to yield the crude product. Purification by reverse phase liquid chromatography gave the title compound as a colorless gum; ESMS m/z 1094 (MH$^+$).

Example 18

4''-O-{2-[2-(3-Carboxy-1-ethyl-6-fluoro-4-oxo-1,4-dihydro-[1,8]naphthyridin-7-ylamino)ethyl]-amino}-ethyl}-6-O-methyl-erythromycin A monoformate

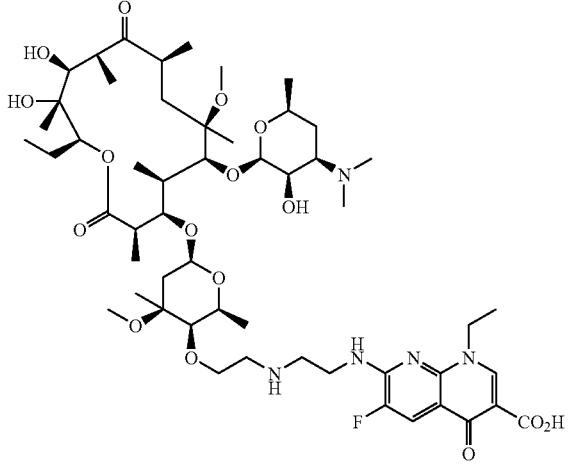

a) 9-Dihydro-9-methoxy-4"-O-2-oxoethyl-2',11-bis-O-trimethylsilyl-6-O-methyl-9,12-anhydro-erythromycin A To Example 5d (0.6 g, 0.64 mmol) in THF (2.5 mL) and water (2.5 mL) under argon was added osmium tetroxide (4% solution in water, 0.04 mL). After 5 min sodium periodate (0.535 g, 2.5 mmol) was added. After stirring for 4.5 h, the reaction was diluted with ethyl acetate (20 mL) and washed with sat. aq. sodium thiosulfate (5 mL) and brine (5 mL). After drying with magnesium sulfate, the solution was evaporated to give the title material as a white foam, (0.62 g); ESMS m/z 966 $[M+H_2O+H]^+$.

b) 4"-O-{2-[2-(3-Carboxy-1-ethyl-6-fluoro-4-oxo-1,4-dihydro-[1,8]naphthyridin-7-ylamino)ethyl]-amino}-ethyl}-6-O-methyl-erythromycin A monoformate To Example 18a (0.1 g, 0.1 mmol) in methanol/DCM (1:1, 3 mL) was added to sodium acetate (0.025 g, 0.3 mmol), acetic acid (0.15 mL), Intermediate 6 (0.041 g, 0.01 mmol), and 3A molecular sieves (0.2 g). The mixture was stirred for 45 min then a solution of sodium cyanoborohydride (0.0128 g, 0.2 mmol) in methanol (0.8 mL) was added and stirring continued for 3 h. The reaction was then filtered, washing well with methanol, and the combined filtrates evaporated. The residue was dissolved in acetonitrile (20 mL), and 1% aq. Formic acid (15 mL) for 10 min at 20° C. before evaporation to dryness. The crude product was purified by preparative reverse phase HPLC (MeCN/H2O/0.1% HCO2H eluent) to give the title compound as a yellow foam (0.037 g); ESMS m/z 1068 $[M+H]^+$.

Example 19

4"-O-{2-[2-(3-Carboxy-1-ethyl-6-fluoro-4-oxo-1,4-dihydro-[1,8]naphthyridin-7-ylamino)ethyl]-methylamino}-ethyl}-6-O-methyl-erythromycin A

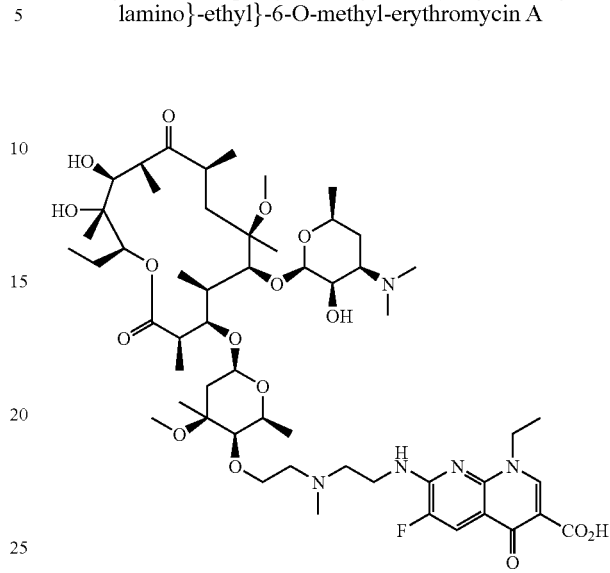

To a solution of Example 18 (0.033 g) in chloroform (1 mL) was added formic acid (0.005 mL, 0.144 mmol), and formaldehyde (37% by weight in water) (0.005 mL, 0.144 mmol). The mixture was heated to 60° C. for 3 h when further 0.005 mL portions of the reagents were added. After a further 1.5 h heating the reaction mixture was concentrated in vacuo to give a residue which was purified by preparative reverse phase HPLC (MeCN/H2O/0.1% HCO2H eluent) to give the title compound, (0.016 g). ESMS m/z 1082 $[M+H]^+$.

Example 20

4"-O-{3-[3-(3-Carboxy-1-ethyl-4-oxo-1,4-dihydro-quinolin-6-yl)-propoxy]-propyl}-6-O-methyl-erythromycin A monoformate

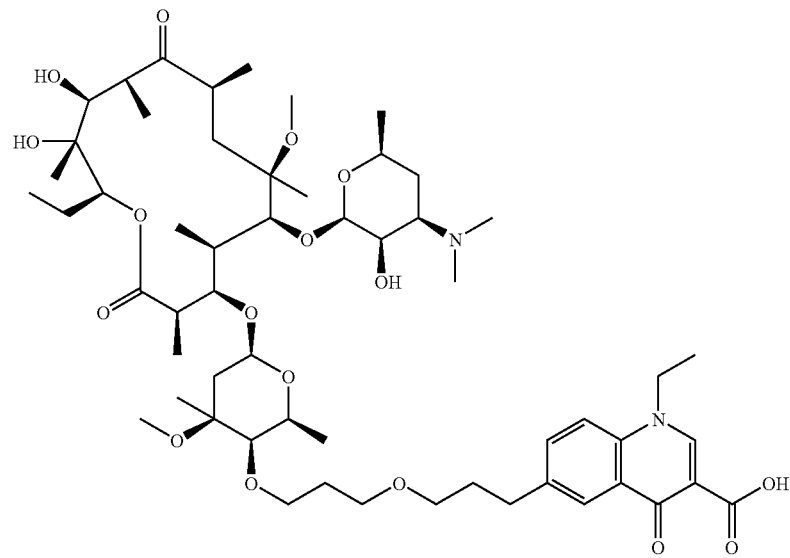

a) 4"-O-{3-[3-(3-Carboxy-1-ethyl-4-oxo-1,4-dihydro-quinolin-6-yl)-propoxy]-prop-1-enyl}-6-O-methyl-erythromycin A ethyl ester To Example 5e (0.12 g, 0.125 mmol) and Intermediate 8 (0.1 g) in THF (2 mL) under argon was added tetrakis(triphenylphosphine)palladium (0.007 g). The reaction was heated to reflux for 15 min after which further Intermediate 8 (0.1 g) and tetrakis(triphenylphosphine)palladium (0.007 g) were added. After a further 40 min reflux, further Intermediate 8 (0.075 g) and tetrakis(triphenylphosphine)palladium (0.007 g) were added. The reaction was refluxed for a further 35 min cooled and evaporated to dryness. The residue was taken up in acetonitrile/0.2M aq. formic acid (50 mL, 50:50) and left at 20° C. for 20 h. After evaporation to dryness, the residue was purified chromatography over silica gel eluting with 0-10% 2M methanolic ammonia in dichloromethane to yield the title compound as a gum (0.175 g); ESMS m/z 1089 $[M+H]^+$.

b) 4"-O-{3-[3-(3-Carboxy-1-ethyl-4-oxo-1,4-dihydro-quinolin-6-yl)-propoxy]-propyl}-6-O-methyl-erythromycin A ethyl ester Example 20a (0.175 g), in ethanol was hydrogenated at 20° C. and 1 atm over 10% Pd/C (0.05 g) for 3 h. The reaction was filtered, and the filtrate evaporated to give the title product, (0.175 g) as a gum, ESMS m/z 1091 $[M+H]^+$.

c) 4"-O-{3-[3-(3-Carboxy-1-ethyl-4-oxo-1,4-dihydro-quinolin-6-yl)-propoxy]-propyl}-6-O-methyl-erythromycin A Example 20b (0.175 g), in 1,4dioxan (5 mL) under argon was treated with water (1 mL) containing lithium hydroxide (0.012 g). After stirring for 75 min, the reaction mixture was evaporated to low volume, and the residue taken up in water and solid $CO_2$ added. After evaporation to dryness, the residue was purified by preparative reverse phase HPLC (MeCN/$H_2O$/0.1% $HCO_2H$ eluent) to give the title compound, (0.036 g) ESMS m/z 1063 $[M+H]^+$.

Example 21

4"-O-{3-[2-(3-Carboxy-1-ethyl-6-fluoro-4-oxo-1,4-dihydro-[1,8]naphthyridin-7-ylamino)-ethylamino]-propyl}-6-O-methyl-11-desoxy-11-(R)-amino-erythromycin A 11,12-carbamate formate

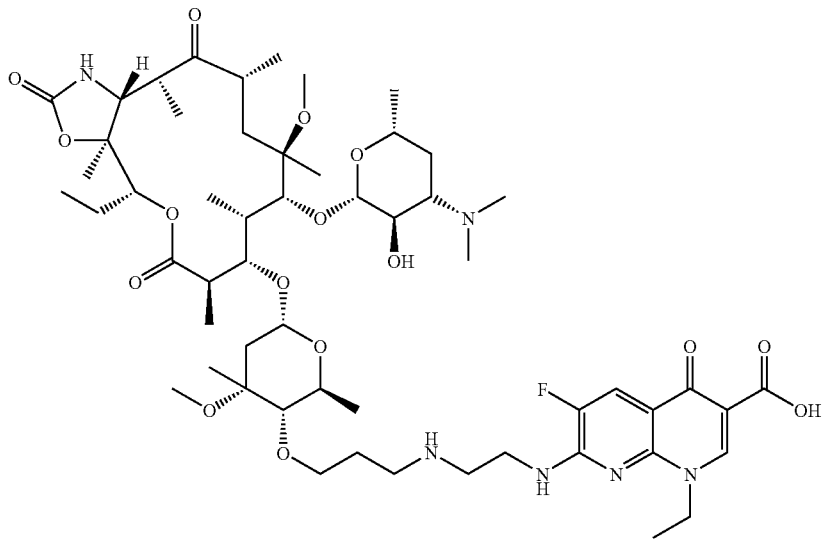

Example 22
4"-O-{3-[2-(2-Carboxy-1-oxo-6,7-dihydro-1H,5H-pyrido[3,2,1-ij]quinolin-9-yloxy)-ethylamino]-propyl}-6-O-methyl-11-desoxy-11-(R)-amino-erythromycin A 11,12-carbamate formate
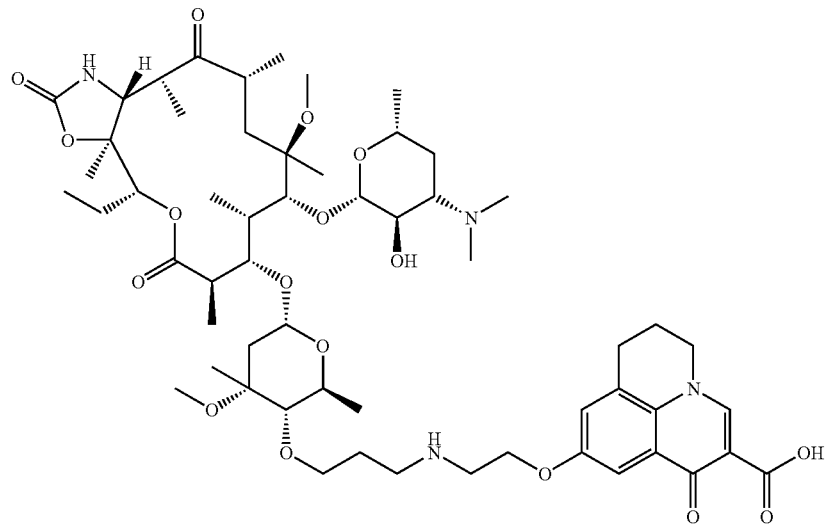
Example 23
4"-O-{3-[3-(3-Carboxy-1-ethyl-5-methyl-4-oxo-1,4-dihydro-quinolin-6-yl)-propylamino]-propyl}-6-O-methyl-11-desoxy-11-(R)-amino-erythromycin A 11,12-carbamate formate
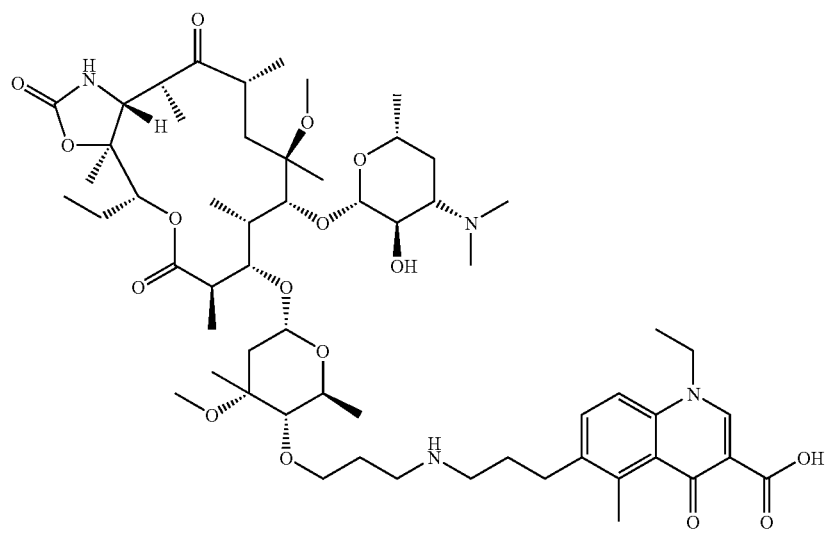

Example 24
4"-O-{3-[3-(3-Carboxy-1-ethyl-4-oxo-1,4-dihydro-6-[1,8]naphthryidinyl)-propylamino]-propyl}-6-O-methyl-11-desoxy-11-(R)-amino-erythromycin A 11,12-carbamate formate
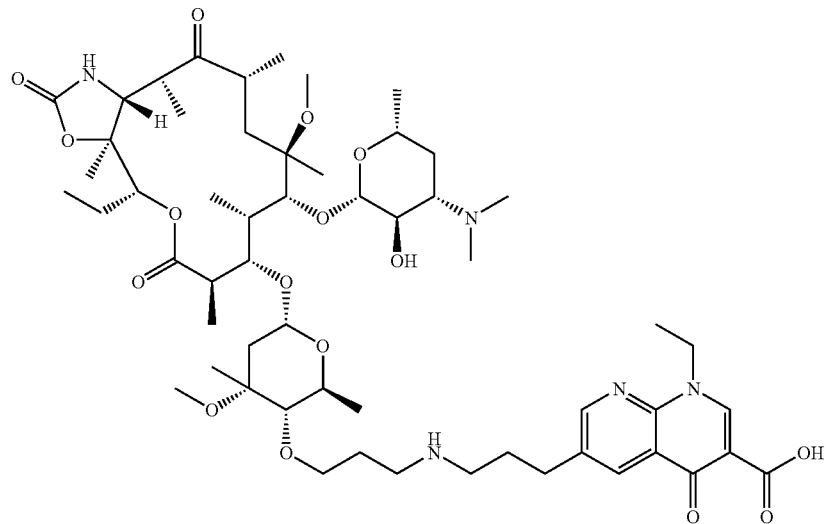
Example 25
4"-O-{3-[3-(2-Carboxy-1-oxo-6,7-dihydro-1H,5H-pyrido[3,2,1-ij]quinolin-9-yl)-propylamino]-propyl}-6-O-methyl-11-desoxy-11-(R)-amino-erythromycin A 11,12-carbamate formate
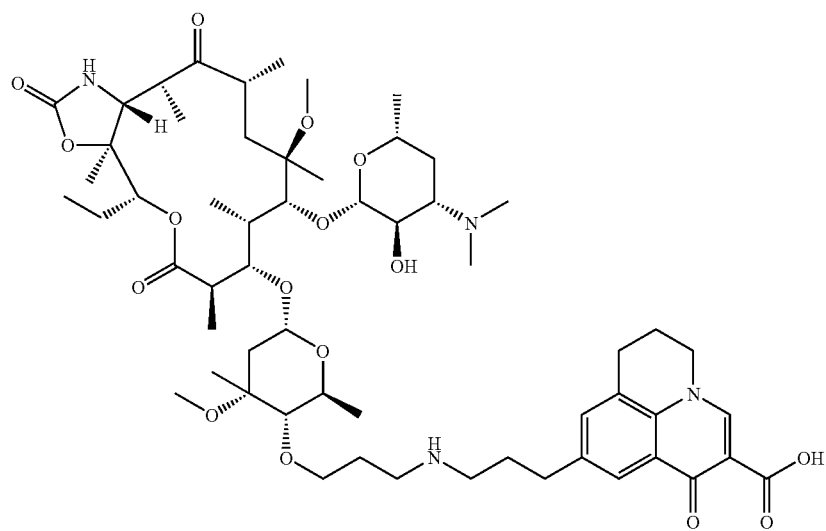

Example 26

4"-O-{3-[2-(3-Carboxy-1-ethyl-4-oxo-4-H-quinolizin-7-ylamino)-ethylamino]-propyl}-6-O-methyl-11-desoxy-11-(R)-amino-erythromycin A 11,12-carbamate formate

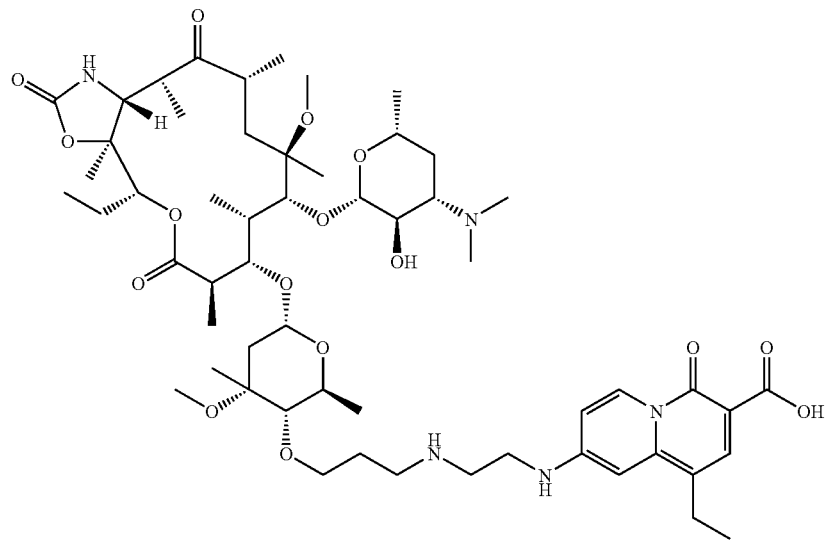

Using the method of Example 8f the amino acids tabulated below were converted to the title compounds. Purification was by chromatography (silica gel, 0-20% 2 M methanolic ammonia in dichloromethane) and/or by preparative reverse phase HPLC (MeCN/H$_2$O/0.1% HCO$_2$H eluent) as appropriate.

| Intermediate | Example no. | ESMS m/z [M + H]$^+$ |
|---|---|---|
| 6 | 21 | 1107 |
| 5 | 22 | 1101 |
| 9 | 23 | 1101 |
| 11 | 24 | 1088 |

| Intermediate | Example no. | ESMS m/z [M + H]$^+$ |
|---|---|---|
| 12 | 25 | 1099 |
| 3 | Intermediate 13 | 1105 |
| 10 | 26 | 1088 |

Example 27

4"-O-{3-[[2-(3-Carboxy-1-ethyl-6-fluoro-4-oxo-1,4-dihydro-[1,8]naphthyridin-7-ylamino)-ethyl]-methylamino]-propyl}-6-O-methyl-11-desoxy-11-(R)-amino-erythromycin A 11,12-carbamate formate

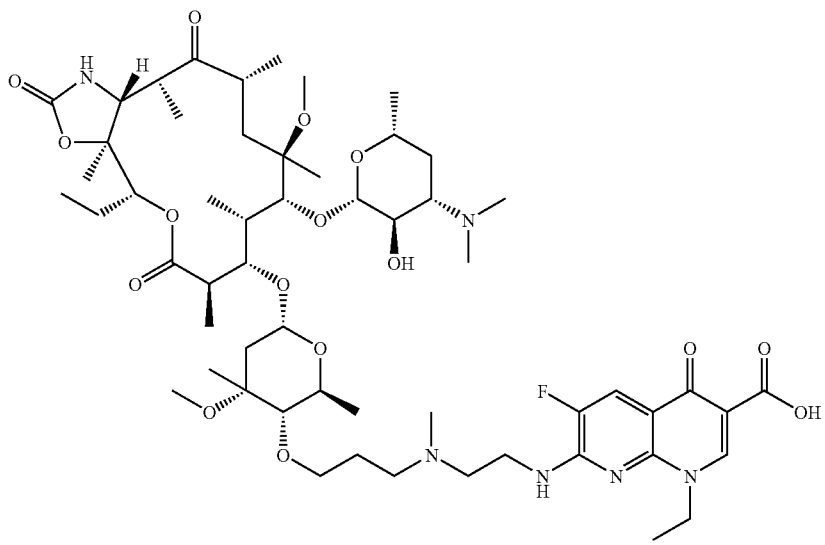

Example 28
4"-O-{3-[[2-(2-Carboxy-1-oxo-6,7-dihydro-1H,5H-pyrido[3,2,1-ij]quinolin-9-yloxy)-ethyl]-methylamino]-propyl}-6-O-methyl-11-desoxy-11-(R)-amino-erythromycin A 11,12-carbamate formate
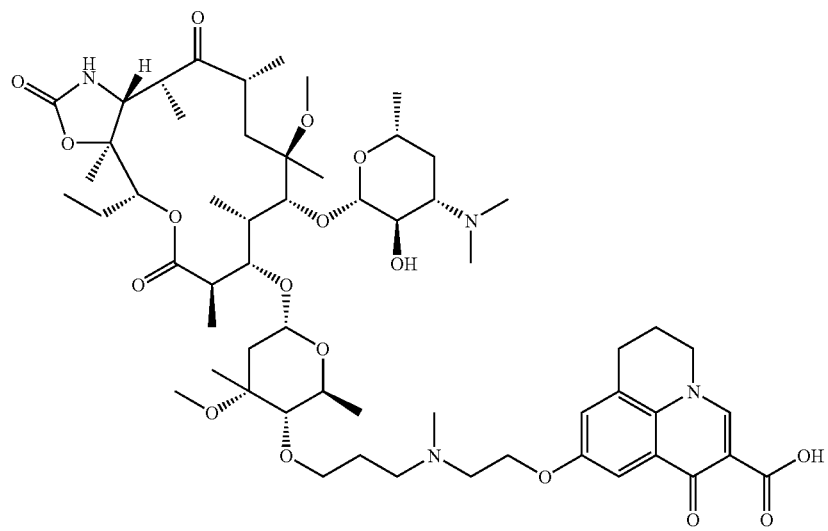
Example 29
4"-O-{3-[[3-(3-Carboxy-1-ethyl-4-oxo-1,4-dihydroquinolin-6-yl)-propyl]-methylamino]-propyl}-6-O-methyl-11-desoxy-11-(R)-amino-erythromycin A 11,12-carbamate formate
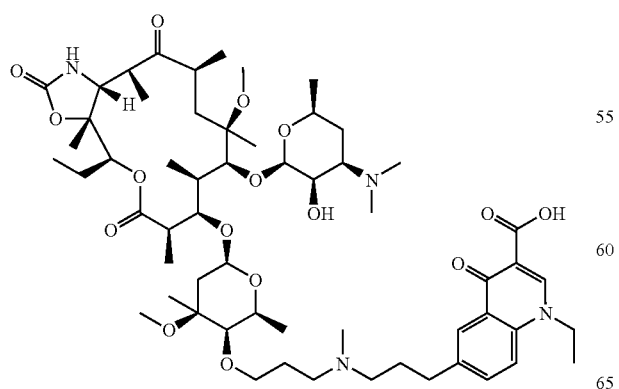

Example 30
4"-O-{3-[[3-(3-Carboxy-1-ethyl-4-oxo-1,4-dihydro-6-[1,8]naphthryidinyl)-propyl]-methylamino]-propyl}-6-O-methyl-11-desoxy-11-(R)-amino-erythromycin A 11,12-carbamate
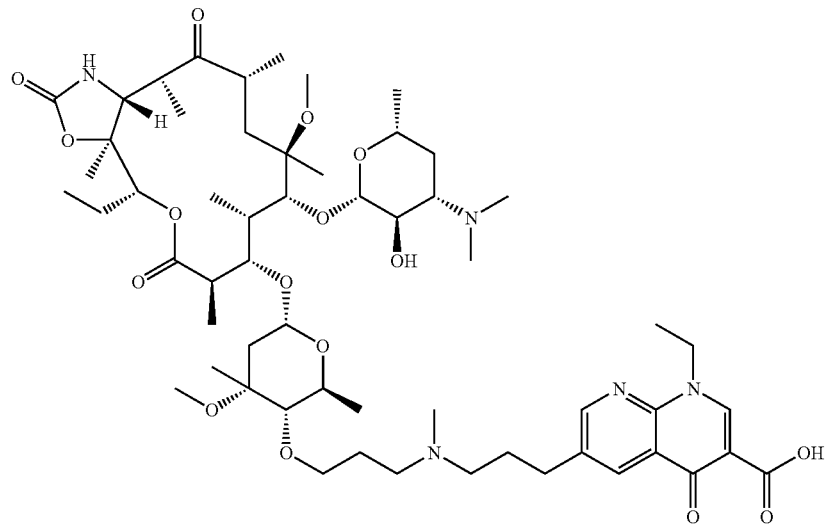
Example 31
4"-O-{3-[[3-(2-Carboxy-1-oxo-6,7-dihydro-1H,5H-pyrido[3,2,1-ij]quinolin-9-yl)-propyl]-methylamino]-propyl}-6-O-methyl-11-desoxy-11-(R)-amino-erythromycin A 11,12-carbamate
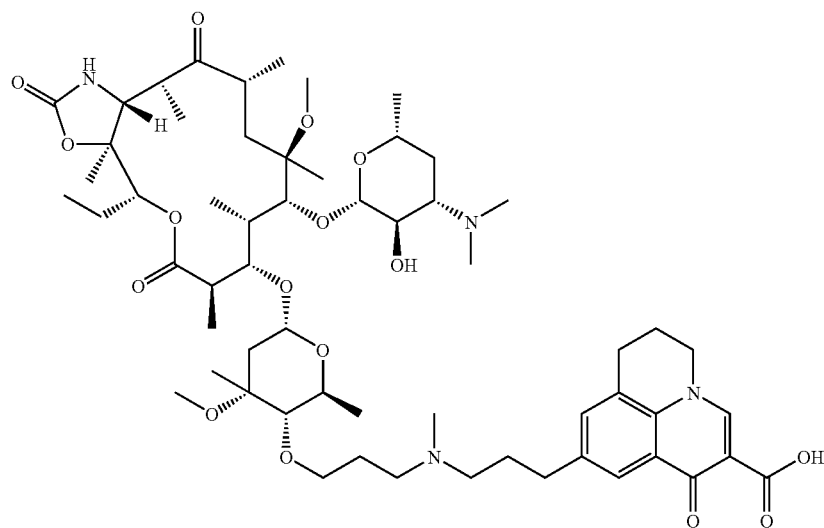

Example 32

4"-O-{3-[[2-(3-Carboxy-1-ethyl-4-oxo-1,4-dihydro-quinolin-6-ylsulfanyl)-ethyl]-methylamino]-propyl}-6-O-methyl-11-desoxy-11-(R)-amino-erythromycin A 11,12-carbamate

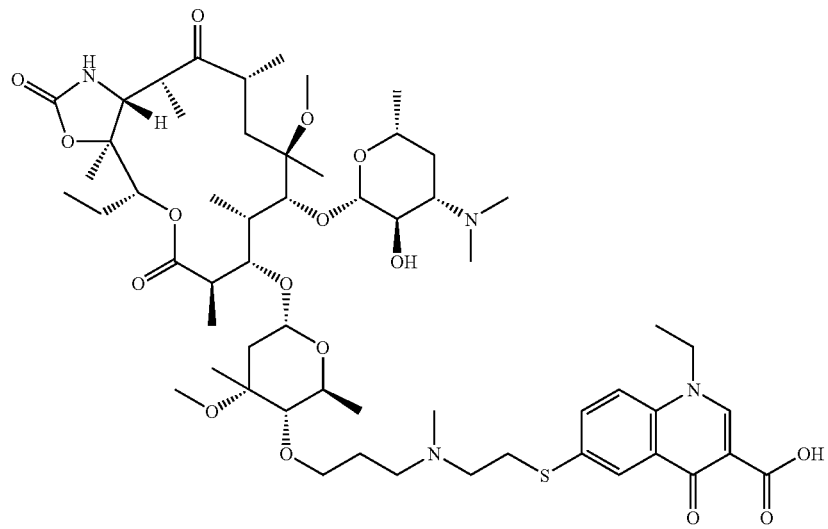

To a solution of starting material as tabulated below in chloroform (30 mL/mmol) was added formic acid (4 equivalents), and formaldehyde (37% by weight in water) (2 equivalents). The mixture was heated to 60° C. for 3 h then concentrated in vacuo to give a residue which was purified by chromatography (silica gel, 0-20% 2 M methanolic ammonia in dichloromethane) and/or by preparative reverse phase HPLC (MeCN/H$_2$O/0.1% HCO$_2$H eluent) to give the title compound.

| Starting material | Example no. | ESMS m/z [M + H]$^+$ |
|---|---|---|
| Example 21 | 27 | 1121 |
| Example 22 | 28 | 1115 |

| -continued | | |
|---|---|---|
| Starting material | Example no. | ESMS m/z [M + H]$^+$ |
| Example 8 | 29 | 1101 |
| Example 24 | 30 | 1102 |
| Example 25 | 31 | 1113 |
| Intermediate 13 | 32 | 1119 |

Example 33

4"-O-{3-[2-(3-Carboxy-6-fluoro-1-cyclopropyl-4-oxo-1,4-dihydro-quinolin-7-ylamino)-ethylcarbamoyl]-propyl}-azithromycin

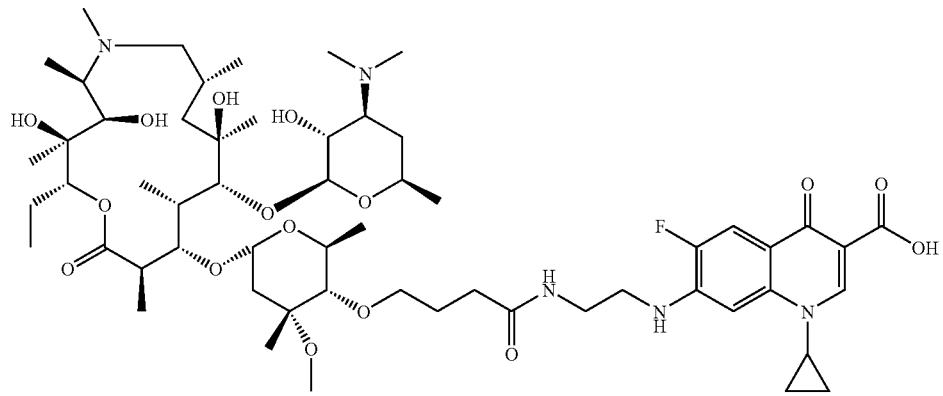

DIPEA (201.4 µL, 1.4 mol. equiv.) was added dropwise via a syringe at 0° C. to a solution of Intermediate 16c (181.7 mg, 0.22 mmoL) and HBTU (81.7 mg, 0.22 mmoL) in dry DMF (2.6 mL). The mixture was stirred for 15 minutes before 7-(2-amino-ethylamino)-6-fluoro-1-cyclopropyl-4-oxo-1,4-dihydro-quinoline-3-carboxylic acid (48.7 mg, 0.16 mmoL) was added over a period of 30 minutes. The reaction mixture was stirred at room temperature overnight, and then diluted with water (30 mL). The aqueous phase was extracted twice with EtOAc (2×50 mL), and the combined organic phases were washed sequentially with saturated aqueous NaHCO$_3$ (30 mL) and brine (30 mL). Drying with Na$_2$SO$_4$ and evaporation afforded 127.5 mg (71%) of the title compound as a colourless solid. MS (m/z) 1122 (MH$^+$).

Example 34

4"-O-{3-[2-(3-Carboxy-7-chloro-1-cyclopropyl-4-oxo-1,4-dihydro-quinolin-6-ylamino)-ethylcarbamoyl]-propyl}-azithromycin

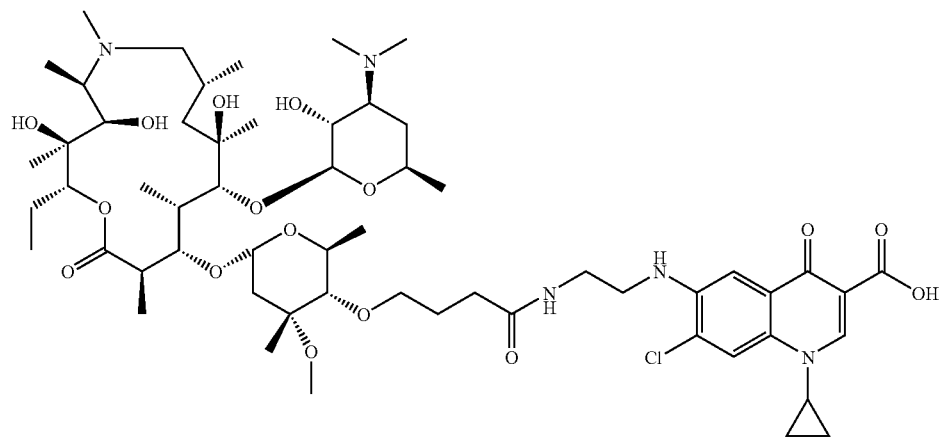

Starting from Intermediate 16c (834 mg, 1.0 mmoL) and Intermediate 1 (234.9 mg, 0.73 mmoL) using a similar procedure to that described in Example 33, the title compound (620.5 mg) was obtained. MS (m/z) 1138 (MH$^+$).

Example 35

4"-O-{4-[4-(3-Carboxy-6-fluoro-1-cyclopropyl-4-oxo-1,4-dihydro-quinolin-7-yl)-piperazin-1-yl]-4-oxo-butyl}-azithromycin

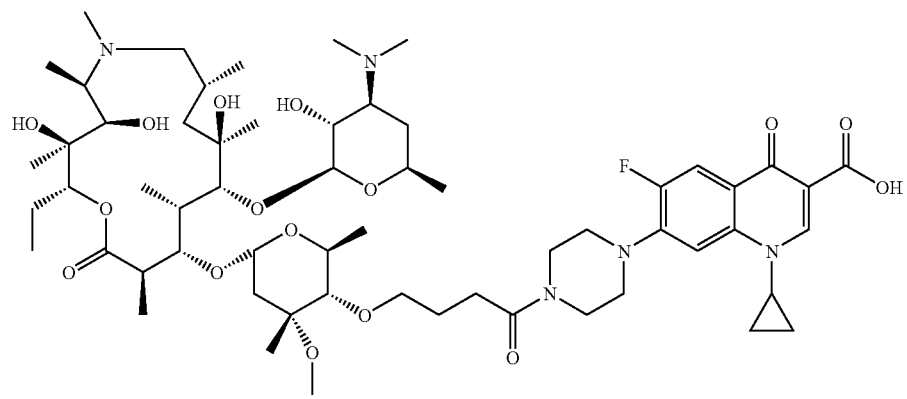

Starting from Intermediate 16c (667.2 mg, 0.8 mmoL) and 1-cyclopropyl-6-fluoro-4-oxo-7-piperazin-1-yl-1,4-dihydro-quinoline-3-carboxylic acid (192.7 mg, 0.58 mmoL) using the similar procedure to that described in Example 33 the title compound (460.3 mg) was obtained. MS (m/z) 1148 (MH$^+$).

Example 36

4"-O-{2-[4-(3-Carboxy-1-ethyl-4-oxo-1,4-dihydro-quinolin-6-yl)-piperazin-1-yl]-ethyl}-azithromycin 11,12-cyclic carbonate

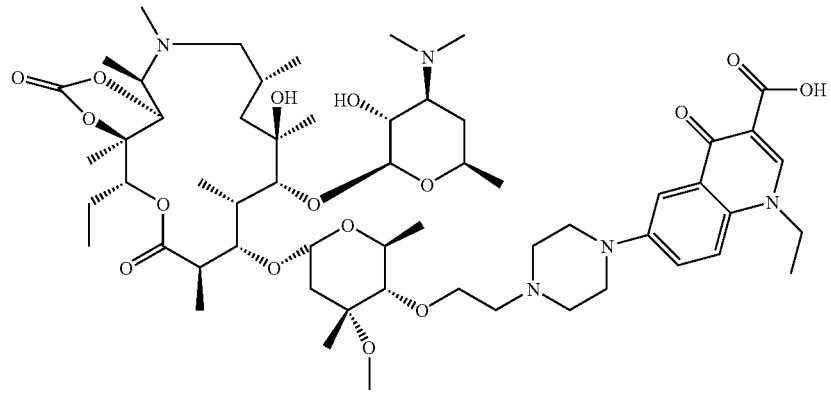

Intermediate 15 (114.4 mg, 0.14 mmoL) was dissolved in 0.9 mL of methanol. Three equivalents of Intermediate 17c (126.6 mg, 0.42 mmoL) were added as a 1 M solution in methanol (0.42 mL), followed by 0.43 mL of 1 M solution of acetic acid in methanol. The pH was checked and adjusted to about 6 with acetic acid, if necessary. NaCNBH$_3$ was added as a freshly prepared 0.3 M solution in methanol (0.19 mL), and the mixture was stirred at room temperature for 2 h. The reaction was quenched with a few drops of water and concentrated under reduced pressure. The residue was purified by silica gel chromatography (1-5% MeOH/0.5-1% triethylamine/dichloromethane) to give 100.3 mg (75%) of the title compound as a yellow solid. MS (m/z) 1102 (MH$^+$).

Example 37

4"-O-{2-[2-(3-Carboxy-7-chloro-1-cyclopropyl-4-oxo-1,4-dihydro-quinolin-6-ylamino)-ethylamino]-ethyl}-azithromycin 11,12-cyclic carbonate

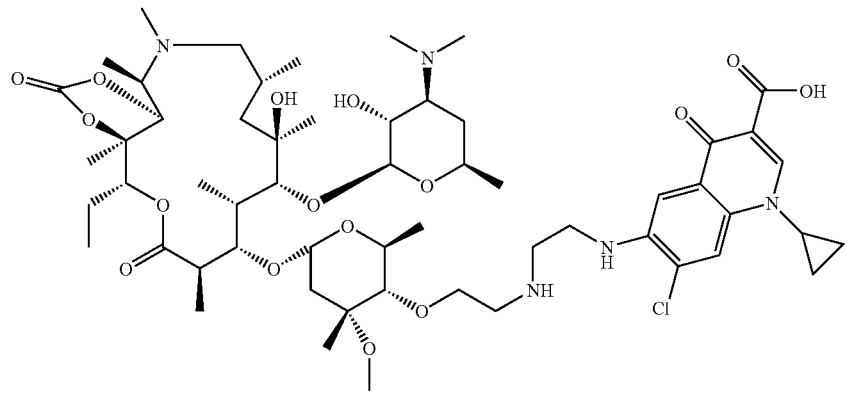

This method was adapted from the work of Debono et al. (J. Antibiot. 1989, 42, 1253-1267). A solution of Intermediate 15 (955.9 mg, 1.17 mmoL), Intermediate 1 (563.1 mg, 1.75 mmoL), and 22.5 mL of EtOAc was heated to 70° C. with stirring. Formic acid (58.9 mg, 1.28 mmoL) was added dropwise to the solution, and the temperature was lowered to 65° C. Stirring and heating was continued for 5 h. After cooling to room temperature, the reaction solution was washed twice with 25 mL portions of saturated aqueous NaHCO$_3$ and then once with 20 mL of saturated aqueous NaCl. The combined extracts were dried over anhydrous MgSO$_4$, filtered, and evaporated under reduced pressure to furnish crude product as a yellow foam. This material was taken up in 100 mL of hot Et$_2$O; insolubles were filtered and saved. The filtrate was treated with 30 mL of hot hexane, and again the resulting insoluble matter was filtered and saved. The filtrate was concentrated to about 7.5 mL by boiling off excess solvent. The resulting solution was allowed to cool to room temperature and then cooled to 5° C. for several hours. A colorless precipitate formed (630.6 mg). The filtrate was combined with the insolubles that were saved, and the mixture was then chromatographed on silica gel. Elution with 9:1 CH$_2$Cl$_2$-MeOH containing 1% NH$_4$OH afforded an additional amount of the title product (420.3 mg, 80% overall yield). MS (m/z) 1122 (MH$^+$).

Example 38

4"-O-{2-[2-(3-Carboxy-6-fluoro-1-cyclopropyl-4-oxo-1,4-dihydro-quinolin-7-ylamino)-ethylamino]-ethyl}-azithromycin 11,12-cyclic carbonate To a magnetically stirred solution of Intermediate 15 (2.17 g, 2.65 mmoL) in 8 mL of methanol was added 7-(2-aminoethylamino)-1-cyclopropyl-6-fluoro-4-oxo-1,4dihydro-quinoline-3-carboxylic acid (1.62 g, 5.3 mmol). After being stirred at room temperature for 30 min, the solution was treated with 0.15 mL (2.65 mmoL) of HOAc and cooled to 0° C. In 2 mL of MeOH, 563.4 mg (2.66 mmoL) of NaBH(OAc)$_3$ was then added over a period of 10 min. Stirring and cooling was continued for 10 min. The reaction mixture was worked up and the crude product was chromatographed on silica gel to furnish 1.99 g (68%) of the title product. MS (m/z) 1108 (MH$^+$).

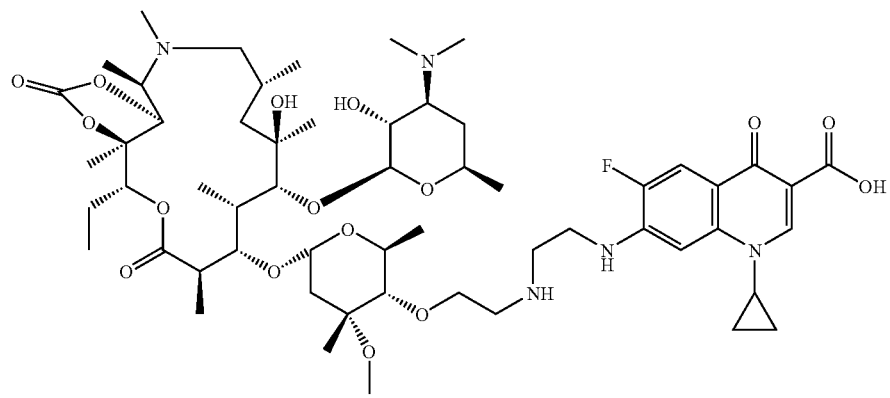

Example 39

4"-O-{2-[4-(3-Carboxy-6-fluoro-1-cyclopropyl-4-oxo-1,4-dihydro-quinolin-7-yl)-piperazin-1-yl]-ethyl}-azithromycin 11,12-cyclic carbonate

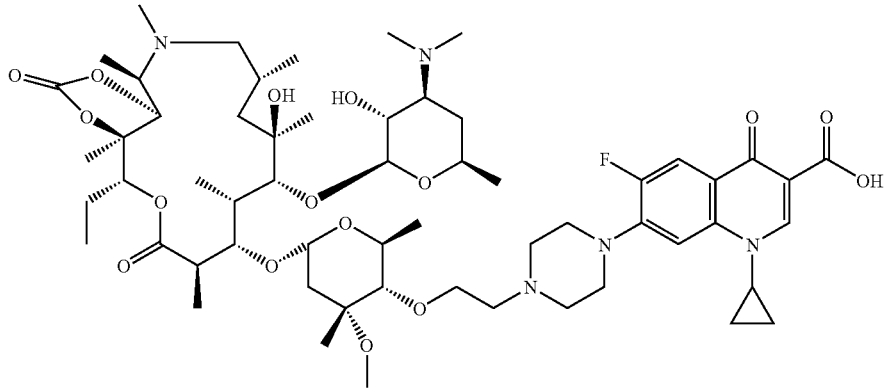

Starting from Intermediate 14 (817 mg, 1.0 mmoL) and 1-cyclopropyl-6-fluoro-4-oxo-7-piperazin-1-yl-1,4-dihydro-quinoline-3-carboxylic acid (994.1 mg, 3.0 mmoL) using a similar procedure to that described in Example 36 the title compound (702.1 mg) was obtained. MS (m/z) 1132 (MH+).

Example 40

4"-O-{2-[4-(3-Carboxy-1-ethyl-4-oxo-1,4-dihydro-quinolin-6-yl)-piperazin-1-yl]-ethyl}-azithromycin

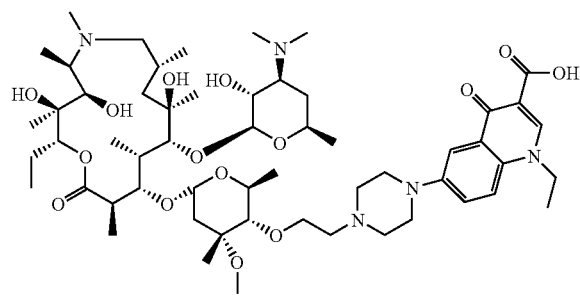

To a solution of Example 36 (1.101 g, 1.0 mmoL) in a THF-water mixture (1:1, 10.0 mL), was added LiOH (192 mg, 4.6 mmoL) at room temperature, and the resulting reaction mixture was stirred at the same temperature for 12 hours. The solvent was removed under reduced pressure, and the solid was azeotroped with toluene (5×5 mL) and finally dried under vacuum. The acid salt was dissolved in water and the resulting solution was made acidic by dropwise addition of aqueous HCl (2 M). The precipitate was filtered off to give 688.9 mg (64%) of the title compound as colourless solid. MS (m/z) 1076 (MH+).

Example 41

4"-O-{2-[2-(3-Carboxy-7-chloro-1-cyclopropyl-4-oxo-1,4-dihydro-quinolin-6-ylamino)-ethylamino]-ethyl}-azithromycin

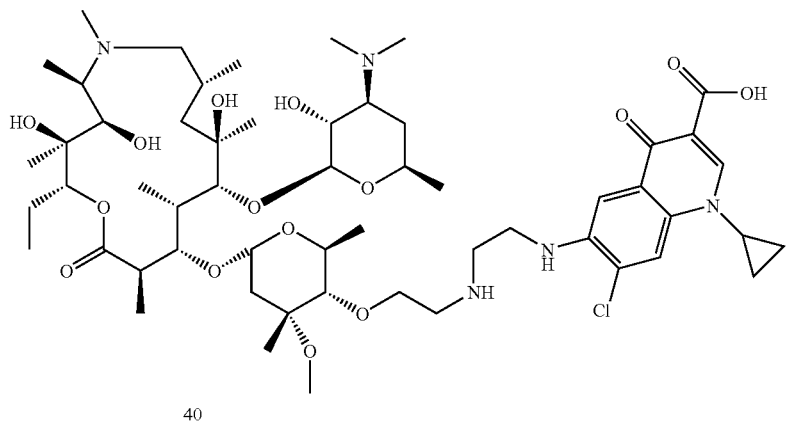

Starting from Example 37 (504.9 mg, 0.45 mmoL) according to the procedure of Example 40, the title compound (399.8 mg) was obtained. MS (m/z) 1096 (MH+).

Example 42

4"-O-{2-[2-(3-Carboxy-6-fluoro-1-cyclopropyl-4-oxo-1,4-dihydro-quinolin-7-ylamino)-ethylamino]-ethyl}-azithromycin

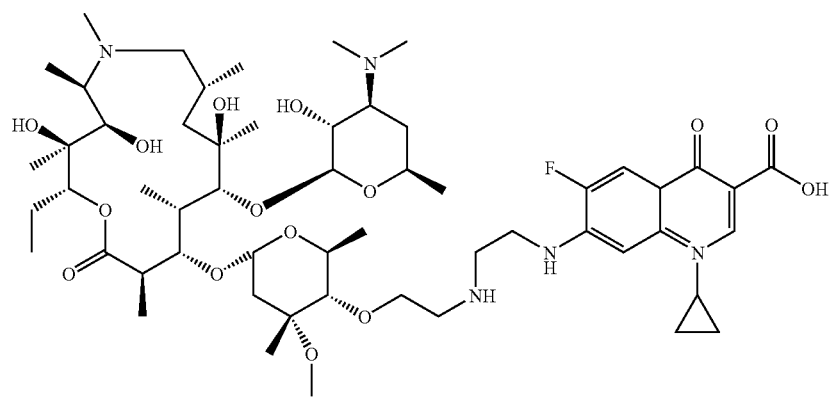

Starting from Example 38 (686.3 mg, 0.62 mmoL) according to the procedure of Example 40, the title compound (671.1 mg) was obtained. MS (m/z) 1082 (MH+).

Biological Data

Using a standard broth dilution method in microtitre, compounds were tested for antibacterial activity. The compounds in the above examples gave minimum inhibitory concentrations (MICs) less than 1 microgram per millilitre against erythromycin-sensitive and erythromycin-resistant strains of *Streptococcus pneumoniae* and *Streptococcus pyogenes*.

In addition, the MIC (μg/ml) of test compounds against various organisms was determined including:

*S. aureus* Smith ATCC 13709, *S. pneumoniae* SP030, *S. pyogenes* 3565, *E. faecalis* ATCC 29212, *H. influenzae* ATCC 49247, *M. catarrhalis* ATCC 23246.

Examples 1, 2, 5-7, 13, 15, 18-23, 25 and 27-32 have an MIC ≦1 μg/mL against *S. aureus* Smith ATCC 13709, *S. pneumoniae* SP030, *S. pyogenes* 3565 and *E. faecalis* ATCC 29212.

Examples 1, 2, 4, 6, 13-16, 18-21, 23 and 27-32 have an MIC ≦4 μg/mL against *H. influenzae* ATCC 49247 and *M. catarrhalis* ATCC 23246.

Examples 1-4, 6, 7, 9-15 and 18-32 have an MIC ≦1 μg/mL against erythromycin resistant strains of *Streptococcus pneumoniae* and *Streptococcus pyogenes*.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:
1. A compound of formula (I)

(I)

wherein
A is a bivalent radical selected from —C(O)—, —C(O)NH—, —NHC(O)—, —N($R^7$)—$CH_2$—, —$CH_2$—N($R^7$)—, —CH(N$R^8R^9$)— and —C(=N$R^{10}$)—;
$R^1$ is —O($CH_2$)$_d$X$R^{11}$;
$R^2$ is hydrogen or a hydroxyl protecting group;
$R^3$ is hydrogen, $C_{1-4}$alkyl, or $C_{3-6}$alkenyl optionally substituted by a 9 to 10 membered fused bicyclic heteroaryl;
$R^4$ is hydroxy, $C_{3-6}$alkenyloxy optionally substituted by a 9 to 10 membered fused bicyclic heteroaryl, or $C_{1-6}$alkoxy optionally substituted by $C_{1-6}$alkoxy or —O($CH_2$)$_e$N$R^7R^{12}$, $R^5$ is hydroxy, or
$R^4$ and $R^5$ taken together with the intervening atoms form a cyclic group having the following structure:

wherein
Y is a bivalent radical selected from the group consisting of —$CH_2$—, —CH(CN)—, —O—, —N($R^{13}$)— and —CH(S$R^{13}$)—;
$R^6$ is hydrogen or fluorine;
$R^7$ is hydrogen or $C_{1-6}$alkyl;
$R^8$ and $R^9$ are each independently hydrogen, $C_{1-6}$alkyl, —C(=N$R^{10}$)N$R^{14}R^{15}$ or —C(O)$R^{14}$, or
$R^8$ and $R^9$ together form =CH(C$R^{14}R^{15}$)$_p$aryl, =CH(C$R^{14}R^{15}$)$_p$heterocyclyl, =C$R^{14}R^{15}$ or =C($R^{14}$)C(O)O$R^{14}$, wherein the alkyl, aryl and heterocyclyl groups are optionally substituted by up to three groups independently selected from $R^{16}$;
$R^{10}$ is —O$R^{17}$, $C_{1-6}$alkyl, —($CH_2$)$_g$aryl, —($CH_2$)$_g$heterocyclyl or —($CH_2$)$_h$O($CH_2$)$_i$O$R^7$, wherein each $R^{10}$ group is optionally substituted by up to three groups independently selected from $R^{16}$;
$R^{11}$ is a heterocyclic group having the following structure:

$R^{12}$ is hydrogen or $C_{1-6}$alkyl;
$R^{13}$ is hydrogen or $C_{1-4}$alkyl optionally substituted by an optionally substituted phenyl, optionally substituted 5 or 6 membered heteroaryl or optionally substituted 9 to 10 membered fused bicyclic heteroaryl;
$R^{14}$ and $R^{15}$ are each independently hydrogen or $C_{1-6}$alkyl;
$R^{16}$ is halogen, cyano, nitro, trifluoromethyl, azido, —C(O)$R^{21}$, —C(O)O$R^{21}$, —OC(O)$R^{21}$, —OC(O)O$R^{21}$, —N$R^{22}$C(O)$R^{23}$, —C(O)N$R^{22}R^{23}$, —N$R^{22}R^{23}$, hydroxy, $C_{1-6}$alkyl, —S(O)$_k$$C_{1-6}$alkyl, $C_{1-6}$alkoxy, —($CH_2$)$_m$aryl or —($CH_2$)$_m$heteroaryl, wherein the alkoxy group is optionally substituted by up to three groups independently selected from the group consisting of —N$R^{14}R^{15}$, halogen and —O$R^{14}$, and the aryl and heteroaryl groups are optionally substituted by up to five groups independently selected from halogen, cyano, nitro, trifluoromethyl, azido, —C(O)$R^{24}$, —C(O)O$R^{24}$, —OC(O)O$R^{24}$, —N$R^{25}$C(O)$R^{26}$, —C(O)N$R^{25}R^{26}$, —N$R^{25}R^{26}$, hydroxy, $C_{1-6}$alkyl and $C_{1-6}$alkoxy;
$R^{17}$ is hydrogen, $C_{1-6}$alkyl, $C_{3-7}$cycloalkyl, $C_{3-6}$alkenyl or a 5 or 6 membered heterocyclic group, wherein the alkyl, cycloalkyl, alkenyl and heterocyclic groups are optionally substituted by up to three substituents independently selected from the group consisting of optionally substituted 5 or 6 membered heterocyclic, optionally substituted 5 or 6 membered heteroaryl, —OR$^{27}$, —S(O)$_n$R$^{27}$, —NR$^{27}$R$^{28}$, —CONR$^{27}$R$^{28}$, halogen and cyano;

R$^{18}$ is hydrogen, —C(O)OR$^{29}$, —C(O)NHR$^{29}$, —C(O)CH$_2$NO$_2$ or —C(O)CH$_2$SO$_2$R$^7$;

R$^{19}$ is hydrogen, C$_{1-4}$alkyl optionally substituted by hydroxy or C$_{1-4}$alkoxy, C$_{3-7}$cycloalkyl, or optionally substituted phenyl or benzyl;

R$^{20}$ is halogen, C$_{1-4}$alkyl, C$_{1-4}$thioalkyl, C$_{1-4}$alkoxy, —NH$_2$, —NH(C$_{1-4}$alkyl) or —N(C$_{1-4}$alkyl)$_2$;

R$^{21}$ is hydrogen, C$_{1-10}$alkyl, —(CH$_2$)$_p$aryl or —(CH$_2$)$_p$heteroaryl;

R$^{22}$ and R$^{23}$ are each independently hydrogen, —OR$^{14}$, C$_{1-6}$alkyl, —(CH$_2$)$_q$aryl or —(CH$_2$)$_q$heterocyclyl;

R$^{24}$ is hydrogen, C$_{1-10}$alkyl, —(CH$_2$)$_r$aryl or —(CH$_2$)$_r$heteroaryl;

R$^{25}$ and R$^{26}$ are each independently hydrogen, —OR$^{14}$, C$_{1-6}$alkyl, —(CH$_2$)$_s$aryl or —(CH$_2$)$_s$heterocyclyl;

R$^{27}$ and R$^{28}$ are each independently hydrogen, C$_{1-4}$alkyl or C$_{1-4}$alkoxyC$_{1-4}$alkyl;

R$^{29}$ is hydrogen,
C$_{1-6}$alkyl optionally substituted by up to three groups independently selected from the group consisting of halogen, cyano, C$_{1-4}$alkoxy optionally substituted by phenyl or C$_{1-4}$alkoxy, —C(O)C$_{1-6}$alkyl, —C(O)OC$_{1-6}$alkyl, —OC(O)C$_{1-6}$alkyl, —OC(O)OC$_{1-6}$alkyl, —C(O)NR$^{32}$R$^{33}$, —NR$^{32}$R$^{33}$ and phenyl optionally substituted by nitro or —C(O)OC$_{1-6}$alkyl,
—(CH$_2$)$_w$C$_{3-7}$cycloalkyl,
—(CH$_2$)$_w$heterocyclyl,
—(CH$_2$)$_w$heteroaryl,
—(CH$_2$)$_w$aryl,
C$_{3-6}$alkenyl, or
C$_{3-6}$alkynyl;

R$^{30}$ is hydrogen, C$_{1-4}$alkyl, C$_{3-7}$cycloalkyl, optionally substituted phenyl or benzyl, acetyl or benzoyl;

R$^{31}$ is hydrogen or R$^{20}$, or R$^{31}$ and R$^{19}$ are linked to form the bivalent radical —O(CH$_2$)$_2$— or —(CH$_2$)$_t$—;

R$^{32}$ and R$^{33}$ are each independently hydrogen or C$_{1-6}$alkyl optionally substituted by phenyl or —C(O)OC$_{1-6}$alkyl, or R$^{32}$ and R$^{33}$, together with the nitrogen atom to which they are bound, form a 5 or 6 membered heterocyclic group optionally containing one additional heteroatom selected from oxygen, nitrogen and sulfur;

X is —U(CH$_2$)$_v$B—, —U(CH$_2$)$_v$— or a group selected from:

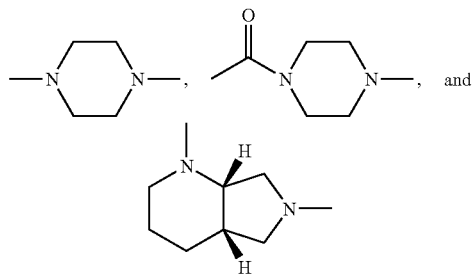

U and B are independently a divalent radical selected from —N(R$^{30}$)—, —O—, —S(O)$_z$—, —N(R$^{30}$)C(O)—, —C(O)N(R$^{30}$)— and —N[C(O)R$^{30}$]—;

W is —C(R$^{31}$)— or a nitrogen atom;

d is an integer from 2 to 6;

e is an integer from 2 to 4;

f, g, h, m, p, q, r, s and w are each independently integers from 0 to 4;

i is an integer from 1 to 6;

j, k, n and z are each independently integers from 0 to 2;

t is 2 or 3;

v is an integer from 1 to 8;

or a pharmaceutically acceptable salt thereof.

2. A compound according to claim 1, or a pharmaceutically acceptable salt therof, wherein A is —C(O)— or —N(R$^7$)—CH$_2$—.

3. A compound according to claim 1, or a pharmaceutically acceptable salt therof, wherein X is —U(CH$_2$)$_v$B— or —U(CH$_2$)$_v$.

4. A compound according to claim 1, or a pharmaceutically acceptable salt therof, wherein d is 2 or 3.

5. A compound according to claim 1, or a pharmaceutically acceptable salt therof, wherein R$^{11}$ is a heterocyclic group of the following formula:

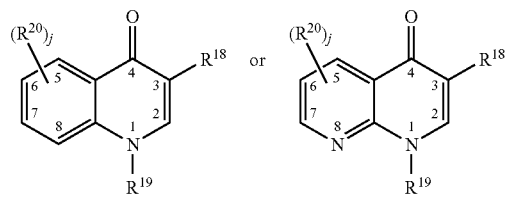

wherein the heterocyclic is linked in the 6 or 7 position and j, R$^{18}$, R$^{19}$ and R$^{20}$ are as defined in claim 1;

a heterocyclic group of the following formula:

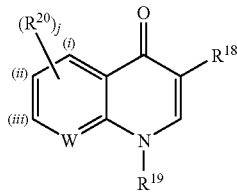

wherein the heterocylic is linked in the (ii) or (iii) position, W is —C(R$^{31}$)— and R$^{31}$ and R$^{19}$ are linked to form the bivalent radical —(CH$_2$)$_t$— as defined in claim 1, and j, R$^{18}$, R$^{19}$ and R$^{20}$ are as defined in claim 1; or a heterocyclic group of the following formula:

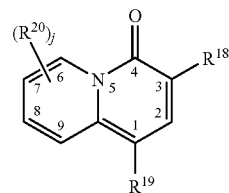

wherein the heterocyclic is linked in the 7 or 8 position and j, R$^{18}$, R$^{19}$ and R$^{20}$ are as defined in claim 1.

6. A compound selected from:

4"-O-(2-{[2-(3-carboxy-1-cyclopropyl-6-fluoro-4-oxo-1,4-dihydro-quinolin-7-ylamino)-ethyl]-methylamino}-ethyl)-6-O-methyl-erythromycin A 11,12-carbonate;

4"-O-(3-{[2-(3-carboxy-1-cyclopropyl-6-fluoro-4-oxo-1,4-dihydro-quinolin-7-ylamino)ethyl]-methylamino}-propyl)-6-O-methyl-erythromycin A 11,12-carbonate;

4"-O-{3-[2-(2-carboxy-1-oxo-6,7-dihydro-1H,5H-pyrido[3,2,1-ij]quinoline-9-yloxy)-ethylamino]-propyl}-6-O-methyl-erythromycin A 11,12-carbonate;

4"-O-{3-[[(3-{[3-(3-carboxy-1-ethyl-4-oxo-1,4-dihydro-quinolin-6-yl)propyl]-methylamino}-propyl)-6-O-methyl-erythromycin A 11,12-carbonate;

4"-O-(3-{[2-(3-carboxy-1-ethyl-6-fluoro-4-oxo-1,4-dihydro-[1,8]naphthyridin-7-ylamino)ethyl]-methylamino}-propyl)-6-O-methyl-erythromycin A 11,12-carbonate;

4"-O-{2-[2-(3-carboxy-1-ethyl-6-fluoro-4-oxo-1,4-dihydro-[1,8]naphthyridin-7-ylamino)ethyl]-methylamino}-ethyl}-6-O-methyl-erythromycin A;

4"-O-{3-[[3-(3-carboxy-1-ethyl-4-oxo-1,4-dihydro-quinolin-6-yl)-propyl]-methylamino]-propyl}-6-O-methyl-11-desoxy-11-(R)-amino-erythromycin A 11,12-carbamate;

4"-O-{3-[[2-(3-carboxy-1-ethyl-4-oxo-1,4-dihydro-quinolin-6-ylsulfanyl)-ethyl]-methylamino]-propyl}-6-O-methyl-11-desoxy-11-(R)-amino-erythromycin A 11,12-carbamate;

4"-O-{3-[2-(3-carboxy-7-chloro-1-cyclopropyl-4-oxo-1,4-dihydro-quinolin-6-ylamino)-ethylcarbamoyl]-propyl}-azithromycin;

4"-O-{2-[2-(3-carboxy-6-fluoro-1-cyclopropyl-4-oxo-1,4-dihydro-quinolin-7-ylamino)-ethylamino]-ethyl}-azithromycin 11,12-cyclic carbonate;

4"-O-{2-[2-(3-carboxy-7-chloro-1-cyclopropyl-4-oxo-1,4-dihydro-quinolin-6-ylamino)-ethylamino]-ethyl}-azithromycin; and 4"-O-{2-[2-(3-carboxy-6-fluoro-1-cyclopropyl-4-oxo-1,4-dihydro-quinolin-7-ylamino)-ethylamino]-ethyl}-azithromycin;

or a pharmaceutically acceptable salt thereof.

7. A process for the preparation of a compound as claimed in claim 1 which comprises:

a) reacting a compound of formula (II)

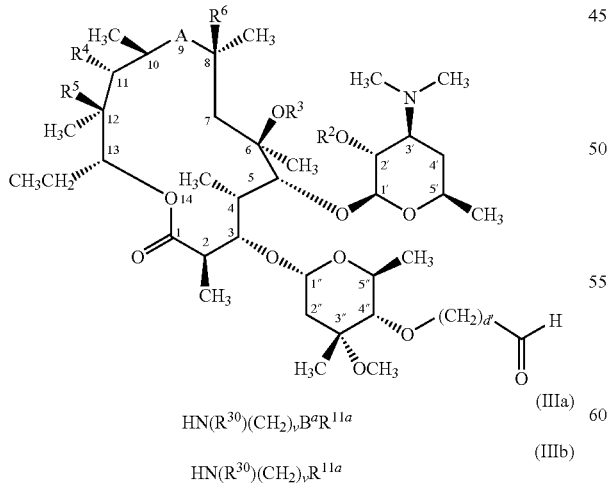

(II)

with a suitable amine (IIIa) or (IIIb), wherein $B^a$ and $R^{11a}$ are B and $R^{11}$ as defined in claim 1 or groups convertible to B and $R^{11}$;

b) reacting a compound of formula (V)

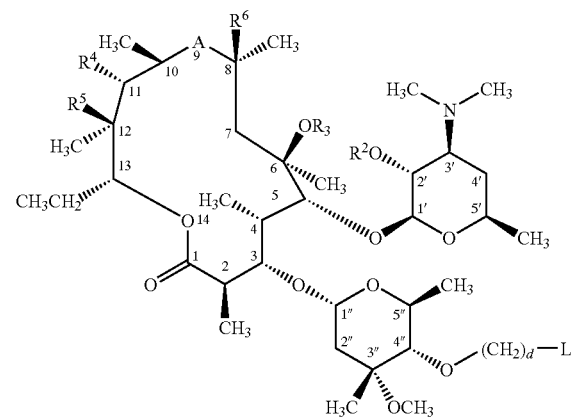

(V)

with a compound of formula $X^a R^{11a}$ (IV), wherein $R^{11a}$ is $R^{11}$ as defined in claim 1 or a group convertible to $R^{11}$ and $X^a$ is —U(CH$_2$)$_v$— or —U(CH$_2$)$_v$B—, or a group convertible to —U(CH$_2$)$_v$— or —U(CH$_2$)$_v$B—, in which U is a group selected from —N(R$^{30}$)— and —S—, and L is suitable leaving group, to produce a compound of formula (I) wherein U is a group selected from —N(R$^{30}$)— and —S—;

c) oxidizing a compound of formula (I) wherein U or B is —S(O)$_z$ and wherein z is 0 to provide a compound of formula (I) wherein U or B is —S(O)$_z$ and z is 1 or 2;

d) where U is —O—, reacting a compound of formula (VII)

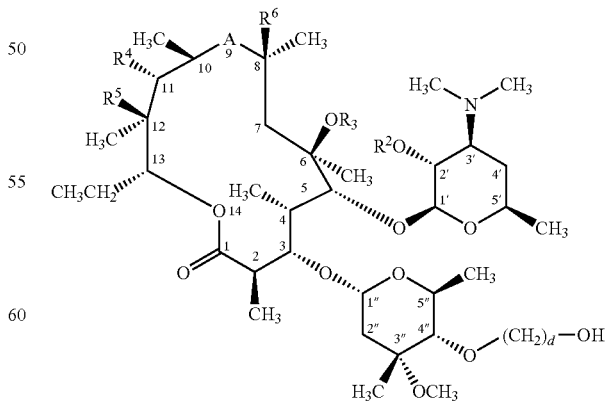

(VII)

with a suitable compound of formula $X^a R^{11a}$ in the presence of a catalyst; or e) where U is —C(O)N($R^{30}$)—, reacting a compound of formula (VIII)

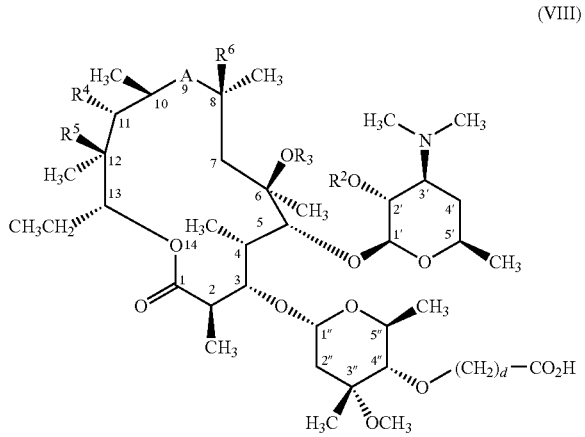
(VIII)

with a suitable amine compound,
and thereafter, if required, subjecting the resulting compound to one or more of the following operations:
i) removal of the protecting group $R^2$,
ii) conversion of $X^a R^{11a}$ to $XR^{11}$,
iii) conversion of $B^a R^{11a}$ to $R^{11}$,
iv) conversion of $R^{11a}$ to $R^{11}$, and
v) conversion of the resultant compound of formula (I) into a pharmaceutically acceptable salt thereof.

8. A method for the treatment of the human or non-human animal body to combat a bacterial infection comprising administration to a body in need of such treatment of an effective amount of a compound as claimed in claim 1 or a pharmaceutiaclly acceptable salt thereof.

9. A pharmaceutical composition comprising at least one compound as claimed in claim 1, or a pharmaceutiaclly acceptable salt thereof, in association with a pharmaceutically acceptable excipient, diluent or carrier.

10. A compound of formula (IA)

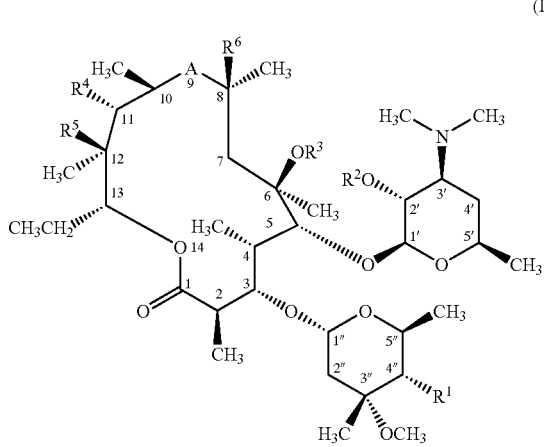
(IA)

wherein
A is a bivalent radical selected from —C(O)—, —C(O)NH—, —NHC(O)—, —N($R^7$)—CH$_2$—, —CH$_2$—N($R^7$)—, —CH(N$R^8 R^9$)— and —C(=N$R^{10}$)—;
$R^1$ is —O(CH$_2$)$_d$X$R^{11}$;

$R^2$ is hydrogen or a hydroxyl protecting group;
$R^3$ is hydrogen, $C_{1-4}$alkyl, or $C_{3-6}$alkenyl optionally substituted by a 9 to 10 membered fused bicyclic heteroaryl;
$R^4$ is hydroxy, $C_{3-6}$alkenyloxy optionally substituted by a 9 to 10 membered fused bicyclic heteroaryl, or $C_{1-6}$alkoxy optionally substituted by $C_{1-6}$alkoxy or —O(CH$_2$)$_e$N$R^7 R^{12}$,
$R^5$ is hydroxy, or
$R^4$ and $R^5$ taken together with the intervening atoms form a cyclic group having the following structure:

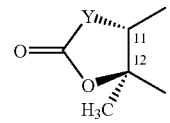

wherein
Y is a bivalent radical selected from the group consisting of —CH$_2$—, —CH(CN)—, —O—, —N($R^{13}$)— and —CH(S$R^{13}$)—;
$R^6$ is hydrogen or fluorine;
$R^7$ is hydrogen or $C_{1-6}$alkyl;
$R^8$ and $R^9$ are each independently hydrogen, $C_{1-6}$alkyl, —C(=N$R^{10}$)N$R^{14}R^{15}$ or —C(O)$R^{14}$, or
$R^8$ and $R^9$ together form =CH(C$R^{14}R^{15}$)$_p$aryl, =CH(C$R^{14}R^{15}$)$_p$heterocyclyl, =C$R^{14}R^{15}$ or =C($R^{14}$)C(O)O$R^{14}$, wherein the alkyl, aryl and heterocyclyl groups are optionally substituted by up to three groups independently selected from $R^{16}$;
$R^{10}$ is —O$R^{17}$, $C_{1-6}$alkyl, —(CH$_2$)$_g$aryl, —(CH$_2$)$_g$heterocyclyl or —(CH$_2$)$_h$O(CH$_2$)$_i$O$R^7$, wherein each $R^{10}$ group is optionally substituted by up to three groups independently selected from $R^{16}$;
$R^{11}$ is a heterocyclic group having the following structure:

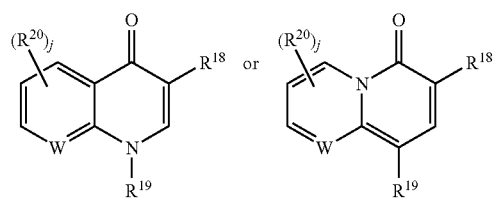

$R^{12}$ is hydrogen or $C_{1-6}$alkyl;
$R^{13}$ is hydrogen or $C_{1-4}$alkyl substituted by a group selected from the group consisting of optionally substituted phenyl, optionally substituted 5 or 6 membered heteroaryl and optionally substituted 9 to 10 membered fused bicyclic heteroaryl;
$R^{14}$ and $R^{15}$ are each independently hydrogen or $C_{1-6}$alkyl;
$R^{16}$ is halogen, cyano, nitro, trifluoromethyl, azido, —C(O)$R^{21}$, —C(O)O$R^{21}$, —OC(O)$R^{21}$, —OC(O)O$R^{21}$, —N$R^{22}$C(O)$R^{23}$, —C(O)N$R^{22}R^{23}$, —N$R^{22}R^{23}$, hydroxy, $C_{1-6}$alkyl, —S(O)$_k C_{1-6}$alkyl, $C_{1-6}$alkoxy, —(CH$_2$)$_m$aryl or —(CH$_2$)$_m$heteroaryl, wherein the alkoxy group is optionally substituted by up to three groups independently selected from the group consisting of —N$R^{14}R^{15}$, halogen and —O$R^{14}$, and the aryl and heteroaryl groups are optionally substituted by up to five groups independently selected from the group consisting of halogen, cyano, nitro, trifluoromethyl, azido, —C(O)R$^{24}$, —C(O)OR$^{24}$, —OC(O)OR$^{24}$, —NR$^{25}$C(O)R$^{26}$, —C(O)NR$^{25}$R$^{26}$, —NR$^{25}$R$^{26}$, hydroxy, C$_{1-6}$alkyl and C$_{1-6}$alkoxy;

R$^{17}$ is hydrogen, C$_{1-6}$alkyl, C$_{3-7}$cycloalkyl, C$_{3-6}$alkenyl or a 5 or 6 membered heterocyclic group, wherein the alkyl, cycloalkyl, alkenyl and heterocyclic groups are optionally substituted by up to three substituents independently selected from the group consisting of optionally substituted 5 or 6 membered heterocyclic group, optionally substituted 5 or 6 membered heteroaryl, —OR$^{27}$, —S(O)$_n$R$^{27}$, —NR$^{27}$R$^{28}$, —CONR$^{27}$R$^{28}$, halogen and cyano;

R$^{18}$ is hydrogen, —C(O)OR$^{29}$, —C(O)NHR$^{29}$ or —C(O)CH$_2$NO$_2$;

R$^{19}$ is hydrogen, C$_{1-4}$alkyl optionally substituted by hydroxy or C$_{1-4}$alkoxy, C$_{3-7}$cycloalkyl, or optionally substituted phenyl or benzyl;

R$^{20}$ is halogen, C$_{1-4}$alkyl, C$_{1-4}$thioalkyl, C$_{1-4}$alkoxy, —NH$_2$, —NH(C$_{1-4}$alkyl) or —N(C$_{1-4}$alkyl)$_2$;

R$^{21}$ is hydrogen, C$_{1-10}$alkyl, —(CH$_2$)$_p$aryl or —(CH$_2$)$_p$heteroaryl;

R$^{22}$ and R$^{23}$ are each independently hydrogen, —OR$^{14}$, C$_{1-6}$alkyl, —(CH$_2$)$_q$aryl or —(CH$_2$)$_q$heterocyclyl;

R$^{24}$ is hydrogen, C$_{1-10}$alkyl, —(CH$_2$)$_r$aryl or —(CH$_2$)$_r$heteroaryl;

R$^{25}$ and R$^{26}$ are each independently hydrogen, —OR$^{14}$, C$_{1-6}$alkyl, —(CH$_2$)$_s$aryl or —(CH$_2$)$_s$heterocyclyl;

R$^{27}$ and R$^{28}$ are each independently hydrogen, C$_{1-4}$alkyl or C$_{1-4}$alkoxyC$_{1-4}$alkyl;

R$^{29}$ is hydrogen or C$_{1-6}$alkyl optionally substituted by up to three groups independently selected from the group consisting of halogen, C$_{1-4}$alkoxy, —OC(O)C$_{1-6}$alkyl and —OC(O)OC$_{1-6}$alkyl;

R$^{30}$ is hydrogen, C$_{1-4}$alkyl, C$_{3-7}$cycloalkyl, optionally substituted phenyl or benzyl, acetyl or benzoyl;

R$^{31}$ is hydrogen or R$^{20}$, or R$^{31}$ and R$^{19}$ are linked to form the bivalent radical —O(CH$_2$)$_2$— or —(CH$_2$)$_t$—;

X is —U(CH$_2$)$_v$B—, —U(CH$_2$)$_v$— or a group selected from:

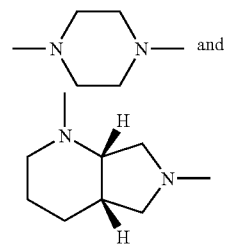

U and B are independently a divalent radical selected from —N(R$^{30}$)—, —O—, —S(O)$_z$—, —N(R$^{30}$)C(O)—, —C(O)N(R$^{30}$)— and —N[C(O)R$^{30}$]—;

W is —C(R$^{31}$)— or a nitrogen atom;

d is an integer from 2 to 6;

e is an integer from 2 to 4;

f, g, h, m, p, q, r and s are each independently integers from 0 to 4;

i is an integer from 1 to 6;

j, k, n and z are each independently integers from 0 to 2;

t is 2 or 3;

v is an integer from 2 to 8;

or a pharmaceutically acceptable salt thereof.

* * * * *